US 9,884,105 B2

(12) United States Patent
Kistner et al.

(10) Patent No.: US 9,884,105 B2
(45) Date of Patent: Feb. 6, 2018

(54) PRODUCTION OF VIRAL VACCINE

(75) Inventors: Otfried Kistner, Vienna (AT);
Falko-Guenter Falkner, Orth/Donau (AT); Hartmut Ehrlich, Vienna (AT); Noel Barrett, Klosterneuburg/Weidling (AT)

(73) Assignee: OLOGY BIOSERVICES, INC., Alachua, FL (US)

( * ) Notice: Subject to any disclaimer, the term of this patent is extended or adjusted under 35 U.S.C. 154(b) by 0 days.

(21) Appl. No.: 12/639,917

(22) Filed: Dec. 16, 2009

(65) Prior Publication Data

US 2010/0189745 A1   Jul. 29, 2010

Related U.S. Application Data

(60) Provisional application No. 61/122,961, filed on Dec. 16, 2008.

(51) Int. Cl.
| A61K 39/145 | (2006.01) |
| C12N 7/00 | (2006.01) |
| A61K 39/12 | (2006.01) |
| A61K 39/00 | (2006.01) |

(52) U.S. Cl.
CPC ............ *A61K 39/145* (2013.01); *A61K 39/12* (2013.01); *C12N 7/00* (2013.01); *A61K 2039/5254* (2013.01); *A61K 2039/5258* (2013.01); *C12N 2760/16134* (2013.01); *C12N 2760/16161* (2013.01)

(58) Field of Classification Search
None
See application file for complete search history.

(56) References Cited

U.S. PATENT DOCUMENTS

| 4,552,758 | A | 11/1985 | Murphy et al. |
| 6,001,634 | A | 12/1999 | Palese et al. |
| 6,022,726 | A | 2/2000 | Palese et al. |
| 6,146,873 | A | 11/2000 | Kistner et al. |
| 6,468,544 | B1 | 10/2002 | Egorov et al. |
| 6,573,079 | B1 | 6/2003 | Palese et al. |
| 6,635,246 | B1 | 10/2003 | Barrett et al. |
| 6,669,943 | B1 | 12/2003 | Palese et al. |
| 6,803,041 | B2 | 10/2004 | Mellencamp |
| 6,866,853 | B2 | 3/2005 | Egorov et al. |
| 7,037,707 | B2 | 5/2006 | Webster et al. |
| 7,132,271 | B2 | 11/2006 | Lau |
| 7,459,162 | B2 | 12/2008 | Yang et al. |
| 7,465,456 | B2 | 12/2008 | Hoffmann et al. |
| 7,504,109 | B2 | 3/2009 | Yang et al. |
| 7,510,719 | B2 | 3/2009 | Dang et al. |
| 7,527,800 | B2 | 5/2009 | Yang et al. |
| 7,566,458 | B2 | 7/2009 | Yang et al. |
| 7,601,356 | B2 | 10/2009 | Jin et al. |
| 2003/0157131 | A1 | 8/2003 | Egorov et al. |
| 2004/0109877 | A1 | 6/2004 | Palese et al. |
| 2005/0042229 | A1 | 2/2005 | Yang et al. |
| 2005/0158342 | A1 | 7/2005 | Kemble et al. |
| 2006/0110406 | A1 | 5/2006 | Kemble et al. |
| 2006/0153872 | A1 | 7/2006 | Dang et al. |
| 2006/0252132 | A1 | 11/2006 | Yang et al. |
| 2007/0172929 | A1 | 7/2007 | Maassab et al. |
| 2008/0014217 | A1 | 1/2008 | Hanon et al. |
| 2008/0057081 | A1 | 3/2008 | Yang et al. |
| 2008/0069821 | A1 | 3/2008 | Yang et al. |
| 2008/0187546 | A1 | 8/2008 | Wasmoen et al. |
| 2009/0136530 | A1 | 5/2009 | Yang et al. |
| 2009/0175907 | A1 | 7/2009 | Hoffman et al. |
| 2009/0175908 | A1 | 7/2009 | Yang et al. |
| 2009/0175909 | A1 | 7/2009 | Yang et al. |
| 2009/0208527 | A1 | 8/2009 | Kemble et al. |
| 2009/0246225 | A1 | 10/2009 | Trager et al. |
| 2009/0297554 | A1 | 12/2009 | Lu et al. |

FOREIGN PATENT DOCUMENTS

| EP | 399843 A2 | 11/1990 |
| WO | WO-1995/17210 A1 | 6/1995 |
| WO | WO-2003/091401 A2 | 11/2003 |
| WO | WO-2005/062820 A2 | 7/2005 |
| WO | WO-2005/115448 A2 | 12/2005 |
| WO | WO-2005/116258 A2 | 12/2005 |
| WO | WO-2005/116260 A2 | 12/2005 |
| WO | WO-2006/041819 A1 | 4/2006 |
| WO | WO-2006/063053 A2 | 6/2006 |
| WO | WO-2006/098901 A2 | 9/2006 |
| WO | WO-2007/048089 A2 | 4/2007 |

(Continued)

OTHER PUBLICATIONS

Huber et al., Journal of Infectious Diseases, 2006, 193:677-684.*
Khiabanian et al., PLoS ONE, Oct. 2009, 4(10):e7366, 7 pages.*
Ashkenazi et al., Pediatr. Infect. Dis. J., 2006, 25:870-879.*
Aly et al., Epidemiological findings of outbreaks of disease caused by highly pathogenic H5N1 avian influenza virus in poultry in Egypt during 2006. *Avian Dis.* 52:269-77 (2008).
Anwar et al., In silico analysis of genes nucleoprotein, neuraminidase and hemagglutinin: a comparative study on different strains of influenza A (Bird flu) virus sub-type H5N1. *In Silico Biol.* 6:161-8, 2006.
Cameron et al., H9N2 subtype influenza A viruses in poultry in pakistan are closely related to the H9N2 viruses responsible for human infection in Hong Kong. *Virology*, 278:36-41 (2000).
Carter et al., Prepandemic influenza vaccine H5N1 (split virion, inactivated, adjuvanted) [Prepandrix]: a review of its use as an active immunization against influenza A subtype H5N1 virus. *BioDrugs*, 22:279-92, 2008).
Castrucci et al., Attenuation of influenza A virus by insertion of a foreign epitope into the neuraminidase. *J. Virol.* 66: 4647-53 (1992).
Cauthen et al., Continued circulation in China of highly pathogenic avian influenza viruses encoding the hemagglutinin gene associated with the 1997 H5N1 outbreak in poultry and humans. *J Virol.* 74:6592-9 (2000).
Chen et al., Establishment of multiple sublineages of H5N1 influenza virus in Asia: implications for pandemic control. *Proc. Natl. Acad. Sci. USA*, 103:2845-50 (2006).
Couch et al., Safety and immunogenicity of a high dosage trivalent influenza vaccine among elderly subjects. *Vaccine.* 25:7656-63 (2007).
Ehrlich et al., A clinical trial of a whole-virus H5N1 vaccine derived from cell culture. *N. Engl .J. Med.* 358:2573-84 (2008).
Fodor et al., Rescue of influenza A virus from recombinant DNA. *J. Virol.* 73: 9679-82 (1999).

(Continued)

*Primary Examiner* — Stacy B Chen

(74) *Attorney, Agent, or Firm* — DLA Piper LLP (US)

(57) ABSTRACT

The present invention relates, in general, to materials and methods for production of an improved vaccine against influenza virus, wherein the vaccine comprises a reassortant virus having a hemagglutinin gene and a neuraminidase gene from the same influenza A virus subtype or influenza B strain of virus and internal genes from a different influenza A virus subtype or influenza B strain of virus. In one aspect, the HA and NA genes and the internal genes are from a highly pathogenic H5N1 strain of influenza A.

23 Claims, 22 Drawing Sheets

(56) References Cited

FOREIGN PATENT DOCUMENTS

| | | |
|---|---|---|
| WO | WO-2008/021959 A2 | 2/2008 |
| WO | WO-2008/039494 A1 | 4/2008 |

OTHER PUBLICATIONS

Govorkova et al,. Lethality to ferrets of H5N1 influenza viruses isolated from humans and poultry in 2004. *J Virol.* 79(4):2191-8 (2005).
Halder et al., Polymeric coatings that inactivate both influenza virus and pathogenic bacteria. *Proc. Natl. Acad. Sci USA* 103:17667-71 (2006).
Hickman, et al., An avian live attenuated master backbone for potential use in epidemic and pandemic influenza vaccines. *J. Gen. Virol.* 89:2682-90 (2008).
Hoffmann et al., A DNA transfection system for generation of influenza A virus from eight plasmids. *Proc. Natl. Acad. Sci. USA.* 97:6108-13 (2000).
Hoffmann et al., Eight-plasmid system for rapid generation of influenza virus vaccines. *Vaccine*, 20:3165-70 (2002).
Horimoto et al., Pandemic threat posed by avian influence A viruses. *Clin. Microbiol. Rev.* 14(1):129-49 (2001).
Horimoto et al., The development and characterization of H5 influenza virus vaccines derived from a 2003 human isolate. *Vaccine*, 24(17): 3669-76 (2006).
Howard et al., Pre-clinical development of cell culture (Vero)-derived H5N1 pandemic vaccines. *Biol. Chem.* 389(5): 569-77 (2008).
Huber et al., Vaccines against pandemic influenza: what can be done before the next pandemic? *Pediatri. Infect. Dis.* 27(10 Suppl):S113-7 (2008).
Joseph et al., Human infections with avian influenza viruses. *Md Med.* 6:30-2 (2005).
Katz et al., Efficacy of inactivated influenza A virus (H3N2) vaccines grown in mammalian cells or embryonated eggs. *J. Infect. Dis.* 160:191-8 (1989).
Kistner et al., Cell culture (Vero) derived whole virus (H5N1) vaccine based on wild-type virus stain induces cross-protective immune responses. *Vaccine*, 25(32): 6028-36 (2007).
Kistner et al., Development of a mammalian cell (Vero) derived candidate influenza virus vaccine. *Vaccine*, 16:960-8 (1998).
Koopmans et al., Transmission of H7N7 avian influenza A virus to human beings during a large outbreak in commercial poultry farms in the Netherlands. *Lancet*, 363:587-93 (2004).
Krug et al., Are the 5' ends of influenza viral mRNAs synthesized in vivo donated by host mRNAs? *Cell*, 18:329-34 (1979).
Lazarowitz et al., Enhancement of the infectivity of influenza A and B viruses by proteolytic cleavage of the hemagglutinin polypeptide. *Virology*, 68:440-54 (1975).
Lee et al., Characterization of an H5N1 avian influenza virus from Taiwan. *Vet. Microbiol.* 124:193-201 (2007).
Lee et al., Characterization of highly pathogenic H5N1 avian influenza A viruses isolated from South Korea. *J Virol*, 79:3692-702 (2005).
Lee et al., Highly pathogenic avian influenza virus (H5N1) in domestic poultry and relationship with migratory birds, South Korea. *Emerg. Infect. Dis.* 14:487-90 (2008).
Li et al., Recombinant influenza A virus vaccines for the pathogenic human A/Hong Kong/97 (H5N1) viruses. *J. Infect. Dis.* 179:1132-8 (1999).
Liu et al., Generation high yield vaccine strain wholly derived from Avian influenza viruses by reverse genetics. *Chin. J. Biotech.* 22:720-6 (2006).
Londt et al., Highly pathogenic avian influenza viruses with low virulence for chickens in in vivo tests. *Avian Pathol.* 36:347-50 (2007).
Maassab et al., The development of live attenuated cold-adapted influenza virus vaccine for humans. *Rev Med Virol.* 9:237-44 (1999).
Marsh et al., Highly conserved regions of influenza A virus polymerase gene segments are critical for efficient viral RNA packaging. *J. Virol.* 82:2295-304 (2008).
Meisner et al., Infectivity studies of influenza virus hemagglutinin receptor binding site mutants in mice. *J Virol.* 82:5079-83 (2008).
Morein et al., Iscom, a novel structure for antigenic presentation of membrane proteins from enveloped viruses. *Nature*, 308:457-60 (1984).
Neumann et al., Generation of influenza A viruses entirely from cloned cDNAs. *Proc. Natl. Acad. Sci. USA*, 96:9345-50 (1999).
Neumann et al., Genetic engineering of influenza and other negative-strand RNA viruses containing segmented genomes. *Adv. Virus Res.* 53:265-300 (1999).
Nicolson et al., Generation of influenza vaccine viruses on Vero cells by reverse geneticsL A H5N1 candidate vaccine strain produced under a quality system. *Vaccine*, 23(22): 2943-52 (2005).
Oudin, Immunochemical analysis by antigen-antibody precipitation in gels. *Methods Enzymol.* 70:166-98 (1980).
Palese et al., Negative-strand RNA viruses: genetic engineering and applications. *Proc. Natl. Acad. Sci. USA*, 93:11354-58 (1996).
Perdue et al., Virulence-associated sequence duplication at the hemagglutinin cleavage site of avian influenza viruses. *Virus Res.* 49:173-86 (1997).
Pinto et al., Influenza virus M2 protein has ion channel activity. *Cell*, 69:517-28 (1992).
Richardson et al., NS2 protein of influenza virus is found in purified virus and phosphorylated in infected cells. *Arch. Virol.* 116:69-80 (1991).
Robertson et al, High growth reassortant influenza vaccine viruses: new approaches to their control. *Biologicals*, 20:213-20 (1992).
Salomon et al., The polymerase complex genes contribute to the high virulence of the human H5N1 influenza virus isolate A/Vietnam/1203/04. *J. Exp. Med.* 203(3): 689-97 (2006).
Scholtissek et al., Multiplication of influenza A viruses with cleavable and non-cleavable haemagglutinin in chicken embryo membranes or organs, and cell cultures derived therefrom. *J. Gen. Virol.*, 69:2155-64 (1988).
Shan et al., Comparison of nucleic acid-based detection of avian influenza H5N1 with virus isolation. *Biochem. Biophys. Res. Commun.* 302:377-83 (2003).
Shapiro et al., Influenza virus RNA replication in vitro: synthesis of viral template RNAs and virion RNAs in the absence of an added primer. *J. Virol.* 62:2285-90 (1988).
Shi et al., Generation of an attenuated H5N1 avian influenza virus vaccine with all eight genes from avian viruses. *Vaccine*, 25:7379-84 (2007).
Shinya et al., Characterization of a human H5N1 influenza A virus isolated in 2003. *J. Virol.* 79:9926-32 (2005).
Stieneke-Grober et al., Influenza virus hemagglutinin with multibasic cleavage site is activated by furin, a subtilisin-like endoprotease. *EMBO J.* 11:2407-14 (1992).
Subbarao et al., Evaluation of a genetically modified reassortant H5N1 influenza A virus vaccine candidate generated by plasmid-based reverse genetics. *Virology*, 305:192-200 (2003).
Suguitan et al., *PLoS Medicine*, e360:1541-54 (2006).
Swayne, Pathobiology of H5N2 Mexican avian influenza virus infections of chickens. *Vet. Pathol.* 34: 557-67 (1997).
Thomas et al., Thermal inactivation of H5N1 high pathogenicity avian influenza virus in naturally infected chicken meat. *J. Food Prot.* 70: 674-80 (2007).
Tumpey et al., Characterization of a highly pathogenic H5N1 avian influenza A virus isolated from duck meat. *J. Virol.* 76:6344-55 (2002).
Wallis et al., Influenza vaccine prepared by photodynamic inactivation of virus. *J. Immunol.* 91: 677-682 (1963).
Ward et al., Expression and analysis of the NS2 protein of influenza A virus. *Arch. Virol.* 140:2067-73 (1995).
Wood et al., An improved single-radial-immunodiffusion technique for the assay of influenza haemagglutinin antigen: application for potency determinations of inactivated whole virus and subunit vaccines. *J. Biol. Stand.* 5:237-47 (1997).

(56) References Cited

OTHER PUBLICATIONS

Yen et al., Changed in H5N1 influenza virus hemagglutinin receptor binding domain affect systemic spread. *Proc. Natl. Acad. Sci. USA*, 106(1): 286-91 (2009).
Zebedee et al., Influenza A virus M2 protein: monoclonal antibody restriction of virus growth and detection of M2 in virions. *J. Virol.* 62:2762-72 (1988).
Ozaki et al., Generation of high-yielding influenza A viruses in African green monkey kidney (Vero) cells by reverse genetics. *J. Virol.* 78(4): 1851-7 (2004).
Horimoto et al., Strategies for developing vaccines against H5N1 influenza A viruses. *Trends Mol. Med.* 12(11): 506-14 (2006).

* cited by examiner

Figure 1

Nucleotide gene sequences for modified A/Vietnam/1203/04 Strain

NCRs derived from A/Hong Kong/213/03 are underlined.

HA

<u>AGCAAAAGCAGGGGTTCAATCTGTCAAA</u>ATGGAGAAAATAGTGCTTCTTTTTGCAATA
GTCAGTCTTGTTAAAAGTGATCAGATTTGCATTGGTTACCATGCAAACAACTCGACAG
AGCAGGTTGACACAATAATGGAAAAGAACGTTACTGTTACACATGCCCAAGACATACT
GGAAAAGAAACACAACGGGAAGCTCTGCGATCTAGATGGAGTGAAGCCTCTAATTTT
GAGAGATTGTAGCGTAGCTGGATGGCTCCTCGGAAACCCAATGTGTGACGAATTCAT
CAATGTGCCGGAATGGTCTTACATAGTGGAGAAGGCCAATCCAGTCAATGACCTCTG
TTACCCAGGGGATTTCAATGACTATGAAGAATTGAAACACCTATTGAGCAGAATAAAC
CATTTTGAGAAAATTCAGATCATCCCCAAAAGTTCTTGGTCCAGTCATGAAGCCTCAT
TAGGGGTGAGCTCAGCATGTCCATACCAGGGAAAGTCCTCCTTTTTCAGAAATGTGG
TATGGCTTATCAAAAGAACAGTACATACCCAACAATAAAGAGGAGCTACAATAATAC
CAACCAAGAAGATCTTTTGGTACTGTGGGGGATTCACCATCCTAATGATGCGGCAGA
GCAGACAAAGCTCTATCAAAACCCAACCACCTATATTTCCGTTGGGACATCAACACTA
AACCAGAGATTGGTACCAAGAATAGCTACTAGATCCAAAGTAAACGGGCAAAATGGA
AGGATGGAGTTCTTCTGGACAATTTTAAAGCCGAATGATGCAATCAACTTCGAGAGTA
ATGGAAATTTCATTGCTCCAGAATATGCATACAAAATTGTCAAGAAAGGGGACTCAAC
AATTATGAAAAGTGAATTGGAATATGGTAACTGCAACACCAAGTGTCAAACTCCAATG
GGGGCGATAAACTCTAGCATGCCATTCCACAATATACACCCTCTCACCATTGGGGAA
TGCCCCAAATATGTGAAATCAAACAGATTAGTCCTTGCGACTGGGCTCAGAAATAGC
CCTCAAACCGAGACCCGAGGATTATTTGGAGCTATAGCAGGTTTTATAGAGGGAGGA
TGGCAGGGAATGGTAGATGGTTGGTATGGGTACCACCATAGCAATGAGCAGGGGAG
TGGGTACGCTGCAGACAAAGAATCCACTCAAAAGGCAATAGATGGAGTCACCAATAA
GGTCAACTCGATCATTGACAAAATGAACACTCAGTTTGAGGCCGTTGGAAGGGAATT
TAACAACTTAGAAAGGAGAATAGAGAATTTAAACAAGAAGATGGAAGACGGGTTCCT
AGATGTCTGGACTTATAATGCTGAACTTCTGGTTCTCATGGAAAATGAGAGAACTCTA
GACTTTCATGACTCAAATGTCAAGAACCTTTACGACAAGGTCCGACTACAGCTTAGG
GATAATGCAAAGGAGCTGGGTAACGGTTGTTTCGAGTTCTATCATAAATGTGATAATG
AATGTATGGAAAGTGTAAGAAATGGAACGTATGACTACCCGCAGTATTCAGAAGAAG
CGAGACTAAAAAGAGAGGAAATAAGTGGAGTAAAATTGGAATCAATAGGAATTTACCA
AATACTGTCAATTTATTCTACAGTGGCGAGTTCCCTAGCACTGGCAATCATGGTAGCT
GGTCTATCCTTATGGATGTGCTCCAATGGATCGTTACAATGCAGAATTTGCATTTA<u>AA
TTTGTGAGTTCAGATTGTAGTTAAAAACACCCTTGTTTCTACT</u> (SEQ ID NO: 1)

NA

<u>AGCAAAAGCAGGAGTTCAAA</u>ATGAATCCAAATCAGAAGATAATAACCATCGGATCAAT
CTGTATGGTAACTGGAATAGTTAGCTTAATGTTACAAATTGGGAACATGATCTCAATA
TGGGTCAGTCATTCAATTCACACAGGGAATCAACACCAATCTGAACCAATCAGCAATA
CTAATTTTCTTACTGAGAAAGCTGTGGCTTCAGTAAAATTAGCGGGCAATTCATCTCT
TTGCCCCATTAACGGATGGGCTGTATACAGTAAGGACAACAGTATAAGGATCGGTTC
CAAGGGGGATGTGTTTGTTATAAGAGAGCCGTTCATCTCATGCTCCCACTTGGAATG
CAGAACTTTCTTTTTGACTCAGGGAGCCTTGCTGAATGACAAGCACTCCAATGGGAC
TGTCAAAGACAGAAGCCCTCACAGAACATTAATGAGTTGTCCTGTGGGTGAGGCTCC
CTCCCCATATAACTCAAGGTTTGAGTCTGTTGCTTGGTCAGCAAGTGCTTGCCATGAT
GGCACCAGTTGGTTGACGATTGGAATTTCTGGCCCAGACAATGGGGCTGTGGCTGT
ATTGAAATACAATGGCATAATAACAGACACTATCAAGAGTTGGAGGAACAACATACTG
AGAACTCAAGAGTCTGAATGTGCATGTGTAAATGGCTCTTGCTTTACTGTAATGACTG
ACGGACCAAGTAATGGTCAGGCATCACATAAGATCTTCAAAATGGAAAAAGGGAAAG
TGGTTAAATCAGTCGAATTGGATGCTCCTAATTATCACTATGAGGAATGCTCCTGTTA
TCCTAATGCCGGAGAAATCACATGTGTGTGCAGGGATAATTGGCATGGCTCAAATCG
GCCATGGGTATCTTTCAATCAAAATTTGGAGTATCAAATAGGATATATATGCAGTGGA
GTTTTCGGAGACAATCCACGCCCCAATGATGGAACAGGTAGTTGTGGTCCGGTGTCC
TCTAACGGGGCATATGGGGTAAAAGGGTTTTCATTTAAATACGGCAATGGTGTCTGG
ATCGGGAGAACCAAAAGCACTAATTCCAGGAGCGGCTTTGAAATGATTTGGGATCCA

AATGGGTGGACTGAAACGGACAGTAGCTTTTCAGTGAAACAAGATATCGTAGCAATA
ACTGATTGGTCAGGATATAGCGGGAGTTTTGTCCAGCATCCAGAACTGACAGGACTA
GATTGCATAAGACCTTGTTTCTGGGTTGAGTTGATCAGAGGGCGGCCCAAAGAGAGC
ACAATTTGGACTAGTGGGAGCAGCATATCTTTTTGTGGTGTAAATAGTGACACTGTGG
GTTGGTCTTGGCCAGACGGTGCCGAGTTGCCATTCACCATTGACAAGTAG<u>TTTGTTC
AAAAAACTCCTTGTTTCTACT</u> (SEQ ID NO: 2)

M
<u>AGCAAAAGCAGGTAGATGTTGAAAG</u>ATGAGTCTTCTAACCGAGGTCGAAACGTACGT
TCTCTCTATCATCCCGTCAGGCCCCCTCAAAGCCGAGATCGCACAGAAACTTGAAGA
TGTCTTTGCAGGAAAGAACACCGATCTCGAGGCTCTCATGGAGTGGCTAAAGACAAG
ACCAATCCTGTCACCTCTGACTAAAGGGATTTTGGGATTTGTATTCACGCTCACCGTG
CCCAGTGAGCGAGGACTGCAGCGTAGACGCTTTGTCCAGAATGCCCTAAATGGAAA
TGGAGATCCAAATAATATGGATAGGGCAGTTAAGCTATATAAGAAGCTGAAAAGAGA
ATAACATTCCATGGGCTAAGGAGGTCGCACTCAGCTACTCAACCGGTGCACTTGC
CAGTTGCATGGGTCTCATATACAACAGGATGGGAACGGTGACTACGGAAGTGGCTTT
TGGCCTAGTGTGTGCCACTTGTGAGCAGATTGCAGATTCACAGCATCGGTCTCACAG
ACAGATGGCAACTATCACCAACCCACTAATCAGACATGAGAACAGAATGGTGCTGGC
CAGCACTACAGCTAAGGCTATGGAGCAGATGGCGGGATCAAGTGAGCAGGCAGCG
GAAGCCATGGAGATCGCTAATCAGGCTAGGCAGATGGTGCAGGCAATGAGGACAAT
TGGGACTCATCCTAACTCTAGTGCTGGTCTGAGAGATAATCTTCTTGAAAATTTGCAG
GCCTACCAGAAACGAATGGGAGTGCAGATGCAGCGATTCAAGTGATCCTATTGTTGT
TGCCGCAAATATCATTGGGATCTTGCACTTGATATTGTGGATTCTTGATCGTCTTTTCT
TCAAATGCATTTATCGTCGCCTTAAATACGGTTTGAAAAGAGGGCCTGCTACGGCAG
GGGTACCTGAGTCTATGAGGGAAGAGTACCGGCAGGAACAGCAGAGTGCTGTGGAT
GTTGACGATGGTCATTTTGTCAACATAGAATTGGAGTA<u>AAAAAACTACCTTGTTTCTACT</u>
(SEQ ID NO: 3)

NS
<u>AGCAAAAGCAGGGTGACAAAAACATAATG</u>GATTCCAACACTGTGTCAAGCTTTCAGG
TAGACTGCTTTCTTTGGCATGTCCGCAAACGATTTGCAGACCAAGAACTGGGTGATG
CCCCATTCCTTGACCGGCTTCGCCGAGATCAGAAGTCCCTAAGAGGAAGAGGCAAC
ACTCTTGGTCTGGACATCGAAACAGCTACTCGCGCAGGAAAGCAGATAGTGGAGCG
GATTCTGGAGGGGGAGTCTGATAAGGCACTTAAAATGCCGGCTTCACGCTACCTAAC
TGACATGACTCTCGAAGAAATGTCAAGGGACTGGTTCATGCTCATGCCCAAGCAGAA
AGTGGCAGGTTCCCTTTGCATCAAAATGGACCAGGCAATAATGGATAAAACCATCAT
ATTGAAAGCAAACTTCAGTGTGATTTTTGACCGGTTGGAAACCCTAATACTACTTAGA
GCTTTCACAGAAGAAGGAGCAATCGTGGGAGAAATCTCACCATTACCTTCTCTTCCA
GGACATACTGGTGAGGATGTCAAAAATGCAATTGGCGTCCTCATCGGAGGACTTGAA
TGGAATGATAACACAGTTCGAGTCACTGAAACTATACAGAGATTCGCTTGGAGAAAC
AGTGATGAGGATGGGAGACTTCCACTCCCTCCAAATCAGAAACGGTAAATGGCGAGA
ACAATTGAGTCAGAAGTTTGAAGAAATAAGGTGGCTGATTGAAGAAGTAAGACATAG
ATTGAAAATTACAGAAAACAGCTTCGAACAGATAACGTTTATGCAAGCCTTACAACTA
CTGCTTGAAGTGGAGCAAGAGATAAGAGCCTTCTCGTTTCAGCTTATTT<u>AATGATAAA
AAACACCCTTGTTTCTACT</u> (SEQ ID NO: 4)

NP
<u>AGCAAAAGCAGGGTAGATAATCACTCACCGAGTGACATCAGCATCATG</u>GCGTCTCAA
GGCACCAAACGATCTTATGAACAGATGGAAACTGGTGGGAACGCCAGAATGCTACT
GAGATCAGGGCATCTGTTGGAAGAATGGTTAGTGGCATTGGGAGGTTCTACATACAG
ATGTGCACAGAACTCAAACTCAGTGACTATGAAGGGAGGCTGATCCAGAACAGCATA
ACAATAGAGAGAATGGTACTCTCTGCATTTGATGAAAGAAGGAACAGATACCTGGAA
GAACACCCCAGTGCGGGAAAGGACCCGAAGAAGACTGGAGGTCCAATTTATCGGAG
GAGAGACGGGAAATGGGTGAGAGAGCTAATTCTGTACGACAAAGAGGAGATCAGGA
GGATTTGGCGTCAAGCGAACAATGGAGAGGACGCAACTGCTGGTCTTACCCACCTG
ATGATATGGCATTCCAATCTAAATGATGCCACATATCAGAGAACGAGAGCTCTCGTG
CGTACTGGAATGGACCCAAGGATGTGCTCTCTGATGCAAGGGTCAACTCTCCCGAG

GAGATCTGGAGCTGCCGGTGCAGCAGTAAAGGGGGTAGGGACAATGGTGATGGAG
CTGATTCGGATGATAAAACGAGGGATCAACGACCGGAATTTCTGGAGAGGCGAAAAT
GGAAGAAGAACAAGGATTGCATATGAGAGAATGTGCAACATCCTCAAAGGGAAATTC
CAAACAGCAGCACAAAGAGCAATGATGGATCAAGTGCGAGAGAGCAGAAATCCTGG
GAATGCTGAAATTGAAGATCTCATTTTTCTGGCACGGTCTGCACTCATCCTGAGAGG
ATCAGTGGCCCATAAGTCCTGCTTGCCTGCTTGTGTGTACGGACTTGCAGTGGCCAG
TGGATATGACTTTGAGAGAGAAGGGTACTCTCTGGTTGGAATAGATCCTTTCCGCCT
GCTTCAAAACAGCCAGGTCTTTAGTCTCATTAGACCAAATGAGAATCCAGCACATAAG
AGTCAATTAGTGTGGATGGCATGCCACTCTGCAGCATTTGAGGACCTTAGAGTCTCA
AGTTTCATCAGAGGGACAAGAGTGGTCCCAAGAGGACAGCTATCCACCAGAGGGGT
TCAAATTGCTTCAAATGAGAACATGGAGGCAATGGACTCCAACACTCTTGAACTGAG
AAGCAGATATTGGGCTATAAGAACCAGAAGCGGAGGAAACACCAACCAGCAGAGGG
CATCTGCAGGACAGATCAGCGTTCAGCCCACTTTCTCGGTCCAGAGAAACCTTCCCT
TCGAAAGAGCGACCATTATGGCAGCATTTACAGGAAATACTGAGGGCAGAACGTCTG
ACATGAGGACTGAAATCATAAGAATGATGGAAAGTGCCAGACCAGAAGATGTGTCAT
TCCAGGGGCGGGGAGTCTTCGAGCTCTCGGACGAAAAGGCAACGAACCCGATCGT
GCCTTCCTTTGACATGAATAATGAAGGATCTTATTTCTTCGGAGACAATGCAGAGGAG
TATGACAATTAAAGAAAAATACCCTTGTTTCTACT (SEQ ID NO: 5)

PA
AGCGAAAGCAGGTACTGATCCAAAATGGAAGACTTTGTGCGACAATGCTTCAATCCA
ATGATTGTCGAGCTTGCGGAAAAGGCAATGAAAGAATATGGGGAAGATCCGAAAATC
GAAACGAACAAGTTTGCTGCAATATGCACACACTTGGAGGTCTGTTTCATGTATTCGG
ATTTTCACTTTATTGATGAACGGAGTGAATCAATAATTGTAGAATCTGGAGATCCGAA
TGCATTATTGAAACACCGATTTGAAATAATTGAAGGAAGAGACCGAACGATGGCCTG
GACTGTGGTGAATAGTATCTGCAACACCACAGGAGTTGAGAAACCTAAATTTCTCCC
AGATTTGTATGACTACAAAGAGAACCGATTCATCGAAATTGGAGTGACACGGAGGGA
AGTTCATACATACTATCTGGAGAAAGCCAACAAGATAAAATCCGAGGAGACACATATT
CACATATTCTCATTCACAGGGGAGGAAATGGCCACCAAAGCGGACTACACCCTTGAT
GAAGAGAGCAGGGCAAGAATTAAAACCAGGCTGTTCACCATAAGGCAGGAAATGGC
CAGTAGGGGTCTATGGGATTCCTTTCGTCAATCCGAGAGAGGCGAAGAGACAATTGA
AGAAAAATTTGAAATCACTGGAACCATGCGCAGACTTGCAGACCAAAGTCTCCCACC
GAACTTCTCCAGCCTTGAAAACTTTAGAGCCTATGTGGATGGATTCGAACCGAACGG
CTGCATTGAGGGCAAGCTTTCTCAAATGTCAAAAGAAGTGAATGCTAGAATTGAGCC
ATTTTTGAAGACAACGCCACGCCCTCTCAGACTACCTGATGGGCCTCCTTGCTCTCA
GCGGTCGAAGTTCTTGCTGATGGATGCCCTTAAATTAAGCATCGAAGACCCGAGTCA
TGAGGGGGAGGGGATACCACTATACGATGCAATCAAATGCATGAAGACATTTTCGG
CTGGAAAGAGCCCAACATCGTGAAACCACATGAAAAGGTATAAACCCCAATTACCT
CCTGGCTTGGAAGCAAGTGCTGGCAGAACTCCAAGATATTGAAAATGAGGAGAAAAT
CCCAAAAACAAAGAACATGAAAAAAACAAGCCAGTTGAAGTGGGCACTCGGTGAGAA
CATGGCACCAGAGAAAGTAGACTTTGAGGACTGCAAAGATGTTAGCGATCTAAGACA
GTATGACAGTGATGAACCAGAGTCTAGATCACTAGCAAGCTGGATTCAGAGTGAATT
CAACAAGGCATGTGAATTGACAGATTCGATTTGGATTGAACTCGATGAAATAGGAGA
AGACGTAGCTCCAATTGAGCACATTGCAAGTATGAGAAGGAACTATTTTACAGCGGA
AGTATCCCATTGCAGGGCCACTGAATACATAATGAAGGGAGTGTACATAAACACAGC
CCTGTTGAATGCATCCTGTGCAGCCATGGATGACTTTCAACTGATTCCAATGATAAGC
AAATGCAGAACCAAAGAAGGAAGACGGAAAACTAATCTGTATGGATTCATTATAAAG
GGAGATCCCACTTGAGGAATGATACCGATGTGGTAAATTTTGTGAGTATGGAATTCTC
TCTTACTGATCCGAGGCTGGAGCCACACAAGTGGGAAAAGTACTGTGTCCTCGAGAT
AGGAGACATGCTCCTCCGGACTGCAGTAGGCCAAGTTTCGAGGCCCATGTTCCTGT
ATGTAAGAACCAATGGAACCTCCAAGATCAAAATGAAATGGGCATGGAAATGAGGC
GATGCCTTCTTCAATCCCTTCAACAAATTGAAAGCATGATTGAAGCCGAGTCTTCTGT
CAAAGAGAAGGACATGACCAAAGAATTCTTTGAAAACAAATCAGAAACATGGCCGATT
GGAGAGTCCCCCAAGGGAGTGGAGGAAGGCTCCATCGGAAAGGTGTGCAGAACCTT
GCTGGCGAAGTCTGTGTTCAACAGTTTATATGCATCTCCACAACTCGAGGGGTTTTC
AGCTGAATCAAGAAAATTGCTTCTCATTGCTCAGGCACTTAGGGACAACCTGGAACC

Figure 1 (cont'd)

TGGGACCTTCGATCTTGGAGGGCTATATGAAGCAATTGAGGAGTGCCTGATTAACGA
TCCCTGGGTTTTGCTTAATGCGTCTTGGTTCAACTCCTTCCTCGCACATGCACTGAAA
TAGTTGTGGCAATGCTACTATTTGCTATCCATACTGTCCAAAAAGTACCTTGTTTCTA
CT (SEQ ID NO: 6)

PB1
AGCGAAAGCAGGCAAACCATTTGAATGGATGTCAATCCGACTTTACTTTTCTTGAAAG
TACCAGTGCAAAATGCTATAAGTACCACCTTCCCTTATACTGGAGACCCTCCATACAG
CCATGGAACAGGGACAGGATACACCATGGACACAGTCAACAGAACACACCAATATTC
AGAAAAGGGGAAGTGGACAACAAACACAGAGACTGGAGCACCCCAACTCAACCCGA
TTGATGGACCACTACCTGAGGATAATGAGCCCAGTGGGTACGCACAAACAGATTGTG
TATTGGAAGCAATGGCTTTCCTTGAAGAATCCCACCCAGGGATCTTTGAAAACTCGT
GTCTTGAAACGATGGAAATTGTTCAACAAACAAGAGTGGATAAACTGACCCAAGGTC
GCCAGACCTATGACTGGACATTGAATAGAAACCAACCGGCTGCAACTGCTTTGGCCA
ACACTATAGAAATCTTCAGATCGAACGGTCTAACAGCCAATGAATCGGGACGGCTAA
TAGATTTCCTCAAGGATGTGATGGAGTCAATGGATAAGGAAGAAATGGAGATAACAA
CACATTTCCAGAGAAAGAGAAGGGTGAGGGACAACATGACCAAGAAAATGGTCACAC
AAAGAACAATAGGGAAGAAAAAACAAAGGCTGAACAAAAAGAGCTACCTGATAAGAG
CACTGACACTGAACACAATGACAAAAGATGCAGAAAGAGGCAAATTGAAGAGGCGAG
CGATTGCAACACCCGGAATGCAAATCAGAGGATTCGTGTACTTTGTTGAAACACTAG
CGAGGAGTATCTGTGAGAAACTTGAGCAATCTGGACTCCCAGTCGGAGGGAATGAG
AAGAAGGCTAAATTGGCAAACGTCGTGAGGAAGATGATGACTAACTCACAAGATACT
GAACTCTCCTTTACAATTACTGGAGACAATACCAAATGGAATGAGAATCAGAATCCTA
GGATGTTTCTGGCAATGATAACGTACATCACAAGGAACCAGCCAGAATGGTTTCGGA
ATGTCTTAAGCATAGCTCCTATAATGTTCTCAAACAAAATGGCGAGACTAGGAAAAGG
ATACATGTTCGAAAGTAAGAGCATGAAGTTACGAACACAAATACCAGCAGAAATGCTT
GCAAACATTGATCTTAAATACTTCAATGAATTAACGAAAAAGAAAATTGAGAAAATAAG
GCCTCTATTAATAGATGGTACAGCCTCATTGAGCCCTGGAATGATGATGGGCATGTT
CAACATGCTGAGTACAGTCCTAGGAGTTTCAATCCTGAATCTTGGACAGAAAAGGTA
CACCAAAACCACATATTGGTGGGACGGACTCCAATCCTCTGATGATTTCGCTCTCAT
CGTAAATGCACCGAATCATGAGGGAATACAAGCAGGAGTGGATAGGTTTTATAGGAC
TTGTAAACTAGTTGGAATCAATATGAGCAAGAAGAAGTCTTACATAAATCGGACAGGG
ACATTTGAATTCACGAGCTTTTTCTACCGCTATGGATTTGTAGCCAATTTCAGTATGG
AGCTGCCCAGTTTTGGAGTGTCTGGAATTAATGAATCGGCCGACATGAGCATTGGTG
TTACAGTGATAAAAAACAATATGATAAACAACGACCTTGGGCCAGCAACAGCTCAGAT
GGCTCTTCAGTTATTCATCAAGGACTACAGATACACATACCGATGCCACAGAGGGGA
TACGCAAATCCAAACAAGGAGATCATTCGAGCTGAAGAAGCTGTGGGAGCAAACCC
GTTCAAAGGCAGGACTGTTGGTTTCAGATGGAGGACCAAATCTATACAATATCCGAA
ACCTCCATATTCCTGAAGTCTGCTTAAAATGGGAATTGATGGATGAAGATTACCAGGG
CAGACTGTGTAATCCTCTGAATCCATTCGTCAGCCATAAGGAAATTGAATCTGTCAAC
AATGCTGTAGTAATGCCAGCTCATGGCCCGGCCAAGAGTATGGAATATGATGCCGTT
GCAACTACACATTCATGGATTCCTAAAAGGAACCGTTCCATTCTCAATACGAGTCAAA
GGGGAATTCTTGAGGATGAACAGATGTACCAGAAGTGCTGCAATCTATTCGAGAAAT
TCTTCCCCAGCAGTTCATATCGGAGGCCAGTTGGAATTTCCAGCATGGTGGAGGCCA
TGGTGTCTAGGGCCCGAATTGACGCACGAATCGATTTCGAGTCTGGAAGGATTAAGA
AAGAAGAGTTTGCCGAGATCATGAAGATCTGTTCCACCATTGAAGAACTCAGACGGC
AAAAATAGTGAATTTAGCTTGTCCTTCGTGAAAAAATGCCTTGTTTCTACT (SEQ ID NO: 7)

PB2
AGCGAAAGCAGGTCAAATATATTCAATATGGAGAGGATAAAAGAATTACGAGATCTAA
TGTCACAGTCCCGCACTCGCGAGATACTAACAAAAACCACTGTGGACCATATGGCCA
TAATCAAGAAATACACATCAGGAAGACAAGAGAAGAACCCTGCTCTCAGAATGAAAT
GGATGATGGCAATGAAATATCCAATCACAGCGGACAAGAGAATAATAGAGATGATTC
CTGAAAGGAATGAACAAGGGCAGACGCTCTGGAGCAAGACAAATGATGCTGGATCG
GACAGGGTGATGGTGTCTCCCCTAGCTGTAACTTGGTGGAATAGGAATGGGCCGGC

Figure 1 (cont'd)

```
GACAAGTGCAGTTCATTATCCAAAGGTTTACAAAACATACTTTGAGAAGGTTGAAAGA
TTAAAACATGGAACCTTCGGTCCCGTTCATTTCCGAAACCAGGTTAAAATACGCCGC
CGAGTTGATATAAATCCTGGCCATGCAGATCTCAGTGCTAAAGAAGCACAAGATGTC
ATCATGGAGGTCGTTTTCCCAAATGAAGTGGGAGCTAGAATATTGACATCAGAGTCG
CAATTGACAATAACGAAAGAGAAGAAAGAAGAGCTCCAAGATTGTAAGATTGCTCCC
TTAATGGTTGCATACATGTTGGAAAGGGAACTGGTCCGCAAGACCAGATTCCTACCG
GTAGCAGGCGGAACAAGTAGTGTGTACATTGAGGTATTGCATTTGACTCAAGGGACC
TGCTGGGAACAGATGTACACTCCAGGCGGAGAAGTGAGAAATGACGATGTTGACCA
GAGTTTGATCATTGCTGCCAGAAACATTGTTAGGAGAGCAACAGTATCAGCGGATCC
ACTGGCATCACTGCTGGAGATGTGTCACAGCACACAAATTGGTGGGATAAGGATGGT
GGACATCCTTAGGCAAAATCCAACTGAGGAACAAGCTGTGGATATATGCAAAGCAGC
AATGGGTCTTAGGATCAGTTCTTCCTTTAGCTTTGGAGGCTTCACTTTCAAAAGAACA
AGTGGATCATCCGTCAAGAAGGAAGAGGAAGTGCTTACAGGCAACCTCCAAACATTG
AAAATAAGAGTACATGAGGGGTATGAGGAATTCACAATGGTTGGGCGGAGGGCAAC
AGCTATCCTGAGGAAAGCAACTAGAAGGCTGATTCAGTTGATAGTAAGTGGAAGAGA
CCAACAATCAATCGCTGAGGCAATCATTGTAGCAATGGTGTTCTCACAGGAGGATTG
CATGATAAAGGCAGTCCGAGGCGATCTGAATTTCGTAAACAGAGCAAACCAAAGATT
AAACCCCATGCATCAACTCCTGAGACATTTTCAAAAGGACGCAAAAGTGCTATTTCAG
AATTGGGGAATTGAACCCATTGATAATGTCATGGGGATGATCGGAATATTACCTGACA
TGACTCCCAGCACAGAAATGTCACTGAGAGGAGTAAGAGTTAGTAAAATGGGAGTGG
ATGAATATTCCAGCACTGAGAGAGTAGTTGTAAGTATTGACCGTTTCTTAAGGGTTCG
AGATCAGCGGGGAACGTACTCTTATCTCCCGAAGAGGTCAGCGAAACCCAGGGAA
CAGAGAAATTGACAATAACATATTCATCATCAATGATGTGGGAAATCAACGGTCCTGA
GTCAGTGCTTGTTAACACCTATCAGTGGATCATCAGAAACTGGGAGACTGTGAAGAT
TCAATGGTCTCAAGACCCCACGATGCTGTACAATAAGATGGAGTTTGAACCGTTCCA
ATCCTTGGTACCCAAAGCTGCCAGAGGTCAATACAGTGGATTTGTGAGAACATTATTC
CAGCAAATGCGTGACGTACTGGGGACATTTGATACTGTCCAGATAATAAAGCTGCTA
CCATTTGCAGCAGCCCCACCGAAGCAGAGCAGAATGCAGTTTTCTTCTCTAACTGTG
AATGTGAGAGGCTCAGGAATGAGAATACTCGTAAGGGCAATTCCCCTGTGTTCAAC
TACAATAAGGCAACCAAAAGGCTTACCGTCCTTGGAAAGGACGCAGGTGCATTAACA
GAGGATCCGGATGAAGGGACAGCCGGAGTGGAGTCTGCAGTACTGAGGGGATTCTT
AATTTTAGGCAAGGAGGACAAAAGGTATGGACCAGCATTGAGCATCAATGAACTGAG
CAATCTTGCGAAGGGGGAGAAAGCTAATGTGCTGATAGGGCAAGGTGACGTGGTGT
TGGTAATGAAACGAAAACGGGACTCTAGCATACTTACTGACAGCCAGACAGCGACCA
AAAGAATTCGGATGGCCATCAATTAGTGTCGAATTGTTTAAAAACGACCTTGTTTCTA
CT (SEQ ID NO: 8)
```

Figure 1 (cont'd)

FIGURE 2
Indonesia Strain Gene Sequences

HA

AGCAAAAGCAGGGGTTCAATCTGTCAAAATGGAGAAAATAGTGCTTCTTTTTGCAATA
GTCAGTCTTGTTAAAAGTGATCAGATTTGCATTGGTTACCATGCAAACAACTCGACAG
AGCAGGTTGACACAATAATGGAAAAGAACGTTACTGTTACACATGCCCAAGACATACT
GGAAAAGAAACACAACGGGAAGCTCTGCGATCTAGATGGAGTGAAGCCTCTAATTTT
GAGAGATTGTAGCGTAGCTGGATGGCTCCTCGGAAACCCAATGTGTGACGAATTCAT
CAATGTGCCGGAATGGTCTTACATAGTGGAGAAGGCCAATCCAGTCAATGACCTCTG
TTACCCAGGGGATTTCAATGACTATGAAGAATTGAAACACCTATTGAGCAGAATAAAC
CATTTTGAGAAAATTCAGATCATCCCCAAAAGTTCTTGGTCCAGTCATGAAGCCTCAT
TAGGGGTGAGCTCAGCATGTCCATACCAGGGAAAGTCCTCCTTTTTCAGAAATGTGG
TATGGCTTATCAAAAAGAACAGTACATACCCAACAATAAAGAGGAGCTACAATAATAC
CAACCAAGAAGATCTTTTGGTACTGTGGGGGATTCACCATCCTAATGATGCGGCAGA
GCAGACAAAGCTCTATCAAAACCCAACCACCTATATTTCCGTTGGGACATCAACACTA
AACCAGAGATTGGTACCAAGAATAGCTACTAGATCCAAAGTAAACGGGCAAAATGGA
AGGATGGAGTTCTTCTGGACAATTTTAAAGCCGAATGATGCAATCAACTTCGAGAGTA
ATGGAAATTTCATTGCTCCAGAATATGCATACAAAATTGTCAAGAAAGGGGACTCAAC
AATTATGAAAAGTGAATTGGAATATGGTAACTGCAACACCAAGTGTCAAACTCCAATG
GGGGCGATAAACTCTAGCATGCCATTCCACAATATACACCCTCTCACCATTGGGGAA
TGCCCCAAATATGTGAAATCAAACAGATTAGTCCTTGCGACTGGGCTCAGAAATAGC
CCTCAAACCGAGACCCGAGGATTATTTGGAGCTATAGCAGGTTTTATAGAGGGAGGA
TGGCAGGGAATGGTAGATGGTTGGTATGGGTACCACCATAGCAATGAGCAGGGGAG
TGGGTACGCTGCAGACAAAGAATCCACTCAAAAGGCAATAGATGGAGTCACCAATAA
GGTCAACTCGATCATTGACAAAATGAACACTCAGTTTGAGGCCGTTGGAAGGGAATT
TAACAACTTAGAAAGGAGAATAGAGAATTTAAACAAGAAGATGGAAGACGGGTTCCT
AGATGTCTGGACTTATAATGCTGAACTTCTGGTTCTCATGGAAAATGAGAGAACTCTA
GACTTTCATGACTCAAATGTCAAGAACCTTTACGACAAGGTCCGACTACAGCTTAGG
GATAATGCAAAGGAGCTGGGTAACGGTTGTTTCGAGTTCTATCATAAATGTGATAATG
AATGTATGGAAAGTGTAAGAAATGGAACGTATGACTACCCGCAGTATTCAGAAGAAG
CGAGACTAAAAAGAGAGGAAATAAGTGGAGTAAAATTGGAATCAATAGGAATTTACCA
AATACTGTCAATTTATTCTACAGTGGCGAGTTCCCTAGCACTGGCAATCATGGTAGCT
GGTCTATCCTTATGGATGTGCTCCAATGGATCGTTACAATGCAGAATTTGCATTTAAA
TTTGTGAGTTCAGATTGTAGTTAAAAACACCCTTGTTTCTACT (SEQ ID NO: 1)

NA

AGCAAAAGCAGGAGTTCAAAATGAATCCAAATCAGAAGATAATAACCATCGGATCAAT
CTGTATGGTAACTGGAATAGTTAGCTTAATGTTACAAATTGGGAACATGATCTCAATA
TGGGTCAGTCATTCAATTCACACAGGGAATCAACACCAATCTGAACCAATCAGCAATA
CTAATTTTCTTACTGAGAAAGCTGTGGCTTCAGTAAAATTAGCGGCAATTCATCTCT
TTGCCCCATTAACGGATGGGCTGTATACAGTAAGGACAACAGTATAAGGATCGGTTC
CAAGGGGGATGTGTTTGTTATAAGAGAGCCGTTCATCTCATGCTCCCACTTGGAATG
CAGAACTTTCTTTTTGACTCAGGGAGCCTTGCTGAATGACAAGCACTCCAATGGGAC
TGTCAAAGACAGAAGCCCTCACAGAACATTAATGAGTTGTCCTGTGGGTGAGGCTCC
CTCCCCATATAACTCAAGGTTTGAGTCTGTTGCTTGGTCAGCAAGTGCTTGCCATGAT
GGCACCAGTTGGTTGACGATTGGAATTTCTGGCCCAGACAATGGGCTGTGGCTGT
ATTGAAATACAATGGCATAATAACAGACACTATCAAGAGTTGGAGGAACAACATACTG
AGAACTCAAGAGTCTGAATGTGCATGTGTAAATGGCTCTTGCTTTACTGTAATGACTG
ACGGACCAAGTAATGGTCAGGCATCACATAAGATCTTCAAAATGGAAAAAGGGAAAG
TGGTTAAATCAGTCGAATTGGATGCTCCTAATTATCACTATGAGGAATGCTCCTGTTA
TCCTAATGCCGGAGAAATCACATGTGTGTGCAGGGATAATTGGCATGGCTCAAATCG
GCCATGGGTATCTTTCAATCAAAATTTGGAGTATCAAATAGGATATATATGCAGTGGA
GTTTTCGGAGACAATCCACGCCCCAATGATGGAACAGGTAGTTGTGGTCCGGTGTCC
TCTAACGGGGCATATGGGGTAAAAGGGTTTTCATTTAAATACGGCAATGGTGTCTGG
ATCGGGAGAACCAAAAGCACTAATTCCAGGAGCGGCTTTGAAATGATTTGGGATCCA
AATGGGTGGACTGAAACGGACAGTAGCTTTTCAGTGAAACAAGATATCGTAGCAATA
ACTGATTGGTCAGGATATAGCGGGAGTTTTGTCCAGCATCCAGAACTGACAGGACTA
GATTGCATAAGACCTTGTTTCTGGGTTGAGTTGATCAGAGGGCGGCCCAAAGAGAGC
ACAATTTGGACTAGTGGGAGCAGCATATCTTTTTGTGGTGTAAATAGTGACACTGTGG

GTTGGTCTTGGCCAGACGGTGCCGAGTTGCCATTCACCATTGACAAGTAGTTTGTTC
AAAAAACTCCTTGTTTCTACT (SEQ ID NO: 2)

M
AGCAAAAGCAGGTAGATGTTGAAAGATGAGTCTTCTAACCGAGGTCGAAACGTACGT
TCTCTCTATCATCCCGTCAGGCCCCCTCAAAGCCGAGATCGCACAGAAACTTGAAGA
TGTCTTTGCAGGAAAGAACACCGATCTCGAGGCTCTCATGGAGTGGCTAAAGACAAG
ACCAATCCTGTCACCTCTGACTAAAGGGATTTTGGGATTTGTATTCACGCTCACCGTG
CCCAGTGAGCGAGGACTGCAGCGTAGACGCTTTGTCCAGAATGCCCTAAATGGAAA
TGGAGATCCAAATAATATGGATAGGGCAGTTAAGCTATATAAGAAGCTGAAAAGAGA
AATAACATTCCATGGGGCTAAGGAGGTCGCACTCAGCTACTCAACCGGTGCACTTGC
CAGTTGCATGGGTCTCATATACAACAGGATGGGAACGGTGACTACGGAAGTGGCTTT
TGGCCTAGTGTGTGCCACTTGTGAGCAGATTGCAGATTCACAGCATCGGTCTCACAG
ACAGATGGCAACTATCACCAACCCACTAATCAGACATGAGAACAGAATGGTGCTGGC
CAGCCACTACAGCTAAGGCTATGGAGCAGATGGCGGGATCAAGTGAGCAGGCAGCG
GAAGCCATGGAGATCGCTAATCAGGCTAGGCAGATGGTGCAGGCAATGAGGACAAT
TGGGACTCATCCTAACTCTAGTGCTGGTCTGAGAGATAATCTTCTTGAAAATTTGCAG
GCCTACCAGAAACGAATGGGAGTGCAGATGCAGCGATTCAAGTGATCCTATTGTTGT
TGCCGCAAATATCATTGGGATCTTGCACTTGATATTGTGGATTCTTGATCGTCTTTTCT
TCAAATGCATTTATCGTCGCCTTAAATACGGTTTGAAAAGAGGGCCTGCTACGGCAG
GGGTACCTGAGTCTATGAGGGAAGAGTACCGGCAGGAACAGCAGAGTGCTGTGGAT
GTTGACGATGGTCATTTTGTCAACATAGAATTGGAGTAAAAAACTACCTTGTTTCTACT
(SEQ ID NO: 3)

NS
AGCAAAAGCAGGGTGACAAAAACATAATGGATTCCAACACTGTGTCAAGCTTTCAGG
TAGACTGCTTTCTTTGGCATGTCCGCAAACGATTTGCAGACCAAGAACTGGGTGATG
CCCCATTCCTTGACCGGCTTCGCCGAGATCAGAAGTCCCTAAGAGGAAGAGGCAAC
ACTCTTGGTCTGGACATCGAAACAGCTACTCGCGCAGGAAAGCAGATAGTGGAGCG
GATTCTGGAGGGGGAGTCTGATAAGGCACTTAAAATGCCGGCTTCACGCTACCTAAC
TGACATGACTCTCGAAGAAATGTCAAGGGACTGGTTCATGCTCATGCCCAAGCAGAA
AGTGGCAGGTTCCCTTTGCATCAAAATGGACCAGGCAATAATGGATAAAACCATCAT
ATTGAAAGCAAACTTCAGTGTGATTTTTGACCGGTTGGAAACCCTAATACTACTTAGA
GCTTTCACAGAAGAAGGAGCAATCGTGGGAGAAATCTCACCATTACCTTCTCTTCCA
GGACATACTGGTGAGGATGTCAAAAATGCAATTGGCGTCCTCATCGGAGGACTTGAA
TGGAATGATAACACAGTTCGAGTCACTGAAACTATACAGAGATTCGCTTGGAGAAAC
AGTGATGAGGATGGGAGACTTCCACTCCCTCCAAATCAGAAACGGTAAATGGCGAGA
ACAATTGAGTCAGAAGTTTGAAGAAATAAGGTGGCTGATTGAAGAAGTAAGACATAG
ATTGAAAATTACAGAAAACAGCTTCGAACAGATAACGTTTATGCAAGCCTTACAACTA
CTGCTTGAAGTGGAGCAAGAGATAAGAGCCTTCTCGTTTCAGCTTATTTAATGATAAA
AAACACCCTTGTTTCTACT (SEQ ID NO: 4)

NP
AGCAAAAGCAGGGTAGATAATCACTCACCGAGTGACATCAGCATCATGGCGTCTCAA
GGCACCAAACGATCTTATGAACAGATGGAAACTGGTGGGGAACGCCAGAATGCTACT
GAGATCAGGGCATCTGTTGGAAGAATGGTTAGTGGCATTGGGAGGTTCTACATACAG
ATGTGCACAGAACTCAAACTCAGTGACTATGAAGGGAGGCTGATCCAGAACAGCATA
ACAATAGAGAGAATGGTACTCTCTGCATTTGATGAAGAAGGAACAGATACCTGGAA
GAACACCCCAGTGCGGGAAAGGACCCGAAGAAGACTGGAGGTCCAATTTATCGGAG
GAGAGACGGGAAATGGGTGAGAGAGCTAATTCTGTACGACAAAGAGGAGATCAGGA
GGATTTGGCGTCAAGCGAACAATGGAGAGGACGCAACTGCTGGTCTTACCCACCTG
ATGATATGGCATTCCAATCTAAATGATGCCACATATCAGAGAACGAGAGCTCTCGTG
CGTACTGGAATGGACCCAAGGATGTGCTCTCTGATGCAAGGGTCAACTCTCCCGAG
GAGATCTGGAGCTGCCGGTGCAGCAGTAAAGGGGGTAGGGACAATGGTGATGGAG
CTGATTCGGATGATAAAACGAGGGATCAACGACCGGAATTTCTGGAGAGGCGAAAAT
GGAAGAAGAACAAGGATTGCATATGAGAGAATGTGCAACATCCTCAAAGGGAAATTC

CAAACAGCAGCACAAAGAGCAATGATGGATCAAGTGCGAGAGAGCAGAAATCCTGG
GAATGCTGAAATTGAAGATCTCATTTTTCTGGCACGGTCTGCACTCATCCTGAGAGG
ATCAGTGGCCCATAAGTCCTGCTTGCCTGCTTGTGTGTACGGACTTGCAGTGGCCAG
TGGATATGACTTTGAGAGAGAAGGGTACTCTCTGGTTGGAATAGATCCTTTCCGCCT
GCTTCAAAACAGCCAGGTCTTTAGTCTCATTAGACCAAATGAGAATCCAGCACATAAG
AGTCAATTAGTGTGGATGGCATGCCACTCTGCAGCATTTGAGGACCTTAGAGTCTCA
AGTTTCATCAGAGGGACAAGAGTGGTCCCAAGAGGACAGCTATCCACCAGAGGGGT
TCAAATTGCTTCAAATGAGAACATGGAGGCAATGGACTCCAACACTCTTGAACTGAG
AAGCAGATATTGGGCTATAAGAACCAGAAGCGGAGGAAACACCAACCAGCAGAGGG
CATCTGCAGGACAGATCAGCGTTCAGCCCACTTTCTCGGTCCAGAGAAACCTTCCCT
TCGAAAGAGCGACCATTATGGCAGCATTTACAGGAAATACTGAGGGCAGAACGTCTG
ACATGAGGACTGAAATCATAAGAATGATGGAAAGTGCCAGACCAGAAGATGTGTCAT
TCCAGGGGCGGGGAGTCTTCGAGCTCTCGGACGAAAAGGCAACGAACCCGATCGT
GCCTTCCTTTGACATGAATAATGAAGGATCTTATTTCTTCGGAGACAATGCAGAGGAG
TATGACAATTAAAGAAAAATACCCTTGTTTCTACT (SEQ ID NO: 5)

PA
AGCGAAAGCAGGTACTGATCCAAAATGGAAGACTTTGTGCGACAATGCTTCAATCCA
ATGATTGTCGAGCTTGCGGAAAAGGCAATGAAAGAATATGGGGAAGATCCGAAAATC
GAAACGAACAAGTTTGCTGCAATATGCACACACTTGGAGGTCTGTTTCATGTATTCGG
ATTTTCACTTTATTGATGAACGGAGTGAATCAATAATTGTAGAATCTGGAGATCCGAA
TGCATTATTGAAACACCGATTTGAAATAATTGAAGGAAGAGACCGAACGATGGCCTG
GACTGTGGTGAATAGTATCTGCAACACCACAGGAGTTGAGAAACCTAAATTTCTCCC
AGATTTGTATGACTACAAAGAGAACCGATTCATCGAAATTGGAGTGACACGGAGGGA
AGTTCATACATACTATCTGGAGAAAGCCAACAAGATAAAATCCGAGGAGACACATATT
CACATATTCTCATTCACAGGGGAGGAAATGGCCACCAAAGCGGACTACACCCTTGAT
GAAGAGAGCAGGGCAAGAATTAAAACCAGGCTGTTCACCATAAGGCAGGAAATGGC
CAGTAGGGGTCTATGGGATTCCTTTCGTCAATCCGAGAGAGGCGAAGAGACAATTGA
AGAAAAATTTGAAATCACTGGAACCATGCGCAGACTTGCAGACCAAAGTCTCCCACC
GAACTTCTCCAGCCTTGAAAACTTTAGAGCCTATGTGGATGGATTCGAACCGAACGG
CTGCATTGAGGGCAAGCTTTCTCAAATGTCAAAGAAGTGAATGCTAGAATTGAGCC
ATTTTTGAAGACAACGCCACGCCCTCTCAGACTACCTGATGGGCCTCCTTGCTCTCA
GCGGTCGAAGTTCTTGCTGATGGATGCCCTTAAATTAAGCATCGAAGACCCGAGTCA
TGAGGGGAGGGGATACCACTATACGATGCAATCAAATGCATGAAGACATTTTCGG
CTGGAAAGAGCCCAACATCGTGAAACCACATGAAAAGGTATAAACCCCAATTACCT
CCTGGCTTGGAAGCAAGTGCTGGCAGAACTCCAAGATATTGAAAATGAGGAGAAAAT
CCCAAAAACAAAGAACATGAAAAAAACAAGCCAGTTGAAGTGGGCACTCGGTGAGAA
CATGGCACCAGAGAAAGTAGACTTTGAGGACTGCAAAGATGTTAGCGATCTAAGACA
GTATGACAGTGATGAACCAGAGTCTAGATCACTAGCAAGCTGGATTCAGAGTGAATT
CAACAAGGCATGTGAATTGACAGATTCGATTTGGATTGAACTCGATGAAATAGGAGA
AGACGTAGCTCCAATTGAGCACATTGCAAGTATGAGAAGGAACTATTTTACAGCGGA
AGTATCCCATTGCAGGGCCACTGAATACATAATGAAGGGAGTGTACATAAACACAGC
CCTGTTGAATGCATCCTGTGCAGCCATGGATGACTTTCAACTGATTCCAATGATAAGC
AAATGCAGAACCAAAGAAGGAAGACGGAAAACTAATCTGTATGGATTCATTATAAAAG
GGAGATCCCACTTGAGGAATGATACCGATGTGGTAAATTTTGTGAGTATGGAATTCTC
TCTTACTGATCCGAGGCTGGAGCCACACAAGTGGGAAAAGTACTGTGTCCTCGAGAT
AGGAGACATGCTCCTCCGGACTGCAGTAGGCCAAGTTTCGAGGCCCATGTTCCTGT
ATGTAAGAACCAATGGAACCTCCAAGATCAAAATGAAATGGGGCATGGAAATGAGGC
GATGCCTTCTTCAATCCCTTCAACAAATTGAAAGCATGATTGAAGCCGAGTCTTCTGT
CAAAGAGAAGGACATGACCAAAGAATTCTTTGAAAACAAATCAGAAACATGGCCGATT
GGAGAGTCCCCCAAGGGAGTGGAGGAAGGCTCCATCGGAAAGGTGTGCAGAACCTT
GCTGGCGAAGTCTGTGTTCAACAGTTTATATGCATCTCCACAACTCGAGGGGTTTTC
AGCTGAATCAAGAAAATTGCTTCTCATTGCTCAGGCACTTAGGGACAACCTGGAACC
TGGGACCTTCGATCTTGGAGGGCTATATGAAGCAATTGAGGAGTGCCTGATTAACGA
TCCCTGGGTTTTGCTTAATGCGTCTTGGTTCAACTCCTTCCTCGCACATGCACTGAAA
TAGTTGTGGCAATGCTACTATTTGCTATCCATACTGTCCAAAAAAGTACCTTGTTTCTA
CT (SEQ ID NO: 6)

Figure 2 (cont'd)

PB1
AGCGAAAGCAGGCAAACCATTTGAATGGATGTCAATCCGACTTTACTTTTCTTGAAAG
TACCAGTGCAAAATGCTATAAGTACCACCTTCCCTTATACTGGAGACCCTCCATACAG
CCATGGAACAGGGACAGGATACACCATGGACACAGTCAACAGAACACACCAATATTC
AGAAAAGGGGAAGTGGACAACAAACACAGAGACTGGAGCACCCCAACTCAACCCGA
TTGATGGACCACTACCTGAGGATAATGAGCCCAGTGGGTACGCACAAACAGATTGTG
TATTGGAAGCAATGGCTTTCCTTGAAGAATCCCACCCAGGGATCTTTGAAAACTCGT
GTCTTGAAACGATGGAAATTGTTCAACAAACAAGAGTGGATAAACTGACCCAAGGTC
GCCAGACCTATGACTGGACATTGAATAGAAACCAACCGGCTGCAACTGCTTTGGCCA
ACACTATAGAAATCTTCAGATCGAACGGTCTAACAGCCAATGAATCGGGACGGCTAA
TAGATTTCCTCAAGGATGTGATGGAGTCAATGGATAAGGAAGAAATGGAGATAACAA
CACATTTCCAGAGAAGAGAAGGGTGAGGGACAACATGACCAAGAAAATGGTCACAC
AAAGAACAATAGGGAAGAAAAAACAAAGGCTGAACAAAAAGAGCTACCTGATAAGAG
CACTGACACTGAACACAATGACAAAAGATGCAGAAAGAGGCAAATTGAAGAGGCGAG
CGATTGCAACACCCGGAATGCAAATCAGAGGATTCGTGTACTTTGTTGAAACACTAG
CGAGGAGTATCTGTGAGAAACTTGAGCAATCTGGACTCCCAGTCGGAGGGAATGAG
AAGAAGGCTAAATTGGCAAACGTCGTGAGGAAGATGATGACTAACTCACAAGATACT
GAACTCTCCTTTACAATTACTGGAGACAATACCAAATGGAATGAGAATCAGAATCCTA
GGATGTTTCTGGCAATGATAACGTACATCACAAGGAACCAGCCAGAATGGTTTCGGA
ATGTCTTAAGCATAGCTCCTATAATGTTCTCAAACAAAATGGCGAGACTAGGAAAAGG
ATACATGTTCGAAAGTAAGAGCATGAAGTTACGAACACAAATACCAGCAGAAATGCTT
GCAAACATTGATCTTAAATACTTCAATGAATTAACGAAAAAGAAAATTGAGAAAATAAG
GCCTCTATTAATAGATGGTACAGCCTCATTGAGCCCTGGAATGATGATGGGCATGTT
CAACATGCTGAGTACAGTCCTAGGAGTTTCAATCCTGAATCTTGGACAGAAAAGGTA
CACCAAAACCACATATTGGTGGGACGGACTCCAATCCTCTGATGATTTCGCTCTCAT
CGTAAATGCACCGAATCATGAGGGAATACAAGCAGGAGTGGATAGGTTTTATAGGAC
TTGTAAACTAGTTGGAATCAATATGAGCAAGAAGAAGTCTTACATAAATCGGACAGGG
ACATTTGAATTCACGAGCTTTTTCTACCGCTATGGATTTGTAGCCAATTTCAGTATGG
AGCTGCCCAGTTTTGGAGTGTCTGGAATTAATGAATCGGCCGACATGAGCATTGGTG
TTACAGTGATAAAAAACAATATGATAAACAACGACCTTGGGCCAGCAACAGCTCAGAT
GGCTCTTCAGTTATTCATCAAGGACTACAGATACACATACCGATGCCACAGAGGGGA
TACGCAAATCCAAACAAGGAGATCATTCGAGCTGAAGAAGCTGTGGGAGCAAACCC
GTTCAAAGGCAGGACTGTTGGTTTCAGATGGAGGACCAAATCTATACAATATCCGAA
ACCTCCATATTCCTGAAGTCTGCTTAAAATGGGAATTGATGGATGAAGATTACCAGGG
CAGACTGTGTAATCCTCTGAATCCATTCGTCAGCCATAAGGAAATTGAATCTGTCAAC
AATGCTGTAGTAATGCCAGCTCATGGCCCGGCCAAGAGTATGGAATATGATGCCGTT
GCAACTACACATTCATGGATTCCTAAAAGGAACCGTTCCATTCTCAATACGAGTCAAA
GGGGAATTCTTGAGGATGAACAGATGTACCAGAAGTGCTGCAATCTATTCGAGAAAT
TCTTCCCCAGCAGTTCATATCGGAGGCCAGTTGGAATTTCCAGCATGGTGGAGGCCA
TGGTGTCTAGGGCCCGAATTGACGCACGAATCGATTTCGAGTCTGGAAGGATTAAGA
AGAAGAGTTTGCCGAGATCATGAAGATCTGTTCCACCATTGAAGAACTCAGACGGC
AAAAATAGTGAATTTAGCTTGTCCTTCGTGAAAAAATGCCTTGTTTCTACT (SEQ ID NO: 7)

PB2
AGCGAAAGCAGGTCAAATATATTCAATATGGAGAGGATAAAAGAATTACGAGATCTAA
TGTCACAGTCCCGCACTCGCGAGATACTAACAAAAACCACTGTGGACCATATGGCCA
TAATCAAGAAATACACATCAGGAAGACAAGAGAAGAACCCTGCTCTCAGAATGAAAT
GGATGATGGCAATGAAATATCCAATCACAGCGGACAAGAGAATAATAGAGATGATTC
CTGAAAGGAATGAACAAGGGCAGACGCTCTGGAGCAAGACAAATGATGCTGGATCG
GACAGGGTGATGGTGTCTCCCCTAGCTGTAACTTGGTGGAATAGGAATGGGCCGGC
GACAAGTGCAGTTCATTATCCAAAGGTTTACAAAACATACTTTGAGAAGGTTGAAAGA
TTAAAACATGGAACCTTCGGTCCCGTTCATTTCCGAAACCAGGTTAAAATACGCCGC
CGAGTTGATATAAATCCTGGCCATGCAGATCTCAGTGCTAAAGAAGCACAAGATGTC
ATCATGGAGGTCGTTTTCCCAAATGAAGTGGGAGCTAGAATATTGACATCAGAGTCG
CAATTGACAATAACGAAAGAGAAGAAAGAAGAGCTCCAAGATTGTAAGATTGCTCCC
TTAATGGTTGCATACATGTTGGAAAGGGAACTGGTCCGCAAGACCAGATTCCTACCG
GTAGCAGGCGGAACAAGTAGTGTGTACATTGAGGTATTGCATTTGACTCAAGGGACC
TGCTGGGAACAGATGTACACTCCAGGCGGAGAAGTGAGAAATGACGATGTTGACCA

Figure 2 (cont'd)

GAGTTTGATCATTGCTGCCAGAAACATTGTTAGGAGAGCAACAGTATCAGCGGATCC
ACTGGCATCACTGCTGGAGATGTGTCACAGCACACAAATTGGTGGGATAAGGATGGT
GGACATCCTTAGGCAAAATCCAACTGAGGAACAAGCTGTGGATATATGCAAAGCAGC
AATGGGTCTTAGGATCAGTTCTTCCTTTAGCTTTGGAGGCTTCACTTTCAAAAGAACA
AGTGGATCATCCGTCAAGAAGGAAGAGGAAGTGCTTACAGGCAACCTCCAAACATTG
AAAATAAGAGTACATGAGGGGTATGAGGAATTCACAATGGTTGGGCGGAGGGCAAC
AGCTATCCTGAGGAAAGCAACTAGAAGGCTGATTCAGTTGATAGTAAGTGGAAGAGA
CCAACAATCAATCGCTGAGGCAATCATTGTAGCAATGGTGTTCTCACAGGAGGATTG
CATGATAAAGGCAGTCCGAGGCGATCTGAATTTCGTAAACAGAGCAAACCAAAGATT
AAACCCCATGCATCAACTCCTGAGACATTTTCAAAAGGACGCAAAAGTGCTATTTCAG
AATTGGGGAATTGAACCCATTGATAATGTCATGGGGATGATCGGAATATTACCTGACA
TGACTCCCAGCACAGAAATGTCACTGAGAGGAGTAAGAGTTAGTAAAATGGGAGTGG
ATGAATATTCCAGCACTGAGAGAGTAGTTGTAAGTATTGACCGTTTCTTAAGGGTTCG
AGATCAGCGGGGGAACGTACTCTTATCTCCCGAAGAGGTCAGCGAAACCCAGGGAA
CAGAGAAATTGACAATAACATATTCATCATCAATGATGTGGGAAATCAACGGTCCTGA
GTCAGTGCTTGTTAACACCTATCAGTGGATCATCAGAAACTGGGAGACTGTGAAGAT
TCAATGGTCTCAAGACCCCACGATGCTGTACAATAAGATGGAGTTTGAACCGTTCCA
ATCCTTGGTACCCAAAGCTGCCAGAGGTCAATACAGTGGATTTGTGAGAACATTATTC
CAGCAAATGCGTGACGTACTGGGGACATTTGATACTGTCCAGATAATAAAGCTGCTA
CCATTTGCAGCAGCCCCACCGAAGCAGAGCAGAATGCAGTTTTCTTCTCTAACTGTG
AATGTGAGAGGCTCAGGAATGAGAATACTCGTAAGGGGCAATTCCCCTGTGTTCAAC
TACAATAAGGCAACCAAAAGGCTTACCGTCCTTGGAAAGGACGCAGGTGCATTAACA
GAGGATCCGGATGAAGGGACAGCCGGAGTGGAGTCTGCAGTACTGAGGGGATTCTT
AATTTTAGGCAAGGAGGACAAAAGGTATGGACCAGCATTGAGCATCAATGAACTGAG
CAATCTTGCGAAGGGGAGAAAGCTAATGTGCTGATAGGGCAAGGTGACGTGGTGT
TGGTAATGAAACGAAAACGGGACTCTAGCATACTTACTGACAGCCAGACAGCGACCA
AAAGAATTCGGATGGCCATCAATTAG<u>TGTCGAATTGTTTAAAAACGACCTTGTTTCTA
CT</u> (SEQ ID NO: 8)

Figure 2 (cont'd)

FIGURE 3
A/Turkey/Turkey/1/05 Attenuated Strain Gene Sequences

HA
AGCAAAAGCAGGGGTTCAATCTGTCAAAATGGAGAAAATAGTGCTTCTTCTTGCAATA
GTCAGCCTTGTTAAAAGTGATCAGATTTGCATTGGTTACCATGCAAACAACTCGACAG
AGCAGGTTGACACAATAATGGAAAAGAACGTCACTGTTACACATGCCCAAGACATACT
GGAAAAGACACACAACGGGAAACTCTGCGATCTAGATGGAGTGAAGCCTCTAATTTT
AGAGAGATTGTAGTGTAGCTGGATGGCTCCTCGGGAACCCAATGTGTGACGAATTCCT
CAATGTGCCGGAATGGTCTTACATAGTGGAGAAGATCAATCCAGCCAATGACCTCTG
TTACCCAGGGTATTTCAACGACTATGAAGAACTGAAACACCTATTGAGCAGAATAAAC
CATTTTGAGAAAATTCAGATCATCCCCAAAAGTTCTTGGTCAGACATGAAGCCTCAG
CAGGGGTGAGCTCAGCATGTCCATACCAGGGAAGGTCCTCCTTTTTAGAAATGTGG
TATGGCTTATCAAAAGGACAATGCATACCCAACAATAAAGAGAAGTTACAATAATAC
CAACCAAGAAGATCTTTTGGTATTGTGGGGATTCACCATCCAAATGATGCGGCAGA
GCAGACAAGGCTCTATCAAAACCCAACTACCTATATTTCCGTTGGGACATCAACACTA
AACCAGAGATTGGTACCAAAAATAGCCACTAGATCTAAGGTAAACGGGCAAAGTGGA
AGGATGGAGTTCTTTTGGACAATTTTAAAACCGAATGATGCAATAAACTTTGAGAGTA
ATGGAAATTTCATTGCTCCAGAAAATGCATACAAAATTGTCAAGAAAGGGGACTCAAC
AATTATGAAAAGTGAGTTGGAATATGGTAACTGCAACACCAAGTGTCAAACTCCAATA
GGGGCGATAAACTCTAGTATGCCATTCCACAACATCCACCCTCTCACCATCGGGGAA
TGCCCCAAATATGTGAAATCAAGCAGATTAGTCCTTGCTACTGGGCTCAGAAATAGC
CCTCAAACCGAGACCCGAGGACTATTTGGAGCTATAGCAGGTTTTATAGAGGGAGGA
TGGCAGGGAATGGTAGATGGTTGGTATGGGTACCACCATAGCAACGAGCAGGGGAG
TGGGTACGCTGCAGACAAAGAATCCACTCAAAAGGCAATAGATGGAGTCACCAATAA
GGTCAACTCGATCATTGACAAAATGAACACTCAGTTTGAGGCTGTTGGAAGGGAATT
TAATAACTTAGAAAGGAGAATAGAAAATTTAAACAAGAAGATGGAAGACGGATTCCT
AGATGTCTGGACTTATAATGCTGAACTTCTGGTTCTCATGGAAAATGAGAGAACTCTA
GACTTTCATGACTCAAATGTCAAGAACCTTTACGACAAGGTCCGACTACAGCTTAGG
GATAATGCAAAGGAGCTTGGTAACGGTTGTTTCGAGTTCTATCACAGATGTGATAATG
AATGTATGGAAAGTGTAAGAAACGGAACGTATGACTACCCGCAGTATTCAGAAGAAG
CAAGATTAAAAAGAGAGGAAATAAGTGGAGTAAAATTGGAATCAATAGGAACTTACCA
AATACTGTCAATTTATTCAACAGTGGCGAGCTCCCTAGCACTGGCAATCATGGTGGCT
GGTCTATCTTTATGGATGTGCTCCAATGGATCGTTACAATGCAGAATTTGCATTTAAA
TTTGTGAGTTCAGATTGTAGTTAAAAACACCCTTGTTTCTACT (SEQ ID NO: 9)

NA
AGCAAAAGCAGGAGTTCAAAATGAATCCAAATCAGAAGATAATAACCATCGGATCAAT
CTGTATGGTAATTGGAATAGTTAGCTTAATGTTACAAATTGGGAACATGATCTCAATA
TGGGTCAGTCATTCAATTCAGACAGGGAATCAATGCCAAGCTGAACCAATCAGCAATA
CTAAATTTCTTACTGAGAAAGCTGTGGCTTCAGTAACATTAGCGGGCAATTCATCTCT
TTGCCCCATTAGCGGATGGGCTGTATACAGTAAGGACAACAGTATAAGGATCGGTTC
CAGGGGGGATGTGTTTGTTATAAGAGAGCCGTTCATCTCATGCTCCCACTTGGAATG
CAGAACTTTCTTTTTGACTCAGGGAGCCTTGCTGAATGACAAGCACTCCAATGGGAC
TGTCAAAGACAGAAGCCCTCACAGAACATTAATGAGTTGTCCTGTGGGTGAGGCTCC
CTCCCCATATAACTCAAGGTTTGAGTCTGTTGCTTGGTCAGCAAGTGCTTGCCATGAT
GGCACCAGTTGGTTGACAATTGGAATTTCTGGTCCAGACAATGGGGCTGTGGCTGT
ATTGAAATACAATGGCATAATAACAGACACCATCAAGAGTTGGAGGAACAACATACTG
AGAACTCAAGAGTCTGAATGTGCATGTGTAAATGGCTCTTGCTTTACTGTAATGACTG
ATGGACCAAGTAGTGGGCAGGCATCATATAAGATCTTCAAAATGGAAAAAGGGAAAG
TGGTTAAATCAGTCGAATTGGATGCTCCTAATTATCACTATGAGGAGTGCTCCTGTTA
TCCTGATGCCGGCGAAATCACATGTGTGTGCAGGGATAATTGGCATGGCTCAAATAG
GCCATGGGTATCTTTCAATCAAAATTTGGAGTATCAAATAGGATATATATGCAGTGGA
GTTTTCGGAGACAATCCACGCCCCAATGATGGAACAGGTAGTTGTGGTCCGGTGTTC
TCTAACGGGGCATATGGGGTAAAAGGGTTTTCATTCAAATACGGCAATGGTGTTTGG
ATCGGGAGAACCAAAAGCACTAATTCCAGGAGCGGCTTTGAAATGATTTGGGACCCA
AATGGGTGGACTGGAACGGACAGTAGCTTTTCGGTGAAGCAAGATATCGTAGCAATA
ACTGATTGGTCAGGATATAGCGGGAGTTTTGTCCAGCATCCAGAACTGACAGGATTA
GATTGCATAAGACCTTGTTTCTGGGTTGAGTTAATCAGAGGGCGGCCTAAAGAGAGC
ACAATTTGGACCAGTGGGAGCAGCATATCTTTTTGTGGTGTAAATAGTGACACTGTTA
GTTGGTCTTGGCCAGACGGTGCTGAGTTGCCATTCACCATTGACAAGTAGTTTGTTC
AAAAAACTCCTTGTTTCTACT (SEQ ID NO: 10)

M
AGCAAAAGCAGGTAGATGTTGAAAGATGAGTCTTCTAACCGAGGTCGAAACGTACGT
TCTCTCTATCATCCCGTCAGGCCCCCTCAAAGCCGAGATCGCACAGAAACTTGAAGA
TGTCTTTGCAGGAAAGAACACCGATCTCGAGGCTCTCATGGAGTGGCTAAAGACAAG
ACCAATCCTGTCACCTCTGACTAAAGGGATTTTGGGATTTGTATTCACGCTCACCGTG
CCCAGTGAGCGAGGACTGCAGCGTAGACGCTTTGTCCAGAATGCCCTAAATGGAAA
TGGAGATCCAAATAATATGGATAGGGCAGTTAAGCTATATAAGAAGCTGAAAAGAGA
AATAACATTCCATGGGGCTAAGGAGGTCGCACTCAGCTACTCAACCGGTGCACTTGC
CAGTTGCATGGGTCTCATATACAACAGGATGGGAACGGTGACTACGGAAGTGGCTTT
TGGCCTAGTGTGTGCCACTTGTGAGCAGATTGCAGATTCACAGCATCGGTCTCACAG
ACAGATGGCAACTATCACCAACCCACTAATCAGACATGAGAACAGAATGGTGCTGGC
CAGCACTACAGCTAAGGCTATGGAGCAGATGGCGGGATCAAGTGAGCAGGCAGCG
GAAGCCATGGAGATCGCTAATCAGGCTAGGCAGATGGTGCAGGCAATGAGGACAAT
TGGGACTCATCCTAACTCTAGTGCTGGTCTGAGAGATAATCTTCTTGAAAATTTGCAG
GCCTACCAGAAACGAATGGGAGTGCAGATGCAGCGATTCAAGTGATCCTATTGTTGT
TGCCGCAAATATCATTGGGATCTTGCACTTGATATTGTGGATTCTTGATCGTCTTTTCT
TCAAATGCATTTATCGTCGCCTTAAATACGGTTTGAAAAGAGGGCCTGCTACGGCAG
GGGTACCTGAGTCTATGAGGGAAGAGTACCGGCAGGAACAGCAGAGTGCTGTGGAT
GTTGACGATGGTCATTTTGTCAACATAGAATTGGAGTAAAAAACTACCTTGTTTCTACT
(SEQ ID NO: 3)

AGCAAAAGCAGGGTGACAAAAACATAATGGATTCCAACACTGTGTCAAGCTTTCAGG
TAGACTGCTTTCTTTGGCATGTCCGCAAACGATTTGCAGACCAAGAACTGGGTGATG
CCCCATTCCTTGACCGGCTTCGCCGAGATCAGAAGTCCCTAAGAGGAAGAGGCAAC
ACTCTTGGTCTGGACATCGAAACAGCTACTCGCGCAGGAAAGCAGATAGTGGAGCG
GATTCTGGAGGGGAGTCTGATAAGGCACTTAAAATGCCGGCTTCACGCTACCTAAC
TGACATGACTCTCGAAGAAATGTCAAGGGACTGGTTCATGCTCATGCCCAAGCAGAA
AGTGGCAGGTTCCCTTTGCATCAAAATGGACCAGGCAATAATGGATAAACCATCAT
ATTGAAAGCAAACTTCAGTGTGATTTTTGACCGGTTGGAAACCCTAATACTACTTAGA
GCTTTCACAGAAGAAGGAGCAATCGTGGGAGAAATCTCACCATTACCTTCTCTTCCA
GGACATACTGGTGAGGATGTCAAAAATGCAATTGGCGTCCTCATCGGAGGACTTGAA
TGGAATGATAACACAGTTCGAGTCACTGAAACTATACAGAGATTCGCTTGGAGAAAC
AGTGATGAGGATGGGAGACTTCCACTCCCTCCAAATCAGAAACGGTAAATGGCGAGA
ACAATTGAGTCAGAAGTTTGAAGAAATAAGGTGGCTGATTGAAGAAGTAAGACATAG
ATTGAAAATTACAGAAAACAGCTTCGAACAGATAACGTTTATGCAAGCCTTACAACTA
CTGCTTGAAGTGGAGCAAGAGATAAGAGCCTTCTCGTTTCAGCTTATTTAATGATAAA
AAACACCCTTGTTTCTACT (SEQ ID NO: 4)

NP

AGCAAAAGCAGGGTAGATAATCACTCACCGAGTGACATCAGCATCATGGCGTCTCAA
GGCACCAAACGATCTTATGAACAGATGGAAACTGGTGGGGAACGCCAGAATGCTACT
GAGATCAGGGCATCTGTTGGAAGAATGGTTAGTGGCATTGGGAGGTTCTACATACAG
ATGTGCACAGAACTCAAACTCAGTGACTATGAAGGGAGGCTGATCCAGAACAGCATA
ACAATAGAGAGAATGGTACTCTCTGCATTTGATGAAAGAAGGAACAGATACCTGGAA
GAACACCCCAGTGCGGGAAAGGACCCGAAGAAGACTGGAGGTCCAATTTATCGGAG
GAGAGACGGGAAATGGGTGAGAGAGCTAATTCTGTACGACAAAGAGGAGATCAGGA
GGATTTGGCGTCAAGCGAACAATGGAGAGGACGCAACTGCTGGTCTTACCCACCTG
ATGATATGGCATTCCAATCTAAATGATGCCACATATCAGAGAACGAGAGCTCTCGTG
CGTACTGGAATGGACCCAAGGATGTGCTCTCTGATGCAAGGGTCAACTCTCCCGAG
GAGATCTGGAGCTGCCGGTGCAGCAGTAAAGGGGGTAGGGACAATGGTGATGGAG
CTGATTCGGATGATAAAACGAGGGATCAACGACCGGAATTTCTGGAGAGGCGAAAAT
GGAAGAAGAACAAGGATTGCATATGAGAGAATGTGCAACATCCTCAAAGGGAAATTC
CAAACAGCAGCACAAAGAGCAATGATGGATCAAGTGCGAGAGAGCAGAAATCCTGG
GAATGCTGAAATTGAAGATCTCATTTTTCTGGCACGGTCTGCACTCATCCTGAGAGG
ATCAGTGGCCCATAAGTCCTGCTTGCCTGCTTGTGTGTACGGACTTGCAGTGGCCAG
TGGATATGACTTTGAGAGAGAAGGGTACTCTCTGGTTGGAATAGATCCTTTCCGCCT
GCTTCAAAACAGCCAGGTCTTTAGTCTCATTAGACCAAATGAGAATCCAGCACATAAG
AGTCAATTAGTGTGGATGGCATGCCACTCTGCAGCATTTGAGGACCTTAGAGTCTCA
AGTTTCATCAGAGGGACAAGAGTGGTCCCAAGAGGACAGCTATCCACCAGAGGGGT
TCAAATTGCTTCAAATGAGAACATGGAGGCAATGGACTCCAACACTCTTGAACTGAG
AAGCAGATATTGGGCTATAAGAACCAGAAGCGGAGGAAACACCAACCAGCAGAGGG
CATCTGCAGGACAGATCAGCGTTCAGCCCACTTTCTCGGTCCAGAGAAACCTTCCCT
TCGAAAGAGCGACCATTATGGCAGCATTTACAGGAAATACTGAGGGCAGAACGTCTG
ACATGAGGACTGAAATCATAAGAATGATGGAAAGTGCCAGACCAGAAGATGTGTCAT
TCCAGGGGCGGGGAGTCTTCGAGCTCTCGGACGAAAAGGCAACGAACCCGATCGT
GCCTTCCTTTGACATGAATAATGAAGGATCTTATTTCTTCGGAGACAATGCAGAGGAG
TATGACAATTAAAGAAAAATACCCTTGTTTCTACT (SEQ ID NO: 5)

Figure 3 (cont'd)

PA
AGCGAAAGCAGGTACTGATCCAAAATGGAAGACTTTGTGCGACAATGCTTCAATCCA
ATGATTGTCGAGCTTGCGGAAAAGGCAATGAAAGAATATGGGGAAGATCCGAAAATC
GAAACGAACAAGTTTGCTGCAATATGCACACACTTGGAGGTCTGTTTCATGTATTCGG
ATTTTCACTTTATTGATGAACGGAGTGAATCAATAATTGTAGAATCTGGAGATCCGAA
TGCATTATTGAAACACCGATTTGAAATAATTGAAGGAAGAGACCGAACGATGGCCTG
GACTGTGGTGAATAGTATCTGCAACACCACAGGAGTTGAGAAACCTAAATTTCTCCC
AGATTTGTATGACTACAAGAGAACCGATTCATCGAAATTGGAGTGACACGGAGGGA
AGTTCATACATACTATCTGGAGAAAGCCAACAAGATAAAATCCGAGGAGACACATATT
CACATATTCTCATTCACAGGGGAGGAAATGGCCACCAAAGCGGACTACACCCTTGAT
GAAGAGAGCAGGGCAAGAATTAAAACCAGGCTGTTCACCATAAGGCAGGAAATGGC
CAGTAGGGGTCTATGGGATTCCTTTCGTCAATCCGAGAGAGGCGAAGAGACAATTGA
AGAAAAATTTGAAATCACTGGAACCATGCGCAGACTTGCAGACCAAAGTCTCCCACC
GAACTTCTCCAGCCTTGAAAACTTTAGAGCCTATGTGGATGGATTCGAACCGAACGG
CTGCATTGAGGGCAAGCTTTCTCAAATGTCAAAGAAGTGAATGCTAGAATTGAGCC
ATTTTTGAAGACAACGCCACGCCCTCTCAGACTACCTGATGGGCCTCCTTGCTCTCA
GCGGTCGAAGTTCTTGCTGATGGATGCCCTTAAATTAAGCATCGAAGACCCGAGTCA
TGAGGGGGAGGGGATACCACTATACGATGCAATCAAATGCATGAAGACATTTTTCGG
CTGGAAAGAGCCCAACATCGTGAAACCACATGAAAAGGTATAAACCCCAATTACCT
CCTGGCTTGGAAGCAAGTGCTGGCAGAACTCCAAGATATTGAAAATGAGGAGAAAAT
CCCAAAAACAAAGAACATGAAAAAAACAAGCCAGTTGAAGTGGGCACTCGGTGAGAA
CATGGCACCAGAGAAAGTAGACTTTGAGGACTGCAAAGATGTTAGCGATCTAAGACA
GTATGACAGTGATGAACCAGAGTCTAGATCACTAGCAAGCTGGATTCAGAGTGAATT
CAACAAGGCATGTGAATTGACAGATTCGATTTGGATTGAACTCGATGAAATAGGAGA
AGACGTAGCTCCAATTGAGCACATTGCAAGTATGAGAAGGAACTATTTTACAGCGGA
AGTATCCCATTGCAGGGCCACTGAATACATAATGAAGGGAGTGTACATAAACACAGC
CCTGTTGAATGCATCCTGTGCAGCCATGGATGACTTTCAACTGATTCCAATGATAAGC
AAATGCAGAACCAAAGAAGGAAGACGGAAAACTAATCTGTATGGATTCATTATAAAAG
GGAGATCCCACTTGAGGAATGATACCGATGTGGTAAATTTTGTGAGTATGGAATTCTC
TCTTACTGATCCGAGGCTGGAGCCACACAAGTGGGAAAAGTACTGTGTCCTCGAGAT
AGGAGACATGCTCCTCCGGACTGCAGTAGGCCAAGTTTCGAGGCCCATGTTCCTGT
ATGTAAGAACCAATGGAACCTCCAAGATCAAAATGAAATGGGGCATGGAAATGAGGC
GATGCCTTCTTCAATCCCTTCAACAAATTGAAAGCATGATTGAAGCCGAGTCTTCTGT
CAAAGAGAAGGACATGACCAAAGAATTCTTTGAAAACAAATCAGAAACATGGCCGATT
GGAGAGTCCCCCAAGGGAGTGGAGGAAGGCTCCATCGGAAAGGTGTGCAGAACCTT
GCTGGCGAAGTCTGTGTTCAACAGTTTATATGCATCTCCACAACTCGAGGGGTTTTC
AGCTGAATCAAGAAATTGCTTCTCATTGCTCAGGCACTTAGGGACAACCTGGAACC
TGGGACCTTCGATCTTGGAGGGCTATATGAAGCAATTGAGGAGTGCCTGATTAACGA
TCCCTGGGTTTTGCTTAATGCGTCTTGGTTCAACTCCTTCCTCGCACATGCACTGAAA
TAGTTGTGGCAATGCTACTATTTGCTATCCATACTGTCCAAAAAAGTACCTTGTTTCTA
CT (SEQ ID NO: 6)

AGCGAAAGCAGGCAAACCATTTGAATGGATGTCAATCCGACTTTACTTTTCTTGAAAG
TACCAGTGCAAAATGCTATAAGTACCACCTTCCCTTATACTGGAGACCCTCCATACAG
CCATGGAACAGGGACAGGATACACCATGGACACAGTCAACAGAACACACCAATATTC
AGAAAAGGGGAAGTGGACAACAAACACAGAGACTGGAGCACCCCAACTCAACCCGA
TTGATGGACCACTACCTGAGGATAATGAGCCCAGTGGGTACGCACAAACAGATTGTG
TATTGGAAGCAATGGCTTTCCTTGAAGAATCCCACCCAGGGATCTTTGAAAACTCGT
GTCTTGAAACGATGGAAATTGTTCAACAAACAAGAGTGGATAAACTGACCCAAGGTC
GCCAGACCTATGACTGGACATTGAATAGAAACCAACCGGCTGCAACTGCTTTGGCCA
ACACTATAGAAATCTTCAGATCGAACGGTCTAACAGCCAATGAATCGGGACGGCTAA
TAGATTTCCTCAAGGATGTGATGGAGTCAATGGATAAGGAAGAAATGGAGATAACAA
CACATTTCCAGAGAAAGAGAAGGGTGAGGGACAACATGACCAAGAAAATGGTCACAC
AAAGAACAATAGGGAAGAAAAAACAAAGGCTGAACAAAAAGAGCTACCTGATAAGAG
CACTGACACTGAACACAATGACAAAAGATGCAGAAAGAGGCAAATTGAAGAGGCGAG
CGATTGCAACACCCGGAATGCAAATCAGAGGATTCGTGTACTTTGTTGAAACACTAG
CGAGGAGTATCTGTGAGAAACTTGAGCAATCTGGACTCCCAGTCGGAGGGAATGAG
AAGAAGGCTAAATTGGCAAACGTCGTGAGGAAGATGATGACTAACTCACAAGATACT
GAACTCTCCTTTACAATTACTGGAGACAATACCAAATGGAATGAGAATCAGAATCCTA
GGATGTTTCTGGCAATGATAACGTACATCACAAGGAACCAGCCAGAATGGTTTCGGA
ATGTCTTAAGCATAGCTCCTATAATGTTCTCAAACAAAATGGCGAGACTAGGAAAAGG
ATACATGTTCGAAAGTAAGAGCATGAAGTTACGAACACAAATACCAGCAGAAATGCTT
GCAAACATTGATCTTAAATACTTCAATGAATTAACGAAAAAGAAAATTGAGAAAATAAG
GCCTCTATTAATAGATGGTACAGCCTCATTGAGCCCTGGAATGATGATGGGCATGTT
CAACATGCTGAGTACAGTCCTAGGAGTTTCAATCCTGAATCTTGGACAGAAAAGGTA
CACCAAAACCACATATTGGTGGGACGGACTCCAATCCTCTGATGATTTCGCTCTCAT
CGTAAATGCACCGAATCATGAGGGAATACAAGCAGGAGTGGATAGGTTTTATAGGAC
TTGTAAACTAGTTGGAATCAATATGAGCAAGAAGAAGTCTTACATAAATCGGACAGGG
ACATTTGAATTCACGAGCTTTTTCTACCGCTATGGATTTGTAGCCAATTTCAGTATGG
AGCTGCCCAGTTTTGGAGTGTCTGGAATTAATGAATCGGCCGACATGAGCATTGGTG
TTACAGTGATAAAAAACAATATGATAAACAACGACCTTGGGCCAGCAACAGCTCAGAT
GGCTCTTCAGTTATTCATCAAGGACTACAGATACACATACCGATGCCACAGAGGGGA
TACGCAAATCCAAACAAGGAGATCATTCGAGCTGAAGAAGCTGTGGGAGCAAACCC
GTTCAAAGGCAGGACTGTTGGTTTCAGATGGAGGACCAAATCTATACAATATCCGAA
ACCTCCATATTCCTGAAGTCTGCTTAAAATGGGAATTGATGGATGAAGATTACCAGGG
CAGACTGTGTAATCCTCTGAATCCATTCGTCAGCCATAAGGAAATTGAATCTGTCAAC
AATGCTGTAGTAATGCCAGCTCATGGCCCGGCCAAGAGTATGGAATATGATGCCGTT
GCAACTACACATTCATGGATTCCTAAAAGGAACCGTTCCATTCTCAATACGAGTCAAA
GGGGAATTCTTGAGGATGAACAGATGTACCAGAAGTGCTGCAATCTATTCGAGAAAT
TCTTCCCCAGCAGTTCATATCGGAGGCCAGTTGGAATTTCCAGCATGGTGGAGGCCA
TGGTGTCTAGGGCCCGAATTGACGCACGAATCGATTTCGAGTCTGGAAGGATTAAGA
AAGAAGAGTTTGCCGAGATCATGAAGATCTGTTCCACCATTGAAGAACTCAGACGGC
AAAAATAGTGAATTTAGCTTGTCCTTCGTGAAAAAATGCCTTGTTTCTACT (SEQ ID NO: 7)

Figure 3 (cont'd)

PB2
AGCGAAAGCAGGTCAAATATATTCAATATGGAGAGGATAAAAGAATTACGAGATCTAA
TGTCACAGTCCCGCACTCGCGAGATACTAACAAAAACCACTGTGGACCATATGGCCA
TAATCAAGAAATACACATCAGGAAGACAAGAGAAGAACCCTGCTCTCAGAATGAAAT
GGATGATGGCAATGAAATATCCAATCACAGCGGACAAGAGAATAATAGAGATGATTC
CTGAAAGGAATGAACAAGGGCAGACGCTCTGGAGCAAGACAAATGATGCTGGATCG
GACAGGGTGATGGTGTCTCCCCTAGCTGTAACTTGGTGGAATAGGAATGGGCCGGC
GACAAGTGCAGTTCATTATCCAAAGGTTTACAAAACATACTTTGAGAAGGTTGAAAGA
TTAAAACATGGAACCTTCGGTCCCGTTCATTTCCGAAACCAGGTTAAAATACGCCGC
CGAGTTGATATAAATCCTGGCCATGCAGATCTCAGTGCTAAAGAAGCACAAGATGTC
ATCATGGAGGTCGTTTTCCCAAATGAAGTGGGAGCTAGAATATTGACATCAGAGTCG
CAATTGACAATAACGAAAGAGAAGAAAGAAGAGCTCCAAGATTGTAAGATTGCTCCC
TTAATGGTTGCATACATGTTGGAAAGGGAACTGGTCCGCAAGACCAGATTCCTACCG
GTAGCAGGCGGAACAAGTAGTGTGTACATTGAGGTATTGCATTTGACTCAAGGGACC
TGCTGGGAACAGATGTACACTCCAGGCGGAGAAGTGAGAAATGACGATGTTGACCA
GAGTTTGATCATTGCTGCCAGAAACATTGTTAGGAGAGCAACAGTATCAGCGGATCC
ACTGGCATCACTGCTGGAGATGTGTCACAGCACACAAATTGGTGGGATAAGGATGGT
GGACATCCTTAGGCAAAATCCAACTGAGGAACAAGCTGTGGATATATGCAAAGCAGC
AATGGGTCTTAGGATCAGTTCTTCCTTTAGCTTTGGAGGCTTCACTTTCAAAAGAACA
AGTGGATCATCCGTCAAGAAGGAAGAGGAAGTGCTTACAGGCAACCTCCAAACATTG
AAAATAAGAGTACATGAGGGGTATGAGGAATTCACAATGGTTGGGCGGAGGGCAAC
AGCTATCCTGAGGAAAGCAACTAGAAGGCTGATTCAGTTGATAGTAAGTGGAAGAGA
CCAACAATCAATCGCTGAGGCAATCATTGTAGCAATGGTGTTCTCACAGGAGGATTG
CATGATAAAGGCAGTCCGAGGCGATCTGAATTTCGTAAACAGAGCAAACCAAAGATT
AAACCCCATGCATCAACTCCTGAGACATTTTCAAAAGGACGCAAAAGTGCTATTTCAG
AATTGGGGAATTGAACCCATTGATAATGTCATGGGGATGATCGGAATATTACCTGACA
TGACTCCCAGCACAGAAATGTCACTGAGAGGAGTAAGAGTTAGTAAAATGGGAGTGG
ATGAATATTCCAGCACTGAGAGAGTAGTTGTAAGTATTGACCGTTTCTTAAGGGTTCG
AGATCAGCGGGGGAACGTACTCTTATCTCCCGAAGAGGTCAGCGAAACCCAGGGAA
CAGAGAAATTGACAATAACATATTCATCATCAATGATGTGGGAAATCAACGGTCCTGA
GTCAGTGCTTGTTAACACCTATCAGTGGATCATCAGAAACTGGGAGACTGTGAAGAT
TCAATGGTCTCAAGACCCCACGATGCTGTACAATAAGATGGAGTTTGAACCGTTCCA
ATCCTTGGTACCCAAAGCTGCCAGAGGTCAATACAGTGGATTTGTGAGAACATTATTC
CAGCAAATGCGTGACGTACTGGGGACATTTGATACTGTCCAGATAATAAAGCTGCTA
CCATTTGCAGCAGCCCCACCGAAGCAGAGCAGAATGCAGTTTTCTTCTCTAACTGTG
AATGTGAGAGGCTCAGGAATGAGAATACTCGTAAGGGGCAATTCCCCTGTGTTCAAC
TACAATAAGGCAACCAAAAGGCTTACCGTCCTTGGAAAGGACGCAGGTGCATTAACA
GAGGATCCGGATGAAGGGACAGCCGGAGTGGAGTCTGCAGTACTGAGGGGATTCTT
AATTTTAGGCAAGGAGGACAAAAGGTATGGACCAGCATTGAGCATCAATGAACTGAG
CAATCTTGCGAAGGGGGAGAAAGCTAATGTGCTGATAGGGCAAGGTGACGTGGTGT
TGGTAATGAAACGAAAACGGGACTCTAGCATACTTACTGACAGCCAGACAGCGACCA
AAAGAATTCGGATGGCCATCAATTAGTGTCGAATTGTTTAAAAACGACCTTGTTTCTA
CT (SEQ ID NO: 8)

Figure 3 (cont'd)

FIGURE 4
A/AnHui/1/05 Attenuated Strain Gene Sequences

HA
AGCAAAAGCAGGGGTTCAATCTGTCAAAATGGAGAAAATAGTGCTTCTTCTTGCAATA
GTCAGCCTTGTTAAAAGTGATCAGATTTGCATTGGTTACCATGCAAACAACTCGACAG
AGCAGGTTGACACAATAATGGAAAAGAACGTTACTGTTACACATGCCCAAGACATACT
GGAAAAGACACACAACGGGAAGCTCTGCGATCTAGATGGAGTGAAGCCTCTGATTTT
AAGAGATTGTAGTGTAGCTGGATGGCTCCTCGGAAACCCAATGTGTGACGAATTCAT
CAATGTGCCGGAATGGTCTTACATAGTGGAGAAGGCCAACCCAGCCAATGACCTCTG
TTACCCAGGGAATTTCAACGACTATGAAGAACTGAAACACCTATTGAGCAGAATAAAC
CATTTTGAGAAAATTCAGATCATCCCCAAAAGTTCTTGGTCCGATCATGAAGCCTCAT
CAGGGGTGAGCTCAGCATGTCCATACCAGGGAACGCCCTCCTTTTTCAGAAATGTGG
TATGGCTTATCAAAAGAACAATACATACCCAACAATAAAGAGAAGCTACAATAATAC
CAACCAGGAAGATCTTTTGATACTGTGGGGGATTCATCATTCTAATGATGCGGCAGA
GCAGACAAAGCTCTATCAAAACCCAACCACCTATATTTCCGTTGGGACATCAACACTA
AACCAGAGATTGGTACCAAAAATAGCTACTAGATCCAAAGTAAACGGGCAAAGTGGA
AGGATGGATTTCTTCTGGACAATTTTAAAACCGAATGATGCAATCAACTTCGAGAGTA
ATGGAAATTTCATTGCTCCAGAATATGCATACAAAATTGTCAAGAAGGGGACTCAGC
AATTGTTAAAAGTGAAGTGGAATATGGTAACTGCAACACAAAGTGTCAAACTCCAATA
GGGGCGATAAACTCTAGTATGCCATTCCACAACATACACCCTCTCACCATCGGGGAA
TGCCCCAAATATGTGAAATCAAACAAATTAGTCCTTGCGACTGGGCTCAGAAATAGTC
CTCAAACCGAGACCCGAGGACTATTTGGAGCTATAGCAGGGTTTATAGAGGGAGGAT
GGCAGGGAATGGTAGATGGTTGGTATGGGTACCACCATAGCAATGAGCAGGGGAGT
GGGTACGCTGCAGACAAAGAATCCACTCAAAAGGCAATAGATGGAGTCACCAATAAG
GTCAACTCGATCATTGACAAAATGAACACTCAGTTTGAGGCCGTTGGAAGGGAATTT
AATAACTTAGAAAGGAGAATAGAGAATTTAAACAAGAAAATGGAAGACGGATTCCTAG
ATGTCTGGACTTATAATGCTGAACTTCTGGTTCTCATGGAAAATGAGAGAACTCTAGA
CTTCCATGATTCAAATGTCAAGAACCTTTACGACAAGGTCCGACTACAGCTTAGGGAT
AATGCAAAGGAGCTGGGTAACGGTTGTTTCGAGTTCTATCACAAATGTGATAATGAAT
GTATGGAAAGTGTAAGAAACGGAACGTATGACTACCCGCAGTATTCAGAAGAAGCAA
GATTAAAAAGAGAGGAAATAAGTGGAGTAAAATTGGAATCAATAGGAACTTACCAAAT
ACTGTCAATTTATTCAACAGTTGCGAGTTCTCTAGCACTGGCAATCATGGTGGCTGGT
CTATCTTTGTGGATGTGCTCCAATGGGTCGTTACAATGCAGAATTTGCATTTAAATTT
GTGAGTTCAGATTGTAGTTAAAAACACCCTTGTTTCTACT (SEQ ID NO: 11)

NA
```
AGCAAAAGCAGGAGTTCAAAATGAATCCAAATCAGAAGATAATAACCATTGGGTCAAT
CTGTATGGTAATTGGAATAGTTAGCTTAATGTTACAAATTGGGAACATGATCTCAATAT
GGGTCAGTCATTCAATTCAAACAGGGAATCAACACCAAGCTGAACCAATCAGAAATG
CTAATTTTCTTACTGAGAACGCTGTGGCTTCAGTAACATTAGCGGGCAATTCATCTCT
TTGCCCCGTTAGAGGATGGGCTGTACACAGTAAAGACAACAGTATAAGGATTGGTTC
CAAGGGGGATGTTTTGTTATTAGAGAGCCGTTCATCTCATGCTCCCACTTGGAATG
CAGAACTTTCTTTTTGACTCAGGGAGCCTTACTGAATGACAAGCACTCCAATGGGACT
GTCAAAGACAGAAGCCCTCACAGAACATTAATGAGTTGTCCTGTGGGTGAGGCTCCC
TCCCCATATAACTCAAGGTTTGAGTCTGTTGCTTGGTCAGCAAGTGCTTGCCATGATG
GCACCAGTTGGTTGACAATTGGAATTTCTGGCCCAGACAATGGGGCTGTGGCTGTAT
TGAAATACAATGGCATAATAACAGACACTATCAAGAGTTGGAGGAACAACATACTGAG
AACTCAAGAGTCTGAATGTGCATGTGTAAATGGCTCTTGCTTTACTGTAATGACTGAT
GGACCAAGTAATGGGCAGGCATCATATAAGATCTTCAAAATGGAAAAGGGAAAGTG
GTTAAATCAGTCGAATTGAATGCTCCTAATTATCACTATGAGGAATGCTCCTGTTATC
CTGATGCTGGCGAAATCACATGTGTGTGCAGGGATAATTGGCATGGCTCGAATAGGC
CATGGGTATCTTTCAATCAGAATTTGGAGTATCAAATAGGATATATATGCAGTGGAGT
TTTCGGAGACAATCCACGCCCCAATGATGGAACAGGTAGTTGTGGTCCAGTGTCCCC
TAACGGGGCATATGGGATAAAAGGGTTTTCATTTAAATACGGCAATGGTGTTTGGATC
GGAAGAACCAAAAGCACTAATTCCAGGAGCGGCTTTGAAATGATTTGGGATCCAAAT
GGGTGGACTGAAACGGACAGTAACTTTTCGGTGAAACAAGATATAGTAGCAATAACT
GATTGGTCAGGATATAGCGGGAGTTTTGTCCAGCATCCAGAACTGACAGGATTAGAT
TGCATAAGACCTTGCTTCTGGGTTGAGTTAATCAGAGGGCGGCCCAAAGAGAGCACA
ATTTGGACTAGTGGGAGCAGCATATCTTTTTGTGGTGTAAATAGTGACACTGTGAGTT
GGTCTTGGCCAGACGGTGCTGAGTTGCCATTCACCATTGACAAGTAGTTTGTTCAAA
AAACTCCTTGTTTCTACT (SEQ ID NO: 12)
```

M
```
AGCAAAAGCAGGTAGATGTTGAAAGATGAGTCTTCTAACCGAGGTCGAAACGTACGT
TCTCTCTATCATCCCGTCAGGCCCCCTCAAAGCCGAGATCGCACAGAAACTTGAAGA
TGTCTTTGCAGGAAAGAACACCGATCTCGAGGCTCTCATGGAGTGGCTAAAGACAAG
ACCAATCCTGTCACCTCTGACTAAAGGGATTTTGGGATTTGTATTCACGCTCACCGTG
CCCAGTGAGCGAGGACTGCAGCGTAGACGCTTTGTCCAGAATGCCCTAAATGGAAA
TGGAGATCCAAATAATATGGATAGGGCAGTTAAGCTATATAAGAAGCTGAAAAGAGA
AATAACATTCCATGGGGCTAAGGAGGTCGCACTCAGCTACTCAACCGGTGCACTTGC
CAGTTGCATGGGTCTCATATACAACAGGATGGGAACGGTGACTACGGAAGTGGCTTT
TGGCCTAGTGTGTGCCACTTGTGAGCAGATTGCAGATTCACAGCATCGGTCTCACAG
ACAGATGGCAACTATCACCAACCCACTAATCAGACATGAGAACAGAATGGTGCTGGC
CAGCACTACAGCTAAGGCTATGGAGCAGATGGCGGGATCAAGTGAGCAGGCAGCG
GAAGCCATGGAGATCGCTAATCAGGCTAGGCAGATGGTGCAGGCAATGAGGACAAT
TGGGACTCATCCTAACTCTAGTGCTGGTCTGAGAGATAATCTTCTTGAAAATTTGCAG
GCCTACCAGAAACGAATGGGAGTGCAGATGCAGCGATTCAAGTGATCCTATTGTTGT
TGCCGCAAATATCATTGGGATCTTGCACTTGATATTGTGGATTCTTGATCGTCTTTTCT
TCAAATGCATTTATCGTCGCCTTAAATACGGTTTGAAAAGAGGGCCTGCTACGGCAG
GGGTACCTGAGTCTATGAGGGAAGAGTACCGGCAGGAACAGCAGAGTGCTGTGGAT
GTTGACGATGGTCATTTTGTCAACATAGAATTGGAGTAAAAAACTACCTTGTTTCTACT
(SEQ ID NO: 3)
```

Figure 4 (cont'd)

NS
AGCAAAAGCAGGGTGACAAAAACATAATGGATTCCAACACTGTGTCAAGCTTTCAGG
TAGACTGCTTTCTTTGGCATGTCCGCAAACGATTTGCAGACCAAGAACTGGGTGATG
CCCCATTCCTTGACCGGCTTCGCCGAGATCAGAAGTCCCTAAGAGGAAGAGGCAAC
ACTCTTGGTCTGGACATCGAAACAGCTACTCGCGCAGGAAAGCAGATAGTGGAGCG
GATTCTGGAGGGGGAGTCTGATAAGGCACTTAAAATGCCGGCTTCACGCTACCTAAC
TGACATGACTCTCGAAGAAATGTCAAGGGACTGGTTCATGCTCATGCCCAAGCAGAA
AGTGGCAGGTTCCCTTTGCATCAAAATGGACCAGGCAATAATGGATAAAACCATCAT
ATTGAAAGCAAACTTCAGTGTGATTTTTGACCGGTTGGAAACCCTAATACTACTTAGA
GCTTTCACAGAAGAAGGAGCAATCGTGGGAGAAATCTCACCATTACCTTCTCTTCCA
GGACATACTGGTGAGGATGTCAAAAATGCAATTGGCGTCCTCATCGGAGGACTTGAA
TGGAATGATAACACAGTTCGAGTCACTGAAACTATACAGAGATTCGCTTGGAGAAAC
AGTGATGAGGATGGGAGACTTCCACTCCCTCCAAATCAGAAACGGTAAATGGCGAGA
ACAATTGAGTCAGAAGTTTGAAGAAATAAGGTGGCTGATTGAAGAAGTAAGACATAG
ATTGAAAATTACAGAAAACAGCTTCGAACAGATAACGTTTATGCAAGCCTTACAACTA
CTGCTTGAAGTGGAGCAAGAGATAAGAGCCTTCTCGTTTCAGCTTATTTAATGATAAA
AAACACCCTTGTTTCTACT (SEQ ID NO: 4)

NP
AGCAAAAGCAGGGTAGATAATCACTCACCGAGTGACATCAGCATCATGGCGTCTCAA
GGCACCAAACGATCTTATGAACAGATGGAAACTGGTGGGAACGCCAGAATGCTACT
GAGATCAGGGCATCTGTTGGAAGAATGGTTAGTGGCATTGGGAGGTTCTACATACAG
ATGTGCACAGAACTCAAACTCAGTGACTATGAAGGGAGGCTGATCCAGAACAGCATA
ACAATAGAGAGAATGGTACTCTCTGCATTTGATGAAAGAAGGAACAGATACCTGGAA
GAACACCCCAGTGCGGGAAAGGACCCGAAGAAGACTGGAGGTCCAATTTATCGGAG
GAGAGACGGGAAATGGGTGAGAGAGCTAATTCTGTACGACAAAGAGGAGATCAGGA
GGATTTGGCGTCAAGCGAACAATGGAGAGGACGCAACTGCTGGTCTTACCCACCTG
ATGATATGGCATTCCAATCTAAATGATGCCACATATCAGAGAACGAGAGCTCTCGTG
CGTACTGGAATGGACCCAAGGATGTGCTCTCTGATGCAAGGGTCAACTCTCCCGAG
GAGATCTGGAGCTGCCGGTGCAGCAGTAAAGGGGGTAGGGACAATGGTGATGGAG
CTGATTCGGATGATAAAACGAGGGATCAACGACCGGAATTTCTGGAGAGGCGAAAAT
GGAAGAAGAACAAGGATTGCATATGAGAGAATGTGCAACATCCTCAAAGGGAAATTC
CAAACAGCAGCACAAAGAGCAATGATGGATCAAGTGCGAGAGAGCAGAAATCCTGG
GAATGCTGAAATTGAAGATCTCATTTTTCTGGCACGGTCTGCACTCATCCTGAGAGG
ATCAGTGGCCCATAAGTCCTGCTTGCCTGCTTGTGTGTACGGACTTGCAGTGGCCAG
TGGATATGACTTTGAGAGAGAAGGGTACTCTCTGGTTGGAATAGATCCTTTCCGCCT
GCTTCAAAACAGCCAGGTCTTTAGTCTCATTAGACCAAATGAGAATCCAGCACATAAG
AGTCAATTAGTGTGGATGGCATGCCACTCTGCAGCATTTGAGGACCTTAGAGTCTCA
AGTTTCATCAGAGGGACAAGAGTGGTCCCAAGAGGACAGCTATCCACCAGAGGGT
TCAAATTGCTTCAAATGAGAACATGGAGGCAATGGACTCCAACACTCTTGAACTGAG
AAGCAGATATTGGGCTATAAGAACCAGAAGCGGAGGAAACACCAACCAGCAGAGGG
CATCTGCAGGACAGATCAGCGTTCAGCCCACTTTCTCGGTCCAGAGAAACCTTCCCT
TCGAAAGAGCGACCATTATGGCAGCATTTACAGGAAATACTGAGGGCAGAACGTCTG
ACATGAGGACTGAAATCATAAGAATGATGGAAAGTGCCAGACCAGAAGATGTGTCAT
TCCAGGGGCGGGGAGTCTTCGAGCTCTCGGACGAAAAGGCAACGAACCCGATCGT
GCCTTCCTTTGACATGAATAATGAAGGATCTTATTTCTTCGGAGACAATGCAGAGGAG
TATGACAATTAAAGAAAAATACCCTTGTTTCTACT (SEQ ID NO: 5)

Figure 4 (cont'd)

PA
AGCGAAAGCAGGTACTGATCCAAAATGGAAGACTTTGTGCGACAATGCTTCAATCCA
ATGATTGTCGAGCTTGCGGAAAAGGCAATGAAAGAATATGGGGAAGATCCGAAAATC
GAAACGAACAAGTTTGCTGCAATATGCACACACTTGGAGGTCTGTTTCATGTATTCGG
ATTTTCACTTTATTGATGAACGGAGTGAATCAATAATTGTAGAATCTGGAGATCCGAA
TGCATTATTGAAACACCGATTTGAAATAATTGAAGGAAGAGACCGAACGATGGCCTG
GACTGTGGTGAATAGTATCTGCAACACCACAGGAGTTGAGAAACCTAAATTTCTCCC
AGATTTGTATGACTACAAAGAGAACCGATTCATCGAAATTGGAGTGACACGGAGGGA
AGTTCATACATACTATCTGGAGAAAGCCAACAAGATAAAATCCGAGGAGACACATATT
CACATATTCTCATTCACAGGGGAGGAAATGGCCACCAAAGCGGACTACACCCTTGAT
GAAGAGAGCAGGGCAAGAATTAAAACCAGGCTGTTCACCATAAGGCAGGAAATGGC
CAGTAGGGGTCTATGGGATTCCTTTCGTCAATCCGAGAGAGGCGAAGAGACAATTGA
AGAAAAATTTGAAATCACTGGAACCATGCGCAGACTTGCAGACCAAAGTCTCCCACC
GAACTTCTCCAGCCTTGAAAACTTTAGAGCCTATGTGGATGGATTCGAACCGAACGG
CTGCATTGAGGGCAAGCTTTCTCAAATGTCAAAGAAGTGAATGCTAGAATTGAGCC
ATTTTTGAAGACAACGCCACGCCCTCTCAGACTACCTGATGGGCCTCCTTGCTCTCA
GCGGTCGAAGTTCTTGCTGATGGATGCCCTTAAATTAAGCATCGAAGACCCGAGTCA
TGAGGGGGAGGGGATACCACTATACGATGCAATCAAATGCATGAAGACATTTTTCGG
CTGGAAAGAGCCCAACATCGTGAAACCACATGAAAAGGTATAAACCCCAATTACCT
CCTGGCTTGGAAGCAAGTGCTGGCAGAACTCCAAGATATTGAAAATGAGGAGAAAAT
CCCAAAAACAAAGAACATGAAAAAAACAAGCCAGTTGAAGTGGGCACTCGGTGAGAA
CATGGCACCAGAGAAAGTAGACTTTGAGGACTGCAAAGATGTTAGCGATCTAAGACA
GTATGACAGTGATGAACCAGAGTCTAGATCACTAGCAAGCTGGATTCAGAGTGAATT
CAACAAGGCATGTGAATTGACAGATTCGATTTGGATTGAACTCGATGAAATAGGAGA
AGACGTAGCTCCAATTGAGCACATTGCAAGTATGAGAAGGAACTATTTTACAGCGGA
AGTATCCCATTGCAGGGCCACTGAATACATAATGAAGGGAGTGTACATAAACACAGC
CCTGTTGAATGCATCCTGTGCAGCCATGGATGACTTTCAACTGATTCCAATGATAAGC
AAATGCAGAACCAAAGAAGGAAGACGGAAAACTAATCTGTATGGATTCATTATAAAAG
GGAGATCCCACTTGAGGAATGATACCGATGTGGTAAATTTTGTGAGTATGGAATTCTC
TCTTACTGATCCGAGGCTGGAGCCACACAAGTGGGAAAAGTACTGTGTCCTCGAGAT
AGGAGACATGCTCCTCCGGACTGCAGTAGGCCAAGTTTCGAGGCCCATGTTCCTGT
ATGTAAGAACCAATGGAACCTCCAAGATCAAAATGAAATGGGGCATGGAAATGAGGC
GATGCCTTCTTCAATCCCTTCAACAAATTGAAAGCATGATTGAAGCCGAGTCTTCTGT
CAAAGAGAAGGACATGACCAAAGAATTCTTTGAAAACAAATCAGAAACATGGCCGATT
GGAGAGTCCCCCAAGGGAGTGGAGGAAGGCTCCATCGGAAAGGTGTGCAGAACCTT
GCTGGCGAAGTCTGTGTTCAACAGTTTATATGCATCTCCACAACTCGAGGGGTTTTC
AGCTGAATCAAGAAAATTGCTTCTCATTGCTCAGGCACTTAGGGACAACCTGGAACC
TGGGACCTTCGATCTTGGAGGGCTATATGAAGCAATTGAGGAGTGCCTGATTAACGA
TCCCTGGGTTTTGCTTAATGCGTCTTGGTTCAACTCCTTCCTCGCACATGCACTGAAA
TAGTTGTGGCAATGCTACTATTTGCTATCCATACTGTCCAAAAAAGTACCTTGTTTCTA
CT (SEQ ID NO: 6)

Figure 4 (cont'd)

PB1
<u>AGCGAAAGCAGGCAAACCATTTGAATGG</u>ATGTCAATCCGACTTTACTTTTCTTGAAAG
TACCAGTGCAAAATGCTATAAGTACCACCTTCCCTTATACTGGAGACCCTCCATACAG
CCATGGAACAGGGACAGGATACACCATGGACACAGTCAACAGAACACACCAATATTC
AGAAAAGGGGAAGTGGACAACAAACACAGAGACTGGAGCACCCCAACTCAACCCGA
TTGATGGACCACTACCTGAGGATAATGAGCCCAGTGGGTACGCACAAACAGATTGTG
TATTGGAAGCAATGGCTTTCCTTGAAGAATCCCACCCAGGGATCTTTGAAAACTCGT
GTCTTGAAACGATGGAAATTGTTCAACAAACAAGAGTGGATAAACTGACCCAAGGTC
GCCAGACCTATGACTGGACATTGAATAGAAACCAACCGGCTGCAACTGCTTTGGCCA
ACACTATAGAAATCTTCAGATCGAACGGTCTAACAGCCAATGAATCGGGACGGCTAA
TAGATTTCCTCAAGGATGTGATGGAGTCAATGGATAAGGAAGAAATGGAGATAACAA
CACATTTCCAGAGAAAGAGAAGGGTGAGGGACAACATGACCAAGAAAATGGTCACAC
AAAGAACAATAGGGAAGAAAAAACAAAGGCTGAACAAAAAGAGCTACCTGATAAGAG
CACTGACACTGAACACAATGACAAAAGATGCAGAAAGAGGCAAATTGAAGAGGCGAG
CGATTGCAACACCCGGAATGCAAATCAGAGGATTCGTGTACTTTGTTGAAACACTAG
CGAGGAGTATCTGTGAGAAACTTGAGCAATCTGGACTCCCAGTCGGAGGGAATGAG
AAGAAGGCTAAATTGGCAAACGTCGTGAGGAAGATGATGACTAACTCACAAGATACT
GAACTCTCCTTTACAATTACTGGAGACAATACCAAATGGAATGAGAATCAGAATCCTA
GGATGTTTCTGGCAATGATAACGTACATCACAAGGAACCAGCCAGAATGGTTTCGGA
ATGTCTTAAGCATAGCTCCTATAATGTTCTCAAACAAAATGGCGAGACTAGGAAAAGG
ATACATGTTCGAAAGTAAGAGCATGAAGTTACGAACACAAATACCAGCAGAAATGCTT
GCAAACATTGATCTTAAATACTTCAATGAATTAACGAAAAAGAAAATTGAGAAAATAAG
GCCTCTATTAATAGATGGTACAGCCTCATTGAGCCCTGGAATGATGATGGGCATGTT
CAACATGCTGAGTACAGTCCTAGGAGTTTCAATCCTGAATCTTGGACAGAAAAGGTA
CACCAAACCACATATTGGTGGGACGGACTCCAATCCTCTGATGATTTCGCTCTCAT
CGTAAATGCACCGAATCATGAGGGAATACAAGCAGGAGTGGATAGGTTTTATAGGAC
TTGTAAACTAGTTGGAATCAATATGAGCAAGAAGAAGTCTTACATAAATCGGACAGGG
ACATTTGAATTCACGAGCTTTTTCTACCGCTATGGATTTGTAGCCAATTTCAGTATGG
AGCTGCCCAGTTTTGGAGTGTCTGGAATTAATGAATCGGCCGACATGAGCATTGGTG
TTACAGTGATAAAAAACAATATGATAAACAACGACCTTGGGCCAGCAACAGCTCAGAT
GGCTCTTCAGTTATTCATCAAGGACTACAGATACACATACCGATGCCACAGAGGGGA
TACGCAAATCCAAACAAGGAGATCATTCGAGCTGAAGAAGCTGTGGGAGCAAACCC
GTTCAAAGGCAGGACTGTTGGTTTCAGATGGAGGACCAAATCTATACAATATCCGAA
ACCTCCATATTCCTGAAGTCTGCTTAAAATGGGAATTGATGGATGAAGATTACCAGGG
CAGACTGTGTAATCCTCTGAATCCATTCGTCAGCCATAAGGAAATTGAATCTGTCAAC
AATGCTGTAGTAATGCCAGCTCATGGCCCGGCCAAGAGTATGGAATATGATGCCGTT
GCAACTACACATTCATGGATTCCTAAAAGGAACCGTTCCATTCTCAATACGAGTCAAA
GGGGAATTCTTGAGGATGAACAGATGTACCAGAAGTGCTGCAATCTATTCGAGAAAT
TCTTCCCCAGCAGTTCATATCGGAGGCCAGTTGGAATTTCCAGCATGGTGGAGGCCA
TGGTGTCTAGGGCCCGAATTGACGCACGAATCGATTTCGAGTCTGGAAGGATTAAGA
AAGAAGAGTTTGCCGAGATCATGAAGATCTGTTCCACCATTGAAGAACTCAGACGGC
AAAAATAGTGAATTTAGC<u>TTGTCCTTCGTGAAAAAATGCCTTGTTTCTACT</u> (SEQ ID NO: 7)

AGCGAAAGCAGGTCAAATATATTCAATATGGAGAGGATAAAAGAATTACGAGATCTAA
TGTCACAGTCCCGCACTCGCGAGATACTAACAAAAACCACTGTGGACCATATGGCCA
TAATCAAGAAATACACATCAGGAAGACAAGAGAAGAACCCTGCTCTCAGAATGAAAT
GGATGATGGCAATGAAATATCCAATCACAGCGGACAAGAGAATAATAGAGATGATTC
CTGAAAGGAATGAACAAGGGCAGACGCTCTGGAGCAAGACAAATGATGCTGGATCG
GACAGGGTGATGGTGTCTCCCCTAGCTGTAACTTGGTGGAATAGGAATGGGCCGGC
GACAAGTGCAGTTCATTATCCAAAGGTTTACAAAACATACTTTGAGAAGGTTGAAAGA
TTAAAACATGGAACCTTCGGTCCCGTTCATTTCCGAAACCAGGTTAAAATACGCCGC
CGAGTTGATATAAATCCTGGCCATGCAGATCTCAGTGCTAAAGAAGCACAAGATGTC
ATCATGGAGGTCGTTTTCCCAAATGAAGTGGGAGCTAGAATATTGACATCAGAGTCG
CAATTGACAATAACGAAAGAGAAGAAAGAAGAGCTCCAAGATTGTAAGATTGCTCCC
TTAATGGTTGCATACATGTTGGAAAGGGAACTGGTCCGCAAGACCAGATTCCTACCG
GTAGCAGGCGGAACAAGTAGTGTGTACATTGAGGTATTGCATTTGACTCAAGGGACC
TGCTGGGAACAGATGTACACTCCAGGCGGAGAAGTGAGAAATGACGATGTTGACCA
GAGTTTGATCATTGCTGCCAGAAACATTGTTAGGAGAGCAACAGTATCAGCGGATCC
ACTGGCATCACTGCTGGAGATGTGTCACAGCACACAAATTGGTGGGATAAGGATGGT
GGACATCCTTAGGCAAAATCCAACTGAGGAACAAGCTGTGGATATATGCAAAGCAGC
AATGGGTCTTAGGATCAGTTCTTCCTTTAGCTTTGGAGGCTTCACTTTCAAAAGAACA
AGTGGATCATCCGTCAAGAAGGAAGAGGAAGTGCTTACAGGCAACCTCCAAACATTG
AAAATAAGAGTACATGAGGGGTATGAGGAATTCACAATGGTTGGCGGAGGGCAAC
AGCTATCCTGAGGAAAGCAACTAGAAGGCTGATTCAGTTGATAGTAAGTGGAAGAGA
CCAACAATCAATCGCTGAGGCAATCATTGTAGCAATGGTGTTCTCACAGGAGGATTG
CATGATAAAGGCAGTCCGAGGCGATCTGAATTTCGTAAACAGAGCAAACCAAAGATT
AAACCCCATGCATCAACTCCTGAGACATTTTCAAAAGGACGCAAAAGTGCTATTTCAG
AATTGGGGAATTGAACCCATTGATAATGTCATGGGGATGATCGGAATATTACCTGACA
TGACTCCCAGCACAGAAATGTCACTGAGAGGAGTAAGAGTTAGTAAAATGGGAGTGG
ATGAATATTCCAGCACTGAGAGAGTAGTTGTAAGTATTGACCGTTTCTTAAGGGTTCG
AGATCAGCGGGGGAACGTACTCTTATCTCCCGAAGAGGTCAGCGAAACCCAGGGAA
CAGAGAAATTGACAATAACATATTCATCATCAATGATGTGGGAAATCAACGGTCCTGA
GTCAGTGCTTGTTAACACCTATCAGTGGATCATCAGAAACTGGGAGACTGTGAAGAT
TCAATGGTCTCAAGACCCCACGATGCTGTACAATAAGATGGAGTTTGAACCGTTCCA
ATCCTTGGTACCCAAAGCTGCCAGAGGTCAATACAGTGGATTTGTGAGAACATTATTC
CAGCAAATGCGTGACGTACTGGGGACATTTGATACTGTCCAGATAATAAAGCTGCTA
CCATTTGCAGCAGCCCCACCGAAGCAGAGCAGAATGCAGTTTTCTTCTCTAACTGTG
AATGTGAGAGGCTCAGGAATGAGAATACTCGTAAGGGCAATTCCCCTGTGTTCAAC
TACAATAAGGCAACCAAAAGGCTTACCGTCCTTGGAAAGGACGCAGGTGCATTAACA
GAGGATCCGGATGAAGGGACAGCCGGAGTGGAGTCTGCAGTACTGAGGGGATTCTT
AATTTTAGGCAAGGAGGACAAAAGGTATGGACCAGCATTGAGCATCAATGAACTGAG
CAATCTTGCGAAGGGGGAGAAAGCTAATGTGCTGATAGGGCAAGGTGACGTGGTGT
TGGTAATGAAACGAAAACGGGACTCTAGCATACTTACTGACAGCCAGACAGCGACCA
AAAGAATTCGGATGGCCATCAATTAGTGTCGAATTGTTTAAAAACGACCTTGTTTCTA
CT (SEQ ID NO: 8)

Figure 4 (cont'd)

PRODUCTION OF VIRAL VACCINE

This application claims the priority benefit of U.S. Provisional Patent Application No. 61/122,961, filed Dec. 16, 2008, hereby incorporated by reference.

FIELD OF THE INVENTION

The present invention relates, in general, to materials and methods for production of an improved vaccine against influenza virus. The invention provides a reassortant virus expressing hemagglutinin and neuraminidase from single strain of virus, e.g., an H5N1 strain of influenza A and also having all internal genes from an influenza strain. It is contemplated that the hemagglutinin gene is mutated to exhibit decreased pathogenicity compared to the hemagglutinin gene in the wild type strain.

BACKGROUND OF THE INVENTION

Efficient vaccine production requires the growth of large quantities of virus produced in high yields from a host system. Different types of virus require different growth conditions in order to obtain acceptable yields. The host in which the virus is grown is therefore of great significance. As a function of the virus type, a virus may be grown in primary tissue culture cells, established cell lines or in embryonated eggs, such as those from chickens.

Some of the mammalian cell lines which are used as viral host systems produce virus at high yields, but the tumorigenic nature of such cells invokes regulatory constraints against their use for vaccine production. In fact, the applicable guidelines of the World Health Organization (WHO) indicate that only a few cell lines are allowed for virus vaccine production.

There are three general types of influenza viruses, Type A, Type B and Type C, which are defined by the absence of serological crossreactivity between their internal proteins. Influenza Type A viruses are further classified into sub-types based on antigenic differences of their glycoproteins, the hemagglutinin (HA) and neuraminidase (NA) proteins. Humans are susceptible to diseases caused by infection with each of influenza Type A, B, and C viruses.

Currently, the most significant causes of influenza infections in humans are those attributable to Type B and to subtypes H1N1 and H3N2 of influenza type A. Accordingly, antigens of Type B and of subtypes H1N1 and H3N2 of influenza Type A are those which are generally incorporated into present seasonal influenza vaccines. The vaccines currently available have protection rates ranging from 75-90%. However, influenza strains that may cause pandemic infection are, for instance, of the H5N1 subtype which are not protected against by typical influenza vaccines. H2, H7 and H9 subtypes also have pandemic potential. See for example Koopmans et al., Lancet 363:587-93, 2004; Joseph et al., Md Med. 6:30-2, 2005; Cameron et al., virology 278:36-41, 2000; and Huber et al., Pediatri Infect Dis 27(10 Suppl): S113-17, 2008.

Live attenuated influenza virus vaccines have recently been approved for use in the United States. Many current vaccines are for seasonal influenza infection and contain two components of influenza A, H1N1 and H3N2, and an influenza B component. Over the last several years, at least one of the components was changed each year due to antigenic drift and mutation in the influenza proteins. Clinical isolates of human influenza virus are taken from infected patients and are reassorted in embryonated chicken eggs with a laboratory-adapted master strain of high-growth donor virus, the A/PuertoRico/8/34 (H1N1) influenza strain (U.S. Pat. No. 7,037,707). The goal of the reassortment is to increase the yield of candidate vaccine strains achieved by recombining at least the HA or NA genes from the primary clinical isolates, with the six internal genes of the master strain donor virus. This strategy provides high growth reassortants having antigenic determinants similar to those of the clinical isolates (Wood, J. M. and Williams, M. S., Textbook of Influenza. Blackwell Science Ltd, Oxford, 1998; Robertson et al, Biologicals, 20:213, 1992). The vaccines are prepared by growing this reassorted viral strain in embryonated eggs and then inactivating the purified virus by chemical means.

Highly pathogenic avian influenza viruses are capable of causing severe respiratory disease and mortality in birds. This feature is known only for HA of H5 and H7 subtypes. Because of the ability of some avian viruses to transmit to humans, they also become a human health concern. The pathogenicity of avian influenza viruses is a polygenic property but the HA protein has been shown to have the primary role in infection. A prerequisite for virus infectivity is the cleavage of the precursor HA protein (HAO) to HA1 and HA2 subunits. This cleavage releases the peptide that is responsible for the fusion of viral and endosomal membranes. Low pathogenic viruses express surface HA molecules that are activated only by trypsin-like proteases secreted by respiratory or gastrointestinal cells (Perdue et al., Virus Res 49:173-86, 1997). The cleavage site of highly pathogenic viruses is changed in a way that it can be cleaved by different cell proteases, especially by the ubiquitous furin that is present in the majority of cells (Steinhauer D., Virology 258:1-20, 1999; Swayne D., Vet Pathol 34, 557-67, 1997). All highly pathogenic strains invariably contain multiple basic residues (like R and K) at the cleavage site (Perdue et al., supra). Therefore, the virus can rapidly spread and replicate in nearly any organ and induce a systemic infection.

Attenuated H5N1 reassortant viruses have been produced by reverse genetics (R G, Palese et al., Proc. Natl. Acad. Sci. (USA) 93:11354-58, 1996), using the HA and NA genes from an H5N1 strain and inserting these genes into a "backbone" virus comprising the remainder of the internal influenza viral genes from a virus that is less pathogenic. The backbone often used is derived from the prototype strain A/Puerto Rico/8/34 (A/PR/8/34) of subtype H1N1 that is highly adapted to growth in eggs, and only the two surface glycoproteins hemagglutinin (HA) and neuraminidase (NA) are derived from an H5N1 virus. These reassortant viruses are designed for vaccine production in eggs, but the growth of the existing reverse genetic reassortants known in the art is poor in eggs and in cell culture. For example, Suguitan et al. (PLoS Medicine 3:1541-54, 2006) describe use of the cold-adapted Ann Arbor (ca AA) backbone to generate viruses having the HA and NA genes from H5N1 strains, A/Hong Kong/213 and A/Vietnam/1203/2004. These viruses demonstrated attenuation in vivo, i.e, were not lethal in chickens, and also exhibited some protective effects in mice rechallenged with wild type H5N1 virus. Shengqiang et al. (J Infectious Dis 179:1132-8, 1999) also produced recombinant virus using a pandemic Hong Kong strain HA and NA genes and Ann Arbor strain internal genes. Growth of these viruses in eggs, however, is less than optimal.

Likewise, Ming, et al., Chin. J. Biotech. (2006) 22:720-726, described, inter alia, a reassortant virus comprising internal genes from H9N2 viral strains, with a modified HA gene from an H5N1 strain and an NA gene from H2N3. Shi, et al., Vaccine (2007) 25:7379-7384, described, inter alia, a reassortant virus having internal genes from an H9N2 strain, with a modified HA and a wild-type NA gene from an H5N1 strain. Hickman, et al., (J. Gen. Virol. 89:2682-2690, 2008), described, inter alia, a vaccine comprising backbone genes from an H9N2 strain rescued with HA and/or NA genes from H1N1, H5N1 and H7N2 strains.

Recent studies have attempted to generate vaccines that have been grown in mammalian cell culture to avoid the problems commonly observed with growth of virus in egg, e.g., cost of upkeep and maintenance of egg facilities, purification of virus from egg protein, and allergy to residual egg protein. U.S. Pat. Nos. 6,146,873 and 7,132,271, among others, discuss development of cell culture lines that are capable of producing vaccine quality virus. See also Kistner et al., (Vaccine 16:960-8, 1998), which discloses VERO cells adapted for improved viral growth and vaccine production are described, and Ehrlich et al, (New Eng J Med 35:2573-84, 2008), which described, inter alia, a formalin-inactivated H5N1 whole virus vaccine grown in Vero cells.

Thus, there remains a need in the art to produce a pandemic or seasonal influenza vaccine having increased antigenicity compared to previous vaccines, that can elicit a good immune response in a host without causing infection, and which exhibits robust growth in mammalian cell culture.

SUMMARY OF THE INVENTION

The present invention provides for production of an improved vaccine against influenza virus, wherein the vaccine comprises a reassortant virus having a hemagglutinin gene and a neuraminidase gene from the same viral influenza A subtype or influenza B strain and internal genes from a different influenza A subtype or influenza B strain. In one aspect, the HA and NA genes and the internal genes are derived from a highly pathogenic H5N1 strain of influenza A.

In one aspect, the invention provides a reassortant influenza virus comprising: internal gene segments (PB1, PB2, PA, NP, M, and NS) from a first influenza virus A subtype and hemagglutinin (HA) and neuraminidase (NA) genes from the influenza virus subtype from which the internal genes are derived, the internal genes derived from a first strain of an influenza A subtype and the HA and NA genes derived from a second strain in the influenza A subtype. It is further contemplated that the NS gene comprises an NS1, an NS2 or an NS1 and NS2 gene.

In one embodiment, the invention contemplates a purified reassortant influenza virus comprising internal gene segments (PB1, PB2, PA, NP, M, and NS) of an H5N1 strain of influenza A and hemagglutinin (HA) and neuraminidase (NA) genes from an H5N1 influenza A virus, the HA and NA genes derived from the same viral strain. In a related embodiment, the HA and NA genes are from a first H5N1 clade and the internal genes are from a second H5N1 clade. In a further embodiment, the HA and NA genes and the internal genes are derived from the same clade. It is further contemplated that the NS gene comprises an NS1, an NS2 or an NS1 and NS2 gene.

In another embodiment, the invention contemplates a reassortant influenza virus comprising, internal gene segments PB1, PB2, PA, M, NP and NS from a first influenza virus B strain and hemagglutinin (HA) and neuraminidase (NA) genes from a second influenza B strain, wherein the virus is characterized by the ability to propagate in mammalian cell culture.

In a further embodiment, the HA gene of the reassortant virus is modified to produce an attenuated virus. In one embodiment, the HA gene is modified at a polybasic cleavage site. In a still further embodiment, the modification at the polybasic cleavage site in the HA gene is mutation from RERRRKKR (SEQ ID NO: 13)→TETR (SEQ ID NO: 14).

In another embodiment, the virus is characterized by the ability to propagate in mammalian cell culture. In a still further embodiment, the mammalian cells are selected from the group consisting of MRC-5, MRC-9, Lederle 130, Chang liver and WI-38; U937, Vero, CV-1, IMR-90 and IMR-91, MDCK, MDBK, HEK, H9, CEM and CD4-expressing HUT78, PerC6, BHK-21 cells, BSC and LLC-MK2. In a related embodiment, the mammalian cell culture is a Vero cell culture.

In certain embodiments, the influenza A subtype comprises any combination of H1 to H16 and N1 to N9, including H1N1, H2N1, H3N1, H4N1, H5N1, H6N1, H7N1, H8N1, H9N1, H10N1, H11N1, H12N1, H13N1, H14N1, H15N1, H16N1; H1N2, H2N2, H3N2, H4N2, H5N2, H6N2, H7N2, H8N2, H9N2, H10N2, H11N2, H12N2, H13N2, H14N2, H15N2, H16N2; H1N3, H2N3, H3N3, H4N3, H5N3, H6N3, H7N3, H8N3, H9N3, H10N3, H11N3, H12N3, H13N3, H14N3, H15N3, H16N3; H1N4, H2N4, H3N4, H4N4, H5N4, H6N4, H7N4, H8N4, H9N4, H10N4, H11N4, H12N4, H13N4, H14N4, H15N4, H16N4; H1N5, H2N5, H3N5, H4N5, H5N5, H6N5, H7N5, H8N5, H9N5, H10N5, H11N5, H12N5, H13N5, H14N5, H15N5, H16N5; H1N6, H2N6, H3N6, H4N6, H5N6, H6N6, H7N6, H8N6, H9N6, H10N6, H11N6, H12N6, H13N6, H14N6, H15N6, H16N6; H1N7, H2N7, H3N7, H4N7, H5N7, H6N7, H7N7, H8N7, H9N7, H10N7, H11N7, H12N7, H13N7, H14N7, H15N7, H16N7; H1N8, H2N8, H3N8, H4N8, H5N8, H6N8, H7N8, H8N8, H9N8, H10N8, H11N8, H12N8, H13N8, H14N8, H15N8, H16N8; H1N9, H2N9, H3N9, H4N9, H5N9, H6N9, H7N9, H8N9, H9N9, H10N9, H11N9, H12N9, H13N9, H14N9, H15N9, and H16N9. In some embodiments the influenza A subtype is H5N1.

In one embodiment, the internal genes of the reassortant virus are derived from an H5N1 virus known in the art and those described in further detail below in the Detailed Description. In a related embodiment, said internal genes are derived from the H5N1 strain selected from the group consisting of A/Vietnam/1203/2004, A/Hong Kong/213/03, A/Indonesia/5/05, A/Hong Kong/156/97, A/turkey/Turkey/01/2005, A/Anhui/1/05, and A/Cambodia/R0405050/2007, A/chicken/Nakorn-Patom/Thailand/CU-K2/04, A/chicken/Vietnam/C58/04, A/quail/Vietnam/36/04, MDk/JX/1653/05, MDk/1657/JX/05, BH goose/QH/65/05, Gs/GD/1/96-like, Dk/Vietnam/568/05, Gs/GX/345/05, MDk/JX/1701/05, MDk/JX/2136/05, MDk/JX/2295/05, MDk/JX/2300/05, Dk/GX/351/04, Dk/GX/380/04, Dk/ST/4610/03, Ck/MYS/5858/04, Ck/Salatiga/BBVet-I/05, and Dk/VNM/S654/05, A/chicken/Vietnam/C58/05, A/Muscovy Duck/Vietnam/453/2004, A/duck/Singapore/3/97, A/HK/156/97, and A/Hong Kong/156/1996. In a specific embodiment, the internal genes are from A/Vietnam/1203/2004.

In another embodiment, the HA and NA genes of the reassortant virus are derived from an H5N1 virus known in the art and those described in further detail below. In a further embodiment, said HA and NA genes are derived from an H5N1 strain selected from the group consisting of A/Vietnam/1203/2004, A/Hong Kong/213/03, A/Indonesia/5/05, A/Hong Kong/156/97, A/turkey/Turkey/01/2005, A/Anhui/1/05, and A/Cambodia/R0405050/2007, A/chicken/Nakorn-Patom/Thailand/CU-K2/04, A/chicken/Vietnam/C58/04, A/quail/Vietnam/36/04, MDk/JX/1653/05, MDk/1657/JX/05, BH goose/QH/65/05, Gs/GD/1/96-like, Dk/Vietnam/568/05, Gs/GX/345/05, MDk/JX/1701/05, MDk/JX/2136/05, MDk/JX/2295/05, MDk/JX/2300/05, Dk/GX/351/04, Dk/GX/380/04, Dk/ST/4610/03, Ck/MYS/5858/04, Ck/Salatiga/BBVet-I/05, and Dk/VNM/S654/05, A/chicken/Vietnam/C58/05, A/Muscovy Duck/Vietnam/453/2004, A/duck/Singapore/3/97, A/HK/156/97, and A/Hong Kong/156/1996.

In certain embodiments, the internal genes and the HA and NA genes are derived from the same virus strain. In other embodiments, the internal genes and the HA and NA genes are derived from different virus strains.

In an embodiment, the HA and NA genes are from the H5N1 strain A/Vietnam/1203/2004. In another embodiment, the HA and NA genes are from the H5N1 strain A/Indonesia/5/05.

In another aspect, the invention provides an antigenic reassortant influenza virus composition comprising: internal gene segments (PB1, PB2, PA, NP, M, and NS) from a first influenza virus A subtype and hemagglutinin (HA) and neuraminidase (NA) genes from the influenza virus subtype from which the internal genes are derived, the internal genes derived from a first strain of an influenza A subtype and the HA and NA genes derived from a second strain in the influenza A subtype. It is further contemplated that the NS gene comprises an NS1, an NS2 or an NS1 and NS2 gene.

In one embodiment, the antigenic reassortant influenza A virus composition, comprises internal gene segments (PB1, PB2, PA, NP, M, and NS) derived from an H5N1 strain of influenza A and hemagglutinin (HA) and neuraminidase (NA) genes derived from an H5N1 influenza A virus, the HA and NA genes derived from the same viral strain. It is further contemplated that the NS gene comprises an NS1, an NS2 or an NS1 and NS2 gene.

In a further embodiment, the invention provides an antigenic reassortant influenza virus composition comprising, internal gene segments PB1, PB2, PA, M, NP and NS from a first influenza virus B strain and hemagglutinin (HA) and neuraminidase (NA) genes from a second influenza B strain, wherein the virus is characterized by the ability to propagate in mammalian cell culture.

In one embodiment, the HA gene of the compositions is modified to produce an attenuated virus. In a related embodiment, the HA gene is modified at a polybasic cleavage site.

In a further embodiment, the influenza virus is characterized by the ability to propagate in mammalian cell culture.

In one embodiment, the internal genes of the antigenic composition are derived from an H5N1 virus known in the art and those described in further detail below In a related embodiment, said internal genes are derived from the H5N1 strain selected from the group consisting of A/Vietnam/1203/2004, A/Hong Kong/213/03, A/Indonesia/5/05, A/chicken/Nakorn-Patom/Thailand/CU-K2/04, A/chicken/Vietnam/C58/04, A/quail/Vietnam/36/04, MDk/JX/1653/05, MDk/1657/JX/05, BH goose/QH/65/05, Gs/GD/1/96-like, Dk/Vietnam/568/05, Gs/GX/345/05, MDk/JX/1701/05, MDk/JX/2136/05, MDk/JX/2295/05, MDk/JX/2300/05, Dk/GX/351/04, Dk/GX/380/04, Dk/ST/4610/03, Ck/MYS/5858/04, Ck/Salatiga/BBVet-I/05, and Dk/VNM/S654/05, A/chicken/Vietnam/C58/05, A/Muscovy Duck/Vietnam/453/2004, A/duck/Singapore/3/97, A/HK/156/97, and A/Hong Kong/156/1996. In a specific embodiment, the internal genes are from A/Vietnam/1203/2004.

In another embodiment, the HA and NA genes of the antigenic composition are derived from an H5N1 virus known in the art and those described in further detail below.

In a further embodiment, said HA and NA genes are derived from an H5N1 strain selected from the group consisting of A/Vietnam/1203/2004, A/Hong Kong/213/03, A/Indonesia/5/05, A/Hong Kong/156/97, A/turkey/Turkey/01/2005, A/Anhui/1/05, and A/Cambodia/R0405050/2007, A/chicken/Nakorn-Patom/Thailand/CU-K2/04, A/chicken/Vietnam/C58/04, A/quail/Vietnam/36/04, MDk/JX/1653/05, MDk/1657/JX/05, BH goose/QH/65/05, Gs/GD/1/96-like, Dk/Vietnam/568/05, Gs/GX/345/05, MDk/JX/1701/05, MDk/JX/2136/05, MDk/JX/2295/05, MDk/JX/2300/05, Dk/GX/351/04, Dk/GX/380/04, Dk/ST/4610/03, Ck/MYS/5858/04, Ck/Salatiga/BBVet-I/05, and Dk/VNM/S654/05, A/chicken/Vietnam/C58/05, A/Muscovy Duck/Vietnam/453/2004, A/duck/Singapore/3/97, A/HK/156/97, and A/Hong Kong/156/1996.

In certain embodiments, the internal genes and the HA and NA genes of the antigenic composition are derived from the same virus strain. In other embodiments, the internal genes and the HA and NA genes are derived from different virus strains.

In an embodiment, the HA and NA genes of the antigenic composition are from the H5N1 strain A/Vietnam/1203/2004. In another embodiment, the HA and NA genes are from the H5N1 strain A/Indonesia/5/05.

In a still further embodiment, the modification at the polybasic cleavage site in the HA gene is mutation from RERRRKKR (SEQ ID NO: 13)→TETR (SEQ ID NO: 14).

In another embodiment, the antigenic composition further comprises a pharmaceutically acceptable carrier.

In one aspect, the invention contemplates a vaccine comprising a reassortant influenza virus, the virus comprising: i) a polynucleotide encoding for surface protein HA and a polynucleotide encoding for surface protein NA, each of HA and NA derived from an first strain of an influenza virus A subtype; a polynucleotide encoding for PB1; a polynucleotide encoding for PA, a polynucleotide encoding for PB2, a polynucleotide encoding for M, a polynucleotide encoding for NS (NS1 and/or NS2), a polynucleotide encoding for NP, the polynucleotides for PB1, PB2, PA, NP, M, and NS derived from a second strain of an influenza A virus subtype, wherein the polynucleotides are operatively linked to allow packaging of the reassorted polynucleotides into a virion.

In a related embodiment, the invention provides a vaccine comprising a reassortant influenza A virus, the virus comprising: a polynucleotide encoding for surface protein HA and a polynucleotide encoding for surface protein NA, each of HA and NA derived from an H5N1 influenza virus; a polynucleotide encoding for PB1; a polynucleotide encoding for PA, a polynucleotide encoding for PB2, a polynucleotide encoding for M, a polynucleotide encoding for NS1 (NS1 and/or NS2, a polynucleotide encoding for NP, the polynucleotides for PB1, PA, PB2, M, NP, and NS) derived from an H5N1 influenza virus, the polynucleotides being operatively linked to allow packaging of the reassorted polynucleotides into a virion.

In a related embodiment, the invention contemplates a vaccine comprising a reassortant influenza virus, the virus comprising: a polynucleotide encoding for surface protein HA and a polynucleotide encoding for surface protein NA, each of HA and NA derived from an first strain of an influenza B virus; a polynucleotide encoding for PB1; a polynucleotide encoding for PA, a polynucleotide encoding for PB2, a polynucleotide encoding for M, a polynucleotide encoding for NP, a polynucleotide encoding for NS, the polynucleotides for PB1, PA, PB2, M, NP and NS derived from a second strain of an influenza B virus, wherein the polynucleotides are operatively linked to allow packaging of the reassorted polynucleotides into a virion, and wherein the virus is characterized by the ability to propagate in mammalian cell culture.

In one embodiment, the HA gene of the compositions is modified to produce an attenuated virus. In a related embodiment, the HA gene is modified at a polybasic cleavage site.

In one embodiment, the internal genes in the vaccine are derived from an H5N1 virus known in the art and those described in further detail below. In a related embodiment, said internal genes are derived from the H5N1 strain A/Vietnam/1203/2004.

In another embodiment, the HA and NA genes in the vaccine are derived from an H5N1 virus known in the art and those described in further detail below. In a further embodiment, said HA and NA genes are derived from an H5N1 strain selected from the group consisting of A/Vietnam/1203/2004, A/Hong Kong/213/03, A/Indonesia/5/05, A/Hong Kong/156/97, A/turkey/Turkey/01/2005, A/Anhui/1/05, and A/Cambodia/R0405050/2007, A/chicken/Nakorn-Patom/Thailand/CU-K2/04, A/chicken/Vietnam/C58/04, A/quail/Vietnam/36/04, MDk/JX/1653/05, MDk/1657/JX/05, BH goose/QH/65/05, Gs/GD/1/96-like, Dk/Vietnam/568/05, Gs/GX/345/05, MDk/JX/1701/05, MDk/JX/2136/05, MDk/JX/2295/05, MDk/JX/2300/05, Dk/GX/351/04, Dk/GX/380/04, Dk/ST/4610/03, Ck/MYS/5858/04, Ck/Salatiga/BBVet-I/05, and Dk/VNM/S654/05, A/chicken/Vietnam/C58/05, A/Muscovy Duck/Vietnam/453/2004, A/duck/Singapore/3/97, A/HK/156/97, and A/Hong Kong/156/1996.

In certain embodiments, the internal genes and the HA and NA genes in the vaccine are derived from the same virus strain. In other embodiments, the internal genes and the HA and NA genes are derived from different virus strains.

In an embodiment, the HA and NA genes in the vaccine are from the H5N1 strain A/Vietnam/1203/2004. In another embodiment, the HA and NA genes are from the H5N1 strain A/Indonesia/5/05.

In a still further embodiment, the modification at the polybasic cleavage site in the HA gene is mutation from RERRRKKR (SEQ ID NO: 13)→TETR (SEQ ID NO: 14).

In another embodiment, the vaccine further comprises an adjuvant. Exemplary adjuvants include, but are not limited to saponin, non-ionic detergents, vegetable oil, mineral gels such as aluminum hydroxide, surface active substances such as lysolecithin, pluronic polyols, polyanions, peptides, oil or hydrocarbon emulsions, keyhole limpet hemocyanins, oil or potentially useful human adjuvants such as N-acetyl-muramyl-L-threonyl-D-isoglutamine (thr-MDP), N-acetyl-normuramyl-L-alanyl-D-isoglutamine, N-acetylmuramyl-L-alanyl-D-isoglutaminyl-L-alanine-2-(1'-2'-dipalmitoyl-s-n-glycero-3-hydroxyphosphoryloxy)-ethylamine, BCG (bacille Calmette-Guerin) Corynebacterium parvum, ISCOMs, nano-beads, squalene, and block copolymers, which are contemplated for use alone or in combination.

In a further embodiment, the vaccine is an inactivated vaccine. It is contemplated that inactivation is carried out using methods and agents known in the art, including but not limited to, formaldehyde, UV irradiation, glutaraldehyde, binary ethyleneimine (BEI), and beta-propiolactone. It is also contemplated that the vaccine is administered as a live attenuated virus vaccine.

In one embodiment, the vaccine comprises an HA content of from 1 µg to 75 µg HA. In a further embodiment, the vaccine comprises an HA content of 1 µg to 30 µg per vaccine. In related embodiments, the vaccine dose is administered at 1 µg, at 3 µg, at 5 µg, at 7.5 µg, at 10 µg, at 12.5 µg, at 15 µg, at 20 µg, at 25 µg, at 30 µg HA, or in any amount up to 100 µg HA as necessary. Accordingly single vaccine dosages include those having about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, and more than 100 µg hemagglutinin provided in single or multiple dosages at the same or different amount of hemagglutinin.

In another aspect, the invention provides a method for eliciting an immune response to at least one pandemic influenza virus strain in a subject, comprising administering a virus, antigenic composition or a vaccine as described herein in an amount effective to protect the subject against infection of at least one H5N1 influenza virus strain. In a related aspect, the invention contemplates a method for eliciting an immune response to at least one seasonal influenza virus strain in a subject, comprising administering a virus, antigenic composition or a vaccine as described herein in an amount effective to protect the subject against infection of at least one influenza A and/or influenza B virus strain.

In a further aspect, the invention contemplates a method for preventing infection of a subject by an H5N1 influenza virus comprising administering to the subject an effective amount of a virus, antigenic composition or a vaccine as described herein. In another aspect, the invention contemplates a method for preventing infection of a subject by an influenza A or influenza B virus comprising administering to the subject an effective amount of a virus, antigenic composition or a vaccine as described herein.

In one embodiment, the vaccine useful in the methods of the invention comprises an HA content from 1 µg to 75 µg HA. In another embodiment, the vaccine comprises an HA content of 1 µg to 30 µg per vaccine. In related embodiments, the vaccine dose is administered at 1 µg, at 3 µg, at 5 µg, at 7.5 µg, at 10 µg, at 12.5 µg, at 15 µg, at 20 µg, at 25 µg, at 30 µg HA, or in any amount up to 100 µg HA as necessary. Accordingly single vaccine dosages include those having about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, and more than 100 µg hemagglutinin provided in single or multiple dosages at the same or different amount of hemagglutinin.

In another aspect, the invention provides a method of making a vaccine comprising a reassortant influenza virus comprising internal gene segments (PB1, PB2, PA, NP, M, and NS) of an H5N1 strain of influenza A and the hemagglutinin (HA) and neuraminidase (NA) genes from an H5N1 influenza A virus, the HA and NA genes derived from the same viral strain and the HA gene modified at a polybasic cleavage site to produce an attenuated HA gene, the method comprising transfecting the virus in mammalian cells under conditions suitable for growth of the reassortant virus. In a related embodiment, the method of making a vaccine described herein is useful to make a vaccine comprising a seasonal influenza strain of the influenza A or influenza B type.

In one embodiment, the mammalian cells are selected from the group consisting of MRC-5, MRC-9, Lederle 130, Chang liver and WI-38; U937, Vero, CV-1, IMR-90 and IMR-91, MDCK, MDBK, HEK, H9, CEM and CD4-expressing HUT78, PerC6, BHK-21 cells, BSC and LLC-MK2. In a related embodiment, the mammalian cells are Vero cells.

It is further contemplated that, in some embodiments, the virus and compositions described above lack all six internal genes of influenza. In one embodiment, the reassortant virus comprises two, three, four or five internal genes of the influenza virus. For example, in one embodiment, the reassortant virus and/or compositions thereof and/or vaccines lack all or part of the NS1 gene.

In still another aspect, it is contemplated that the invention is carried out using any influenza A and influenza B virus strain. In one embodiment, the reassortant virus may have any combination of eight influenza genes from an influenza A. In a related embodiment, the reassortant virus may have any combination of eight influenza genes from an influenza B virus.

Excluded from the present invention are any viruses (Influenza A and influenza B) previously disclosed or produced, e.g., using backbones such as A/Puerto Rico/8/34 (H1N1), A/Ann Arbor/6/60 (H2N2), A/Leningrad/134/17/57 (H2N2) and B/Ann Arbor/1/66, having internal genes from one strain of a first subtype and the HA and NA genes from a different strain of the same subtype, in any prior publications referenced herein, including but not limited to: U.S. Pat. Nos. 4,552,758; 7,037,707; 7,601,356; 7,566,458; 7,527,800; 7,510,719; 7,504,109; 7,465,456; and 7,459,162; U.S. Patent Publication Nos. 20090297554, 20090246225, 20090208527, 20090175909, 20090175908, 20090175907, 20090136530, 20080069821, 20080057081, 20060252132, 20060153872, 20060110406, 20050158342, 20050042229 and 20070172929; International Patent Publication Nos.; WO 2008/157583, WO 2008/021959, WO 2007/048089, WO 2006/098901, WO 2006/063053, WO 2006/041819, WO 2005/116260, WO 2005/116258, WO 2005/115448, WO 2005/062820, WO 2003/091401 and any viruses identified therein as useful for the FLUMIST™ vaccine, which may contain internal genes from one influenza A subtype strain and HA and NA genes of a different strain of the same subtype in a recombinant virus. All such documents are incorporated by reference herein in their entirety.

In an embodiment, the present invention also excludes naturally-occurring reassortant viruses that comprise a backbone of a first strain of an influenza subtype, and HA and NA genes from a second strain of the same influenza subtype. The term "naturally-occurring reassortant virus" as used herein refers to a reassortant virus that recombines in a natural environment, e.g., viral host, without intervention from an outside source.

In a further embodiment, the invention excludes reassortant viruses having one or more modified internal genes from a first influenza A or B subtype as a backbone, e.g., mutated A/Puerto Rico/8/34 (H1N1), A/Ann Arbor/6/60 (H2N2), or B/Ann Arbor/1/66, and HA and NA genes from the same strain of influenza virus, e.g., as exemplified in U.S. Patent Publication No. 20070172929. The invention contemplates, however, that a virus comprising modified internal genes of the backbone strain of an influenza subtype and HA and NA genes from the same subtype, but different strains, are included within the scope of the invention.

In still another embodiment, the invention excludes reassortant viruses generated using cold adapted viruses as the backbone/donor strain, e.g., A/Ann Arbor/6/60 (H2N2), A/Leningrad/134/17/57 (H2N2), B/Ann Arbor/1/66, and others known in the art, in which the internal backbone genes are from a first subtype and the HA and NA genes are from a different strain of the same subtype.

BRIEF DESCRIPTION OF THE DRAWINGS

FIG. 1 shows the modification of the A/Vietnam/1203/04 (H5N1) HA cleavage site nucleotide sequences and other internal gene sequences using non-coding regions derived from A/Hong Kong/213/03. The sequences derived from A/Hong Kong are underlined.

FIG. 2 shows the modification of the A/Indonesia/5/05 (H5N1) HA cleavage site nucleotide sequences and other internal gene sequences using non-coding regions derived from A/Hong Kong/213/03. The sequences derived from A/Hong Kong are underlined.

FIG. 3 shows the modification of the A/Turkey/Turkey/1/05 (H5N1) HA cleavage site nucleotide sequences and other internal gene sequences using non-coding regions derived from A/Hong Kong/213/03. The sequences derived from A/Hong Kong are underlined.

FIG. 4 shows the modification of the A/Anhui/1/05 (H5N1) HA cleavage site nucleotide sequences and other internal gene sequences using non-coding regions derived from A/Hong Kong/213/03. The sequences derived from A/Hong Kong are underlined.

DETAILED DESCRIPTION

The present invention provides an improved vaccine comprising a reassortant virus having both viral structural proteins, hemagglutinin (HA) and neuraminidase (NA), and viral internal genes [PB1, PB2, PA, NS (NS1, NS2), M1, M2 and NP] derived from various influenza strains. Vaccines of the invention are those wherein the viral internal genes are derived from a specific influenza strain, and the HA and NA genes are derived from the same strain, but the strain from which the internal genes are derived is a influenza A subtype or influenza B strain that is different from the influenza A subtype or influenza B strain from which the HA and NA genes are derived. In one aspect, the HA and NA genes are derived from the same influenza A subtype, and in another aspect, the HA and NA genes are derived from different influenza A subtype. While the invention is exemplified throughout with specific reference to H5N1 vaccines and antigenic compositions, it will be appreciated that any influenza strains constructed as described are embraced by the invention. Vaccines of the invention include those for influenza A and influenza B strains. Influenza A strains include sixteen HA subtypes and nine NA subtypes. The reassortant virus is capable of efficient growth in cell culture, which is an improved method of production over the traditional method of growth in embryonated eggs.

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise The term "reassortant virus" is a virus in which gene segments encoding antigenic proteins (e.g. hemagglutinin and neuraminidase genes) from a virus strain of interest are combined with gene segments encoding viral polymerase complex (PB2, PB1 and PA) genes or other similar genes (e.g., non-glycoprotein genes, including M genes and NS genes, and nucleoprotein (NP) genes) from viruses of a different strain. A "strain" as used herein refers to the particular virus variant of a given species, e.g., influenza A or B species, and subtype in an influenza A virus. For example, the virus A/Vietnam/1203/2004 is an Influenza A virus, subtype H5N1, with the strain name A/Vietnam/1203/2004.

The term "derived from" refers to all or a portion of a polynucleotide or polypeptide sequence that is altered or mutated from a wild-type or naturally-occurring polynucleotide or polypeptide sequence, wherein the polynucleotide or polypeptide derived from the wild type sequence is altered in one or more bases or amino acids such that it no longer has the same sequence as the wild-type sequence.

The term "subtype" as used herein refers to the different viruses within the influenza A strains that can be divided into subtypes based on the HA and NA genes that are expressed in the virus strain. The influenza A subtype nomenclature is based on the HA subtype, e.g., the subtype is any one of the 16 different HA genes known in the art, and the NA subtype, e.g., any of the 9 different NA genes known in the art. Exemplary subtypes, include but are not limited to, H5N1, H1N1, H3N2, and many more known in the art.

The term "clade" as used herein refers to the different categorizations of the influenza A H5N1 viruses that exist. Viruses in an H5N1 clade are genetically related, but do not share the exact viral genome. There are at least seven different clades of H5N1 subtypes designated in the art, e.g., clade 1, clade 2, clade 3, clade 4, clade 5, clade 6 and clade 7. Clade 2 is further divided into subclades.

The term "antigenic composition" refers to a composition comprising material which stimulates the immune system and elicits an immune response in a host or subject. The term "elicit an immune response" refers to the stimulation of immune cells in vivo in response to a stimulus, such as an antigen. The immune response consists of both cellular immune response, e.g., T cell and macrophage stimulation, and humoral immune response, e.g., B cell and complement stimulation and antibody production. The cellular and humoral immune response are not mutually exclusive, and it is contemplated that one or both are stimulated by an antigenic composition, virus or vaccine as described herein. Immune response may be measured using techniques well-known in the art, including, but not limited to, antibody immunoassays, proliferation assays, and others described in greater detail in the Detailed Description.

The term "attenuated" is used to describe a virus or antigenic composition which demonstrates reduced virulence (compared to a wild-type virus). A modified HA is an HA gene that has been altered from the wild-type HA and encodes a protein that is cleaved to a lesser degree than the wild-type HA protein, resulting in reduced growth of the virus. Attenuated virus is typically but not always administered intranasally. Administration of an attenuated virus is contemplated via any route described herein.

The term "inactivated" is used herein to describe a virus that is also known in the art as a "killed" or "dead" virus. An inactivated virus is a whole virus without virulent properties and is produced from a "live" virus, regardless of whether the virus has been previously attenuated in any manner. Inactivated virus is typically, but not always, administered via intramuscular injection. Administration of an inactivated virus in contemplated via any route described herein.

The term "vaccine" as used herein refers to a composition comprising a reassortant virus as described herein, which is useful to establish immunity to the virus in the subject. It is contemplated that the vaccine comprises a pharmaceutically acceptable carrier and/or an adjuvant. It is contemplated that vaccines are prophylactic or therapeutic. A "prophylactic" treatment is a treatment administered to a subject who does not exhibit signs of a disease or exhibits only early signs for the purpose of decreasing the risk of developing pathology. The compounds of the invention may be given as a prophylactic treatment to reduce the likelihood of developing a pathology or to minimize the severity of the pathology, if developed. A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

An "analogue," "analog" or "derivative," which are used interchangeably, refers to a compound, e.g., a peptide or polypeptide, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. It is contemplated that a reassortant virus of the invention comprises an analog of a viral gene, including any one or more than one of an HA, NA, PB1, PB2, PA, M (M1 and M2), NS (NS1 and NS2) and NP gene.

In one aspect, an analog exhibits about 70% sequence similarity but less than 100% sequence similarity with the wild-type or naturally-occurring sequence, e.g., a peptide. Such analogs or derivatives are, in one aspect, comprised of non-naturally occurring amino acid residues, including by way of example and not limitation, homoarginine, ornithine, penicillamine, and norvaline, as well as naturally occurring amino acid residues. Such analogs or derivatives are, in another aspect, composed of one or a plurality of D-amino acid residues, or contain non-peptide interlinkages between two or more amino acid residues. In one embodiment, the analog or derivative may be a fragment of a polypeptide, wherein the fragment is substantially homologous (i.e., at least 70%, at least 75%, at least 80%, at least 85%, at least 90%, or at least 95% homologous) over a length of at least 5, 10, 15, 20, 25, 30, 35, 40, 45 or 50 amino acids of the wild-type polypeptide.

Substitutions are conservative or non-conservative based on the physico-chemical or functional relatedness of the amino acid that is being replaced and the amino acid replacing it. Substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and set out below.

CONSERVATIVE SUBSTITUTIONS

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

CONSERVATIVE SUBSTITUTIONS II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The term "isolated" as used herein refers to a virus or antigenic composition that is removed from its native environment. Thus, an isolated biological material is free of some or all cellular components, i.e., components of the cells in which the native material occurs naturally (e.g., cytoplasmic or membrane component). In one aspect, a virus or antigenic composition is deemed isolated if it is present in a cell extract or supernatant. In the case of nucleic acid molecules, an isolated nucleic acid includes a PCR product, an isolated mRNA, a cDNA, or a restriction fragment.

The term "purified" as used herein refers to a virus or antigenic composition that has been isolated under conditions that reduce or eliminate the presence of unrelated materials, i.e., contaminants, including endogenous materials from which the composition is obtained. By way of example, and without limitation, a purified virion is substantially free of host cell or culture components, including tissue culture or egg proteins and non-specific pathogens. In various embodiments, purified material substantially free of contaminants is at least 50% pure; at least 60%, at least 70%, at least 80%, at least 90%, at least 95%, at least 96%, at least 97%, at least 98% or even at least 99% pure. Purity can be evaluated by chromatography, gel electrophoresis, immunoassay, composition analysis, biological assay, and other methods known in the art.

The term "pharmaceutical composition" refers to a composition suitable for administration to a subject animal, including humans and mammals. A pharmaceutical composition comprises a pharmacologically effective amount of a virus or antigenic composition of the invention and also comprises a pharmaceutically acceptable carrier. A pharmaceutical composition encompasses a composition comprising the active ingredient(s), and the inert ingredient(s) that make up the pharmaceutically acceptable carrier, as well as any product which results, directly or indirectly, from combination, complexation or aggregation of any two or more of the ingredients. Accordingly, the pharmaceutical compositions of the present invention encompass any composition made by admixing a compound or conjugate of the present invention and a pharmaceutically acceptable carrier.

The term "pharmaceutically acceptable carrier" include any and all clinically useful solvents, dispersion media, coatings, antibacterial and antifungal agents, isotonic and absorption delaying agents, buffers, and excipients, such as a phosphate buffered saline solution, 5% aqueous solution of dextrose or mannitol, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Pharmaceutical carriers useful for the composition depend upon the intended mode of administration of the active agent. Typical modes of administration include, but are not limited to, enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound or conjugate for pharmaceutical use including, e.g., metal salts (sodium, potassium, magnesium, calcium, etc.) and salts of ammonia or organic amines.

The term "pharmaceutically acceptable" or "pharmacologically acceptable" refers to a material which is not biologically or otherwise undesirable, i.e., the material may be administered to an individual without causing any undesirable biological effects or interacting in a deleterious manner with any of the components of the composition in which it is contained, or when administered using routes well-known in the art, as described below.

Influenza Genes

Influenza viruses are segmented negative-strand RNA viruses and belong to the Orthomyxoviridae family. Influenza A virus consists of nine structural proteins and codes additionally for one nonstructural NS1 protein with regulatory functions. The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2) (Krug et al., In The Influenza Viruses, R. M. Krug, ed., Plenum Press, N.Y., 1989, pp. 89 152).

Influenza virus ability to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

Hemagglutinin

HA is a viral surface glycoprotein comprising approximately 560 amino acids and representing 25% of the total virus protein. It is responsible for adhesion of the viral particle to, and its penetration into, a host cell in the early stages of infection. There are 16 known HA subtypes, categorized as an H1, H2, H3, H4, H5, H6, H7, H8, H9, H10, H11, H12, H13, H14, H15 or H16 subtype.

Cleavage of the virus HA0 precursor into the HA1 and HA2 subfragments is a necessary step in order for the virus to infect a cell. Thus, cleavage is required in order to convert new virus particles in the host cells into virions capable of infecting new cells. Cleavage is known to occur during transport of the integral HA0 membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HA1 and the carboxy terminal HA2. One of the primary difficulties in growing influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of the HA2 by cleavage is required so that it can be inserted into the target cell, thereby forming a bridge between virus and target cell membrane. This process is followed by fusion of the two membranes and entry of the virus into the target cell.

Proteolytic activation of HA involves cleavage at an arginine residue by a trypsin-like endoprotease, which is often an intracellular enzyme that is calcium dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. On the other hand, HA of pathogenic avian viruses among the H5 and H7 subtypes are cleaved by proteases present in a broad range of different host cells. Thus, there are differences in host range resulting from differences in hemagglutinin cleavability which are correlated with the pathogenic properties of the virus.

The differences in cleavability are due to differences in the amino acid sequence of the cleavage site of the HA. Sequence analyses show that the HA1 and HA2 fragments of the HA molecule of the non-pathogenic avian and all mammalian influenza viruses are linked by a single arginine. In contrast, the pathogenic avian strains have a sequence of several basic amino acids at the cleavage site with the common denominator being lysine-arginine or arginine-arginine, e.g., RRRK (SEQ ID NO: 15). The hemagglutinins of all influenza viruses are cleaved by the same general mechanism resulting in the elimination of the basic amino acids.

Neuraminidase

Neuraminidase is a second membrane glycoprotein of the influenza A viruses. The presence of viral NA has been shown to be important for generating a multi-faceted protective immune response against an infecting virus. NA is a 413 amino acid protein encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates release of viral progeny by preventing newly formed viral particles from accumulating along the cell membrane, as well as by promoting transportation of the virus through the mucus present on the mucosal surface. NA is an important antigenic determinant that is subject to antigenic variation.

Administration of chemical inhibitors of neuraminidase limits the severity and spread of viral infections. Neuraminidase inhibitors combat influenza infection by preventing the virus from budding from the host cell. Exemplary NA inhibitors include, but are not limited to, zanamivir, administered by inhalation; oseltamivir, administered orally; and peramivir administered parenterally.

Internal Genes of Influenza

In addition to the surface proteins HA and NA, influenza virus comprises six additional internal genes, which give rise to eight different proteins, including polymerase genes PB1, PB2 and PA, matrix proteins M1 and M2, nucleoprotein (NP), and non-structural proteins NS1 and NS2 (Horimoto et al., Clin Microbiol Rev. 14(1):129-49, 2001).

In order to be packaged into progeny virions, viral RNA is transported from the nucleus as a ribonucleoprotein complex composed of the three influenza virus polymerase proteins, the nucleoprotein (NP), and the viral RNA, in association with the influenza virus matrix 1 (M1) protein and nuclear export protein (Marsh et al., J Virol, 82:2295-2304, 2008). The M1 protein that lies within the envelope is thought to function in assembly and budding.

A limited number of M2 proteins are integrated into the virions (Zebedee, J. Virol. 62:2762-2772, 1988). They form tetramers having H+ ion channel activity, and, when activated by the low pH in endosomes, acidify the inside of the virion, facilitating its uncoating (Pinto et al., Cell 69:517-528, 1992). Amantadine is an anti-influenza drug that prevents viral infection by interfering with M2 ion channel activity, thus inhibiting virus uncoating.

NS1 protein, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable although it grew less efficiently than the parent virus in interferon-nondefective cells (Garcia-Sastre, Virology 252:324-330, 1998).

NS2 protein has been detected in virus particles. The average number of NS2 proteins in a virus particle was estimated to be 130-200 molecules. An in vitro binding assay shows direct protein-protein contact between M1 and NS2. NS2-M1 complexes were also detected by immunoprecipitation in virus-infected cell lysates (Virology. 196:249-55, 1993). The NS2 protein, known to exist in virions (Richardson et al., Arch. Virol. 116:69-80, 1991; Yasuda et al., Virology 196:249-255, 1993), is thought to play a role in the export of RNP from the nucleus through interaction with M1 protein (Ward et al., Arch. Virol. 140:2067-2073, 1995).

Reverse Genetics and Reassortant Viruses

Techniques to isolate and modify specific nucleic acids and proteins are well known to those of skill in the art. In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning. A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis employing oligonucleotides with altered nucleotides for generating PCR products with mutations.

In one aspect, the present invention is based upon the generation of avian influenza viruses and vaccines thereof by reverse genetics methodologies as described herein and known in the art.

The mechanism of influenza viral RNA transcription is unique (Horimoto et al., Clin Microbiol Rev. 14(1):129-49, 2001). The 5' cap from cellular mRNAs is cleaved by a viral endonuclease and used as a primer for transcription by the viral transcriptase (Krug et al., Cell 18:329-334, 1979). Six of eight RNA segments are transcribed into mRNAs in a monocistronic manner and translated into HA, NA, NP, PB1, PB2, and PA. By contrast, two RNA segments are each transcribed to two mRNAs by splicing. For both the M and NS genes, coding mRNAs are translated in different reading frames, generating M1 and M2 proteins and NS1 and NS2 proteins, respectively. It is believed that the increased concentration of free NP triggers the shift from mRNA synthesis to complementary RNA (cRNA) and viral RNA (vRNA) synthesis (Shapiro et al., J. Virol. 62:2285-2290, 1988). Newly synthesized vRNAs are encapsidated with NP in the nucleus, where they function as templates for secondary transcription of viral mRNAs.

Recently developed reverse-genetics systems have allowed the manipulation of the influenza viral genome (Palese et al., Proc. Natl. Acad. Sci. USA 93:11354-58, 1996; Neumann and Kawaoka, Adv. Virus Res. 53:265, 1999; Neumann et al., Proc. Natl. Acad. Sci. USA 96:9345, 1999; Fodor et al., J. Virol. 73: 9679, 1999). Reverse genetics in the influenza virus context is a mechanism by which negative sense RNA is engineered into cDNA for recombinant preparation of organisms having negative strand RNA genomes. The reverse genetics technique involves the preparation of synthetic recombinant viral RNAs that contain the non-coding regions of the negative strand virus essential for the recognition of viral RNA by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. See U.S. Pat. Nos. 6,022,726 and 6,001,634.

These recombinant methods allow for the production of influenza virus types with specific alterations to the polypeptide amino acid sequence. For example, an HA molecule containing a desired substitution may be part of a recombinant influenza virus. In one method, the recombinant influenza virus is made through a genetic engineering method such as the "plasmid only" system (Hoffmann et al., Vaccine 20:3165, 2002).

In another method for generating a recombinant virus, an eight plasmid system is used, wherein the negative sense RNAs are expressed from a pol I promoter and the coexpression of the polymerase complex proteins result in the formation of infectious influenza A virus (Hoffmann et al., Proc. Natl. Acad. Sci. USA 97:6108-13, 2000). This technology allows the rapid production of chimeric vaccines from cDNA for use in the event of an influenza pandemic, and provides the capability to attenuate pathogenic strains (Subbarao et al., Virology 305:192-200, 2003), while eliminating the need to screen reassortant viruses for the 6:2 configuration (i.e., 6 internal genes and 2 HA and NA genes (one of each gene)). See also U.S. Pat. No. 7,037,707.

In one embodiment, in the case of highly pathogenic influenza viruses such as H5N1, the polybasic cleavage site of the HA which is responsible for the highly pathogenic nature of the virus is removed by site-directed mutagenesis to attenuate the virus and to change its classification from BSL-3 to BSL-2. In addition, one or more of the internal genes of the prototype donor strain are replaced by the genes of viruses of other subtypes to further improve the growth characteristics.

Such a virus which combines high growth characteristics with the immunological advantages of an H5N1 wildtype virus saves time for production and, in one aspect, is a 6:2 reassortant having the 6 internal genes from an H5N1 virus such as Vietnam or Indonesia as a backbone and the HA (with the mutated cleavage site for attenuation) and the NA of the actual H5N1 pandemic(-like) strain. Another example of a reassortant virus which has a high growth potential is a 5:1:2 reassortant with 5 internal genes from the H5N1 viruses such as Vietnam or Indonesia, the PB2 of an H1N1 strain (for improved growth in cell culture) as a backbone and the HA (with a mutated cleavage site for attenuation) and NA of the actual H5N1 pandemic strain.

In some embodiments, the reassortant viruses are prepared using the method of Palese et al. (Proc. Natl. Acad. Sci. USA 93:11354-58, 1996), which describes use of a helper virus system to generate genetically engineered virus. In one embodiment, the virus is generated using an influenza helpervirus method. For example to construct a 6:2 reassortant, the attenuated VN1203 virus could be used as a helper virus to introduce the HA and NA from a second H5N1 strain, such as the chicken Egypt strain (Aly et al., Avian Dis. 52:269-77, 2008). Selection of the transfectant virus is carried out using neutralizing antibodies against the helper HA or NA proteins (sew e.g., FIG. 2 of Palese et al., supra).

Two exemplary attenuated H5N1 reassortants described herein have the backbone of the H5N1 clade 1 strain A/Vietnam/1203/2004, i.e., the six internal genes (PB1, PB2, PA, NP, M, NS); one contains the mutated HA and NA of the H5N1 clade 1 Vietnam 1203 strain and the mutated HA and the NA of an H5N1 virus of a different clade, e.g., the clade 2 strain A/Indonesia/5/05. These two attenuated RG reassortants have a high-growth potential in standard Vero cells (containing fetal bovine serum) or serum protein free Vero cells. These reassortant viruses also have the potential to induce an enhanced H5N1 specific immune response in comparison to the existing RG H5N1/PR8 reassortants as they contain all H5N1 proteins, namely the nucleoprotein and the matrix protein which are mainly responsible for the induction of cellular immunity. These H5N1-specific cellular immune responses may also have the ability to induce a broader immune response by specific induction of T helper cells, cytotoxic T lymphocytes (CTLs) and memory cells resulting in an improved booster effect. This result is not the case with existing H5N1/PR8 reassortants having the internal proteins derived from the egg-adapted seasonal strain of subtype H1N1, which do not induce a strong H5N1-specific cellular immune response.

Numerous H5N1 strains have been identified in the art, each of which is amenable to the invention. See e.g, Govorkova et al., J Virol. 2005 February; 79(4):2191-8; Proc Natl Acad Sci USA 103:2845-50, 2006; Horimoto et al., Clin Microbiol Rev 14:129-49, 2001, and Cauthen et al., J Virol. 74:6592-9, 2000, among others (see, e.g., Lee et al., J Virol 79:3692-02, 2005).

Examples of avian H5N1 influenza strains that are useful in the present invention include, but are not limited to, A/Vietnam/1203/2004 (H5N1) (CDC#2004706280) (VN1203), A/Indonesia/05/2005 (H5N1) (CDC #2005740199) (IN5/05), A/Cambodia/R0405050/2007 (H5N1) (CamR04), A/Anhui/1/05 (H5N1) (AH1/05) A/turkey/Turkey/01/2005 (H5N1) (TT01) (see e.g., Carter et al., BioDrugs. 22:279-92, 2008), A/Vietnam/1194/2004, turkey influenza virus strain A/Turkey/England/50-92/91 (H5N1) (see, e.g., Horimoto et al., Clin Microbiol Rev 14:129-49, 2001), A/turkey/England/87-92BFC/91 (H5N1) (Londt et al., Avian Pathology, 36:347-350, 2007), chicken influenza virus strain A/Chicken/Indonesia/03 (H5N1), chicken influenza virus strain A/Chicken/Hong Kong/220/97 (see, e.g., Tumpey et al., J Virol 76:6344-55, 2002), chicken influenza virus strain A/Chicken/Scotland/59 (H5N1) (see, e.g., Horimoto et al., supra), chicken influenza virus strain A/Chicken/Hong Kong/258/97 (H5N1) (see, e.g., Horimoto et al., supra), chicken influenza virus strain A/Chicken/Nakom-Patom/Thailand/CU-K2/2004 (H5N1) (see, e.g., Anwar et al., In Silico Biol. 6:161-8, 2006; Viseshakul et al., Virology. 328:169-76, 2004), chicken influenza virus strain A/Chicken/Hong Kong/31.2/2002 (H5N1), (see, e.g., Anwar et al., supra), chicken influenza virus strain A/Chicken/Vietnam/C58/04 (H5N1), (see, e.g., Anwar et al., supra), chicken influenza virus strain A/Chicken/Vietnam/38/2004 (H5N1). (see, e.g., Anwar et al., supra), chicken influenza virus strain A/Chicken/Hong Kong/1000/97 (H5N1) (see, e.g., Shan et al., Biochem Biophys Res Commun. 302:377-83, 2003), chicken influenza virus strain A/Chicken/Hong Kong/317.5/01 and duck influenza virus strain A/Duck/Anyang/AVL-1/01 (see, e.g., Tumpey et al., J Virol 76:6344-55, 2002), duck influenza virus strain A/Duck/Vietnam/11/2004 (H5N1), A/Hatay/2004/(H5N1) (see, e.g., Anwar et al., supra), duck influenza virus strains A/Duck/Korea/ES/03 (H5N1), A/Duck/Korea/ESD1/03 (H5N1) and A/Duck/Hong Kong/821/02 (H5N1) (see e.g., Lee et al., J Virol 79:3692-02, 2005), duck influenza virus strain A/Duck/Vietnam/11/2004 (H5N1), A/Duck/China/E319-2/03 (see Lee et al., Vet Microbiol 124:193-201, 2007), egret influenza virus A/egret/Hong Kong/757.2/02 (H5N1) (see e.g., Lee et al., J Virol 79:3692-02, 2005), goose influenza virus strain A/Goose/Guangdong/1/96 (see, e.g., Cauthen et al., J Virol. 74:6592-9, 2000), avian influenza virus strain A/Env/HK/437-4/99 (see, e.g., Cauthen et al., supra), avian influenza virus strain A/Env/HK/437-6/99 (see, e.g., Cauthen et al., supra), avian influenza virus strain A/Env/HK/437-8/99 (see, e.g., Cauthen et al., supra), avian influenza virus strain A/Env/HK/437-10/99, (see, e.g., Cauthen et al., supra), avian influenza virus strain A/Quail/Vietnam/36/04 (H5N1). (see, e.g., Anwar et al., supra), avian influenza virus strain A/Swan/Italy/179/06 (H5N1) (see, e.g., Terregino et al., Vet Rec. 158:491, 2006), avian influenza virus strain A/Hong Kong/156/97 (H5N1) (HK156) (see, e.g., Cauthen et al., supra), and avian influenza virus strain A/Hong Kong/213/03 (H5N1) (HK213) (see, e.g., Shinya et al., J. Virol. 79:9926-32, 2005) as well as those disclosed in Lee et al., Emerging Infect Dis. 14:487-90, 2008.

With knowledge of internal genes and HA and NA genes from H5N1 strains, it will be appreciated that, in an alternative embodiment, polynucleotides encoding these genes are synthesized by techniques well know and routinely practiced in the art.

In another embodiment, influenza virus of other influenza A subtypes and influenza B viruses are useful in the methods and compositions of the invention. For example, influenza A virus having any HA subtype is contemplated, including any of the H1 to H16 subtypes In a still further embodiment it is contemplated that an influenza virus having any of NA subtypes N1 to N9 is useful for the invention.

In certain embodiments, it is contemplated that when generating a reassortant, the HA and NA subtype are derived from the same strain, and the backbone is derived from an influenza virus of the same subtype. Exemplary combinations include, but are not limited to, e.g., an H3N2 backbone having H3 and N2 genes from different H3N2 virus strain, or an H15N8 backbone having H15 and N8 genes from different H15N8 virus strain. It is further contemplated that any of the following influenza A subtypes are useful in the invention: H1N1, H2N1, H3N1, H4N1, H5N1, H6N1, H7N1, H8N1, H9N1, H10N1, H11N1, H12N1, H13N1, H14N1, H15N1, H16N1; H1N2, H2N2, H3N2, H4N2, H5N2, H6N2, H7N2, H8N2, H9N2, H10N2, H11N2, H12N2, H13N2, H14N2, H15N2, H16N2; H1N3, H2N3, H3N3, H4N3, H5N3, H6N3, H7N3, H8N3, H9N3, H10N3, H11N3, H12N3, H13N3, H14N3, H15N3, H16N3; H1N4, H2N4, H3N4, H4N4, H5N4, H6N4, H7N4, H8N4, H9N4, H10N4, H11N4, H12N4, H13N4, H14N4, H15N4, H16N4; H1N5, H2N5, H3N5, H4N5, H5N5, H6N5, H7N5, H8N5, H9N5, H10N5, H11N5, H12N5, H13N5, H14N5, H15N5, H16N5; H1N6, H2N6, H3N6, H4N6, H5N6, H6N6, H7N6, H8N6, H9N6, H10N6, H11N6, H12N6, H13N6, H14N6, H15N6, H16N6; H1N7, H2N7, H3N7, H4N7, H5N7, H6N7, H7N7, H8N7, H9N7, H10N7, H11N7, H12N7, H13N7, H14N7, H15N7, H16N7; H1N8, H2N8, H3N8, H4N8, H5N8, H6N8, H7N8, H8N8, H9N8, H10N8, H11N8, H12N8, H13N8, H14N8, H15N8, H16N8; H1N9, H2N9, H3N9, H4N9, H5N9, H6N9, H7N9, H8N9, H9N9, H10N9, H11N9, H12N9, H13N9, H14N9, H15N9, and H16N9. Influenza A viruses of the following subtypes have been identified previously, H1N1, H2N2, H1N2, H3N2, H3N8, H4N6, H5N1, H5N2, H5N3, H5N9, H6N1, H6N2, H6N5, H7N1, H7N7, H8N4, H9N2, H10N7, H11N6, H12N5, H13N6, H14N5, H15N8, H15N9, H16N3. Table 1 lists exemplary HA and NA genes from influenza A strains useful for generating a reassortant virus.

TABLE 1

| Gene Subtype | Accession No. | |
|---|---|---|
| | | Hemagglutinin Genes |
| H1 | NC_002017 | Influenza A virus (A/Puerto Rico/8/34(H1N1)) segment 4, complete sequence |
| H1 | FJ966952 | Influenza A virus (A/California/05/2009(H1N1)) segment 4 hemagglutinin (HA) gene, complete cds. |
| H2 | L20410 | Influenza A virus (A/Singapore/1/1957(H2N2)) hemagglutinin (HA)gene, complete cds. |
| H2 | L11126 | Influenza A virus (A/Berlin/3/64 (H2N2)) hemagglutinin (HA) gene, complete cds. |
| H3 | CY050836 | Influenza A virus (A/New York/3487/2009(H3N2)) segment 4, complete sequence. |
| H3 | CY008628 | Influenza A virus (A/Canterbury/257/2005(H3N2)) segment 4, complete sequence. |
| H4 | M25290 | Influenza A virus (A/turkey/Minnesota/833/1980(H4N2)) hemagglutinin (HA) gene, complete cds. |
| H4 | FJ428583 | Influenza A virus (A/mallard/Poyang Lake/15/2007(H4N6)) segment 4 hemagglutinin (HA) gene, complete cds. |
| H5 | EF541403 | Influenza A virus (A/Viet Nam/1203/2004(H5N1)) segment 4 hemagglutinin (HA) gene, complete cds. |
| H5 | AF082035 | Influenza A virus (A/Chicken/Hong Kong/786/97 (H5N1)) hemagglutinin H5 mRNA, complete cds. |
| H6 | GQ117282 | Influenza A virus (A/ring-billed gull/GA/421733/2001 (H6N4)) segment 4 hemagglutinin (HA) gene, complete cds. |
| H6 | CY045343 | Influenza A virus (A/northern shoveler/California/K138/2005(H6N2)) segment 4, complete sequence. |
| H7 | EF576989 | Influenza A virus (A/duck/AB/AFLBs8734c16/2007(H7)) segment 4, complete sequence. |
| H7 | AY240925 | Influenza A virus (A/avian/NY/73063-6/00(H7N2)) hemagglutinin (HA) gene, complete cds. |
| H8 | CY043848 | Influenza A virus (A/mallard/Netherlands/1/2006(H8N4)) segment 4, complete sequence. |
| H8 | AB450435 | Influenza A virus (A/duck/Alaska/702/1991(H8N7)) HA gene for haemagglutinin, complete cds. |
| H9 | GU071984 | Influenza A virus (A/chicken/Iran/THLBM868/2007(H9N2)) segment 4 hemagglutinin (HA) gene, complete cds. |
| H9 | CY023992 | Influenza A virus (A/duck/Shantou/3577/2003(H9N2)) segment 4 sequence. |
| H10 | EU124207 | Influenza A virus (A/Duck/Indonesia/Jakarta Utara1631-29/2006(H10)) segment 4 hemagglutinin (HA) gene, complete cds. |
| H10 | M21647 | Influenza A virus (A/chicken/Germany/N/1949(H10N7)) hemagglutinin precursor, gene, complete cds. |
| H11 | CY021437 | Influenza A virus (A/environment/Delaware/235/2005(H11N6)) segment 4, complete sequence. |
| H11 | D90306 | Influenza A virus (A/duck/England/1/1956(H11N6)) gene for hemagglutinin precursor, complete cds. |
| H12 | CY021877 | Influenza A virus (A/mallard/Maryland/1131/2005(H12N5)) segment 4, complete sequence. |
| H12 | AB288334 | Influenza A virus (A/duck/Alberta/60/1976(H12N5)) HA gene for haemagglutinin, complete cds. |
| H13 | EU835900 | Influenza A virus (A/gull/Astrakhan/1818/1998(H13N6)) hemagglutinin (HA) gene, complete cds. |
| H13 | AB292664 | Influenza A virus (A/gull/Maryland/704/1977(H13N6)) HA gene for haemagglutinin, complete cds. |
| H14 | FJ975075 | Influenza A virus (A/herring gull/Astrakhan/267/1982(H14N5)) segment 4 hemagglutinin (HA) gene, complete cds. |
| H14 | AM922165 | Influenza A virus (A/mallard/Gur/263/82(H14N3)) partial HA gene for hemagglutinin, genomic RNA. |
| H15 | L43917 | Influenza A virus (A/shearwater/West Australia/2576/79(H15N9)) hemagglutinin mRNA, complete cds. |
| H15 | CY006032 | Influenza A virus (A/Australian shelduck/Western Australia/1756/1983(H15N2)) segment 4, complete sequence. |
| H16 | EU148600 | Influenza A virus (A/mallard/Gurjev/785/83(H16N3)) hemagglutinin precursor (HA) gene, complete cds. |
| H16 | EU564109 | Influenza A virus (A/Fulica atra/Volga/635/1986(H16N3)) segment 4 hemagglutinin (HA) gene, complete cds. |
| | | Neuraminidase Genes |
| N1 | FJ969517 | Influenza A virus (A/California/04/2009(H1N1)) segment 6 neuraminidase (NA) gene, complete cds. |
| N1 | CY030233 | Influenza A virus (A/Brisbane/59/2007(H1N1)) segment 6 sequence. |
| N2 | EU199420 | Influenza A virus (A/Brisbane/10/2007(H3N2)) segment 6 neuraminidase (NA) gene, complete cds. |
| N2 | GU052277 | Influenza A virus (A/turkey/England/1969(H3N2)) segment 6 neuraminidase (NA) gene, complete cds. |
| N3 | GU052285 | Influenza A virus (A/seal/Massachusetts/3911/1992(H3N3)) segment 6 neuraminidase (NA) gene, complete cds. |
| N3 | GU052831 | Influenza A virus (A/environment/California/508249/2007(H5N3)) segment 6 neuraminidase (NA) gene, complete cds. |
| N4 | CY039550 | Influenza A virus (A/northern shoveler/California/AKS273/2007(H8N4)) segment 6 sequence. |
| N4 | EU557563 | Influenza A virus (A/northern pintail/Alaska/44204-158/2006(H6N4)) segment 6 neuraminidase (NA) gene, complete cds. |
| N5 | EU871915 | Influenza A virus (A/mallard/MN/105/2000(H5N5)) segment 6 neuraminidase (NA) gene, complete cds. |
| N5 | CY033334 | Influenza A virus (A/northern shoveler/California/HKWF1046/2007(H3N5)) segment 6 sequence. |
| N6 | GU051165 | Influenza A virus (A/ruddy turnstone/New Jersey/950/2005(H3N6)) segment 6 neuraminidase (NA) gene, complete cds. |
| N6 | GU053454 | Influenza A virus (A/mallard/Ohio/684/2002(H4N6)) segment 6 neuraminidase (NA) gene, complete cds. |
| N7 | FJ517261 | Influenza A virus (A/shorebird/DE/1346/2001(H5N7)) segment 6 neuraminidase (NA) gene, complete cds. |
| N7 | GU051509 | Influenza A virus (A/mallard/Minnesota/17/1999(H7N7)) segment 6 neuraminidase (NA) gene, complete cds. |
| N8 | CY015091 | Influenza A virus (A/turkey/Ireland/1378/1983(H5N8)) segment 6, complete sequence. |
| N8 | CY043810 | Influenza A virus (A/ring-necked duck/California/K90/2005(H6N8)) segment 6, complete sequence. |
| N9 | AB292782 | Influenza A virus (A/duck/Hong Kong/562/1979(H10N9)) NA gene for neuraminidase, complete cds. |
| N9 | GU053360 | Influenza A virus (A/blue-winged teal/Ohio/467/2001(H11N9)) segment 6 neuraminidase (NA) gene, complete cds. |

Additional influenza A and B viruses contemplated include, but are not limited to, A/Brisbane/59/2007 (H1N1); A/Brisbane/10/2007 (H3N2); A/Solomon Islands/3/2006 (H1N1); A/Uruguay/716/2007; A/Wisconsin/67/2005 (H3N2); A/New Calcdonia/20/99 (H1N1); A/California/7/2004 (H3N2); A/New York/55/2004; A/Wellington/1/2004 (H3N2); A/Fujian/411/2002 (H3N2); A/Moscow/10/99 (H3N2); A/Panama/2007/99; A/Sydney/5/97 (H3N2); A/Beijing/262/95 (H1N1); B/Florida/4/2006; B/Malaysia/2506/2004; B/Shanghai/361/2002; B/Sichuan/379/99; B/Hong Kong/330/2001; B/Guangdong/120/2000; B/Johannesburg/5/99; B/Victoria/504/2000; B/Sichuan/379/99; B/Beijing/184/93; B/Yamanashi/166/98; B/Shangdong/7/97; B/Harbin/7/94, B/Hawaii/10/2001 and viruses having like properties to any of the above viruses. U.S. Patent Publication No. 20090010962, incorporated herein by reference, describes influenza A H1N1 viruses useful in the invention.

A list of identified Influenza A strains, including influenza A H5N1 strains is available from the World Health Organization (WHO) and United States Centers for Disease Control (CDC) databases of Influenza A and H5N1 subtypes. The National Center for Biotechnology Information (NCBI) database maintained by the United States National Library of Medicine also maintains an updated database describing the length and sequence of HA and NA genes of identified viruses of influenza A and influenza B species. Strains listed by these organizations and viral strains described in other commercial and academic databases, or in literature publications and known in the art, are contemplated for use in the invention. It is also contemplated that additional influenza A and influenza B strains hereafter identified and isolated are also useful in the invention. Accordingly, any H5N1 strain specifically exemplified in the specification and those known or after discovered in the art are amenable to the reassortant virus, antigenic composition, vaccine and methods of the invention.

Emphasizing the novelty of the invention and differentiation of the invention from reassortant viruses previously disclosed in the art, specifically excluded from the present invention are any viruses (Influenza A and influenza B) previously disclosed or produced, e.g., using backbones such as A/Puerto Rico/8/34 (H1N1), A/Ann Arbor/6/60 (H2N2) and B/Ann Arbor/1/66, having internal genes from one strain and the HA and NA genes from a different strain of the same subtype, in any prior publications referenced herein, including but not limited to: U.S. Pat. Nos. 4,552,758, 7,037,707, 7,601,356 7,566,458 7,527,800 7,510,719 7,504,109, 7,465,456, 7,459,162; U.S. Patent Publication Nos. 20090297554, 20090246225, 20090208527, 20090175909, 20090175908, 20090175907, 20090136530, 20080069821, 20080057081, 20060252132, 20060153872, 20060110406, 20050158342, 20050042229 and 20070172929; International Patent Publication Nos.; WO 2008/157583, WO 2008/021959, WO 2007/048089, WO 2006/098901, WO 2006/063053, WO 2006/041819, WO 2005/116260, WO 2005/116258, WO 2005/115448, WO 2005/062820, WO 2003/091401 and any viruses identified therein as useful for the FLUMIST™ vaccine, which may contain internal genes from one influenza A subtype and HA and NA genes of the same subtype in a recombinant virus. All such documents are incorporated by reference herein in their entirety.

In an embodiment, the present invention also excludes naturally-occurring reasortant viruses that comprise a backbone of a first strain of an influenza subtype, and HA and NA genes from a second strain of the same influenza subtype. The term "naturally-occurring reassortant virus" as used herein refers to a reassortant virus that recombines in a natural environment without intervention from an outside source.

In a further embodiment, the invention excludes reassortant viruses having one or more modified internal genes from a first influenza A or B subtype as a backbone, e.g., mutant A/Puerto Rico/8/34 (H1N1), A/Ann Arbor/6/60 (H2N2), or B/Ann Arbor/1/66, and HA and NA genes from the same strain of influenza virus, e.g., as exemplified in U.S. Patent Publication No. 20070172929. The invention contemplates, however, that a virus comprising modified internal genes of the backbone strain of an influenza subtype and HA and NA genes from the same subtype, but different strains, are included within the scope of the invention.

In still another embodiment, the invention excludes reassortant viruses generated using cold adapted viruses as the backbone/donor strain, e.g., A/Ann Arbor/6/60 (H2N2), A/Leningrad/134/17/57 (H2N2), B/Ann Arbor/1/66, and others known in the art, in which the internal backbone genes are from a first subtype and the HA and NA genes are from a different strain of the same subtype.

Cells Lines

Typical influenza viruses are adapted for growth in chicken eggs but the expense for maintaining the egg cultures is significantly greater than growing virus in cell culture. Conventional chicken embryo cell (CEC) cultures have been used in attempts to grow influenza virus for vaccine, but these provide only some of the protease activities of a whole chicken embryo and, hence, allow replication of a limited range of influenza virus strains. Standard procedures for preparation of CEC cultures involve removal of the head and inner organs and multiple trypsinization steps. These procedures result specifically in the loss of brain, heart, lung, liver and kidney cells, which have been shown to replicate a number of influenza strains (Scholtissek et al., J. Gen. Virol., 69:2155-2164, 1988). Standard procedures thus result in a highly selected cell population consisting mainly of fibroblasts, which are limited in terms of the virus strains that they can support.

Improvements in influenza virus production have been attempted in both chicken cultures and in mammalian cell lines. For instance, it has been reported that the limited replication of several influenza A strains in standard cell cultures could be ameliorated by the addition of trypsin to the tissue culture medium. For example, trypsin addition significantly increases the infectivity of various strains grown in CEC cultures (Lazarowitz et al., Virology, 68:440-454, 1975). In addition, Stieneke-Grober et al., (EMBO J., 11: 2407-2414, 1992), have identified the HA activating enzyme in MDBK cells as a furin-like protease. Such enzymes have been isolated from human and mouse tissues and constitute a new family of eukaryotic subtilisin-like endoproteases. Katz et al., (J. Infect. Dis. 160:191-98, 1989) compared the growth characteristics of influenza H3N2 in MDCK cells and amniotic cavity of embryonated eggs and showed that the influenza titer obtained from MDCK cells was comparable to embryonated eggs and the MDCK grown virus produced increased antigenicity in vivo. There are problems with using MDCK cells, however. For example, MDCK cells are not licensed cell line for production of human vaccines and the procedure requires viruses to be multiply and serially passaged in the MDCK cell line.

Vero cells adapted for improved viral growth and vaccine production are described in U.S. Pat. No. 6,146,873 and Kistner et al., (Vaccine. 16:960-8, 1998), incorporated herein by reference. Vero cells are an accepted cell line for production of vaccine according to the World Health Organization. In one embodiment, viruses of the present invention are grown in Vero cells as described in the Examples below.

Additional mammalian cell lines are useful for culture and growth of virus. Exemplary mammalian cells useful to culture virus for the preparation of vaccine include, but are not limited to: MRC-5, MRC-9, Lederle 130, Chang liver and WI-38 (human fibroblast); U937 (human monocyte); Vero and CV-1 (African Green monkey): IMR-90 and IMR-91 (human lung fibroblast having characteristics of smooth muscle), MDCK (Madin Darby canine kidney), MDBK (Madin Darby bovine kidney), HEK (human embryonic kidney), H9, CEM and CD4-expressing HUT78 (human T cell): PerC6 (human retinoblast); BHK-21 cells (baby hamster kidney), BSC (monkey kidney cell) and LLC-MK2 (monkey kidney).

Vaccines

It is contemplated that a desired virus strain obtained from tissue-culture preparation is used to produce a vaccine. Many types of viral vaccines are known, including but not limited to, attenuated, inactivated, subunit, and split vaccines.

Attenuated vaccines are live viral vaccines that have been altered in some manner to reduce pathogenicity and no longer cause disease. Attenuated viruses are produced in several ways, including growth in tissue culture for repeated generations and genetic manipulation to mutate or remove genes involved in pathogenicity. For example, in one embodiment, viral genes and/or proteins identified as involved in pathogenicity or involved in the disease manifestation, are mutated or changed such that the virus is still able to infect and replicate within a cell, but it cannot cause disease. An example of this is to mutagenize the HA1/HA2 cleavage site. Attenuation of virus has also been successful by insertion of a foreign epitope into a viral gene segment, for example the NA gene (J Virol. 66: 4647-4653, 1992), thereby interfering with the normal function of the genome. Virus are also attenuated using cold adaptation methods well-known in the art. See, for example, Maassab et al., Rev Med Virol. 9:237-44, 1999, which discusses methods to attenuate type A and Type B influenza virus, and Ghendon et al., (Vaccine. 23:4678-84, 2005), which describe a cold adapted influenza virus that grows in MDCK cells.

Additional methods to attenuate a virus include construction of a reassortant virus lacking the NS1 gene. See for example U.S. Pat. Nos. 6,468,544, 6,573,079, 6,669,943, and 6,866,853 and U.S. Patent Publication Nos. 20030157131 and 20040109877 (the disclosure of each of which is incorporated by reference herein), which disclose an attenuated virus lacking a functional NS1 gene. The NS1 gene may be completely deleted or partially deleted or altered by mutation such that there is no functional expression of the NS1 gene in the virus. Virus particles lacking the NS1 gene demonstrate an attenuated phenotype compared to wildtype virus.

After production of the attenuated virus, the vaccine is prepared using standard methods. The virus is purified using standard methods known in the art, for example using size exclusion chromatography, high-speed (ultra)centrifugation or sucrose gradients.

Subunit vaccines are killed vaccines. Production of subunit vaccine involves isolating a portion of the virus that activates the immune system. In the case of influenza, subunit vaccines have been prepared using purified HA and NA, but any mixture of viral proteins is used to produce a subunit vaccine. Generally, the viral protein, such as HA is extracted from recombinant virus forms and the subunit vaccine is formulated to contain a mixture of these viral proteins from different strains.

Split vaccines are killed vaccines produced by treating an enveloped virus with detergent to solubilize the proteins in the envelope. In the case of influenza virus, HA and NA become solubilized. In one embodiment, nonionic detergents are used for producing split vaccines. Examples of non-ionic detergents, include, but are not limited to, Nonanoyl-N-Methylfucamide (Mega 9), Triton X-100, Octylglucoside, Digitonin, C12E8, Lubrol, Nonidet P-40, and Tween (for example Tween 20, 80 or 120).

Inactivated viral vaccines are prepared by inactivating the harvested virus and formulating it using known methods for use as a vaccine to induce an immune response in a mammal. Inactivation is carried out using agents including but not limited to formaldehyde, UV irradiation, glutaraldehyde, binary ethyleneimine (BEI), and beta-propiolactone. Inactivating agents are used at a concentration high enough to inactivate substantially all viral particle in the solution. By way of example and without limitation, virus inactivation with gamma irradiation is described in U.S. Pat. No. 6,254,873; inactivation with formalin is described in U.S. Pat. No. 6,254,873 and U.S. Pat. No. 6,635,246; inactivated with formaldehyde is described for JE-VAX®, Japanese encephalitis virus vaccine in Couch et al., J Infect Dis 1997; 176(Suppl 1):538-44; photodynamic inactivation by visible light is described in Wallis, et al., Journal of Immunology, 1963, 91: 677-682; inactivation with UV light is described in WO/2008/039494; chlorine inactivation is described in Rice E W, et al., Emerg Infect Dis [serial on the Internet]. 2007 October; inactivation with water-insoluble, hydrophobic polycations, e.g., N,N-dodecyl methyl-polyethylenimine (PEI), painted onto surfaces is described Halder et al., Proc. Natl. Acad. Sci. USA 103:17667-17671, 2006; thermal inactivation is described in Thomas et al., Journal of Food Protection. 70:674-680; inactivation with betapropiolactone (as used for production of Inflexal V and Fluvirin) is described in EUROPEAN PHARMACOPOEIA 5.0; inactivation by binary ethylenimine is described in U.S. Pat. No. 6,803,041. The disclosures of each of these documents is incorporated by reference for their teaching of virus inactivation. It is contemplated that during the inactivation step, purification of subunits, and/or splitting is performed before or after purification of the virus from cell culture. For example, production of an inactivated virus vaccine, may involve removal of cellular material, inactivation of virus, purification and solubilization of the viral envelope. In one embodiment, a reassortant virus described herein is grown and isolated from Vero cells as described in Kistner et al., Vaccine. 25:6028-36, 2007.

A vaccine is then prepared using standard adjuvants and vaccine preparations known in the art. Adjuvants include, but are not limited to, saponin, non-ionic detergents, vegetable oil, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-s-n-glycero-3-hydroxyphosphoryloxy)-ethylamine, BCG (bacille Calmette-Guerin) *Corynebacterium parvum*, ISCOMs, nano-beads, squalene, and block copolymers, which are contemplated for use alone or in combination.

ISCOM is an acronym for Immune Stimulating Complex, described initially in Morein et al. (Nature 308:457-460, 1984). ISCOM's are a novel vaccine delivery system and are unlike conventional adjuvants. An ISCOM is formed in two ways. In some embodiments, the antigen is physically incorporated in the structure during its formulation. In other embodiments, an ISCOM-matrix (as supplied by, for example, Isconova) does not contain antigen but is mixed with the antigen of choice by the end-user prior to immunization. After mixing, the antigens are present in solution with the ISCOM-matrix but are not physically incorporated into the structure.

In one embodiment, the adjuvant is an oil in water emulsion. Oil in water emulsions are well known in the art, and have been suggested to be useful as adjuvant compositions (EP 399843; WO 95/17210, U.S. Patent Publication No. 20080014217). In one embodiment, the metabolizable oil is present in an amount of 0.5% to 20% (final concentration) of the total volume of the antigenic composition or isolated virus, at an amount of 1.0% to 10% of the total volume, or in an amount of 2.0% to 6.0% of the total volume.

In some embodiments, oil-in-water emulsion systems useful as adjuvant have a small oil droplet size. In certain embodiments, the droplet sizes will be in the range 120 to 750 nm, or from 120 to 600 nm in diameter.

In order for any oil in water composition to be suitable for human administration, the oil phase of the emulsion system comprises a metabolizable oil. The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolizable oil is squalene. Squalene (2,6,10,15,19,23-Hexamethyl-2,6,10,14, 18,22-tetracosahexaene) is an unsaturated oil which is found in large quantities in shark-liver oil, and in lower quantities in olive oil, wheat germ oil, rice bran oil, and yeast, and is a particularly suitable oil for use in this invention. Squalene is a metabolizable oil by virtue of the fact that it is an intermediate in the biosynthesis of cholesterol (Merck index, 10th Edition, entry no. 8619). Exemplary oils useful for an oil in water emulsion, include, but are not limited to, sterols, tocols, and alpha-tocopherol.

In additional embodiments, immune system stimulants are added to the vaccine and/or pharmaceutical composition. Immune stimulants include: cytokines, growth factors, chemokines, supernatants from cell cultures of lymphocytes, monocytes, or cells from lymphoid organs, cell preparations and/or extracts from plants, cell preparation and, or extracts from bacteria (e.g., BCG, mycobacterium, *Corynebacterium*), parasites, or mitogens, and novel nucleic acids derived from other viruses, or other sources (e.g. double stranded RNA, CpG) block co-polymers, nano-beads, or other compounds known in the art, used alone or in combination.

Particular examples of adjuvants and other immune stimulants include, but are not limited to, lysolecithin; glycosides (e.g., saponin and saponin derivatives such as Quil A (QS7 and QS21) or GPI-0100); cationic surfactants (e.g. DDA); quaternary hydrocarbon ammonium halogenides; pluronic polyols; polyanions and polyatomic ions; polyacrylic acids, non-ionic block polymers (e.g., Pluronic F-127); and 3D-MPL (3 de-O-acylated monophosphoryl lipid A). See e.g., U.S. Patent Publication Nos. 20080187546 and 20080014217.

Immunoassays

Various techniques are known in the art for detecting immunospecific binding of an antibody to an antigen which are useful to detect the antigenicity and induction of an immune response of a reassortant virus, antigenic composition or vaccine of the present invention. An early method of detecting interaction between an antigen and an antibody involved detection and analysis of the complex by precipitation in gels. A further method of detecting an antigen-antibody binding pair includes the use of radioiodinated detector antibodies or a radioiodinated protein which is reactive with IgG, such as Protein A. These early methods are well known to persons skilled in the art, as reviewed in Methods in Enzymology 70:166-198, 1980.

Serological assays are widely used in the determination of influenza diagnosis as well as in research studies regarding the epidemiology and antigenicity of viral strains. In particular, the hemagglutinin inhibition (HI or HAI) assay is widely used (Meisner et al., J Virol. 82:5079-83, 2008; Couch et al., Vaccine. 25:7656-63, 2007). The HI assay is also useful to show the antigenicity of the modified HA molecule, and assist in the characterization of the modified HA protein as more or less antigenic than a non-modified HA protein.

The HI assay determines the ability of antibodies from a serum sample to bind with a standardized reference. In the HI assay, serial dilutions (titers) of serum sample are mixed with standard amounts of erythrocytes and their association into complexes is detected visually. The lowest level of titered serum that results in a visible complex is the assay result.

A single radial diffusion (SRD) assay was developed by Wood et al. (J Biol Standardization 5:237-47, 1997) which determines the level of HA antigen in a sample. The SRD assay compares the zone of diffusion sites of a reference antigen and a test antigen (e.g., a vaccine) when the antigen are bound by HA-specific antibodies.

The SRD assay and other assays as described above and known in the art may be used to determine the amount of HA in a vaccine sample for preparation of a vaccine comprising a predetermined amount of HA antigen.

Pharmaceutical Formulations and Administration

The administration of the vaccine composition is generally for prophylactic purposes. The prophylactic administration of the composition serves to prevent or attenuate any subsequent infection. A "pharmacologically acceptable" composition is one tolerated by a recipient patient. It is contemplated that an effective amount of the vaccine is administered. An "effective amount" is an amount sufficient to achieve a desired biological effect such as to induce enough humoral or cellular immunity. This may be dependent upon the type of vaccine, the age, sex, health, and weight of the recipient. Examples of desired biological effects include, but are not limited to, production of no symptoms, reduction in symptoms, reduction in virus titer in tissues or nasal secretions, complete protection against infection by influenza virus, and partial protection against infection by influenza virus.

A vaccine or composition of the present invention is physiologically significant if its presence results in a detectable change in the physiology of a recipient patient that enhances at least one primary or secondary humoral or cellular immune response against at least one strain of an infectious influenza virus. The vaccine composition is administered to protect against viral infection. The "protection" need not be absolute, i.e., the influenza infection need not be totally prevented or eradicated, if there is a statistically significant improvement compared with a control population or set of patients. Protection may be limited to reducing the severity or rapidity of onset of symptoms of the influenza virus infection.

In one embodiment, an attenuated or inactivated vaccine composition of the present invention is provided either before the onset of infection (so as to prevent or attenuate an anticipated infection) or after the initiation of an actual infection, and thereby protects against viral infection.

In one aspect, methods of the invention include a step of administration of a pharmaceutical composition. The virus, antigenic composition or vaccine is administered in any means known in the art, including via inhalation, intranasally, orally, and parenterally. Examples of parental routes of administration include intradermal, intramuscular, intravenous, intraperitoneal and subcutaneous administration.

In one embodiment, influenza vaccine administration is based on the number of hemagglutinin units (HAU) per dose. One HAU is defined as the quantity of antigen required to achieve 50% agglutination in a standard hemagglutinin assay with chicken red blood cells. Avian influenza virus vaccines as described herein are effective in formulations comprising HA units (HAU) between about 10 ng and about 1 µg, between about 20 ng and about 500 ng, between about 50 ng and about 250 ng, between about 75 ng and about 200 ng, about 100 ng, about 125 ng, about 150 ng, or about 175 ng. In a related embodiment, a vaccine composition comprising an inactivated virus comprises an amount of virus corresponding to about 0.1 to about 200 µg of hemagglutinin protein/ml, or any range or value therein. In a related embodiment, a vaccine composition of the present invention comprises from about 10² to 10⁹ plaque forming units (PFU)/ml, or any range or value therein, where the virus is attenuated. In some embodiments, the vaccine composition comprises about 10², about 10³, about 10⁴, about 10⁵, about 10⁶, about 10⁷, about 10⁸ or about 10⁹ PFU/ml. It is further contemplated that the vaccine composition comprises from 10² to about 10⁴ PFU/ml, from about 10⁴ to about 10⁶ PFU/ml, or from about 10⁶ to about 10⁹ PFU/ml.

In another aspect. inactivated flu vaccine is quantified by a single radial diffusion (SRD) assays (see Kistner et al., Vaccine (2007) 25:6028-36, and Wood, et al., J. Biol. Stand. (1997) 5:237-247) and expressed in micrograms hemagglutinin (per ml or per dose). In one embodiment, the dose of a seasonal vaccine is 15 µg per strain, 45 µg in total in three dosages. For (pre)pandemic vaccines the dose typically depends on the adjuvant. In one aspect, the dose range is 1 µg to 15 µg per vaccine, and in some preparations, up to 75 µg per vaccine are useful. In one embodiment, the vaccine dose is administered at a dose from 1 µg to 100 µg HA. In a further embodiment, the vaccine comprises an HA content of 1 µg to 30 µg per vaccine. In related embodiments, the vaccine dose is administered at 1 µg, at 3 µg, at 5 µg, at 7.5 µg, at 10 µg, at 12.5 µg, at 15 µg, at 20 µg, at 25 µg, or at 30 µg HA, or in any amount up to 100 µg as necessary. It is contemplated that, in some embodiments, the dose of vaccine is adjusted based on the adjuvant used for vaccine preparation.

Accordingly single vaccine dosages include those having about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, and more than 100 µg hemagglutinin provided in single or multiple dosages at the same or different amount of hemagglutinin.

It is further contemplated that in certain embodiments, the virus or antigenic composition is administered in doses comprising similar HA units or pfu as contemplated for vaccine administration.

When administered as a solution, the vaccine is prepared in the form of an aqueous solution. Such formulations are known the art, and are prepared by dissolution of the antigen and other appropriate additives in the appropriate solvent. Such solvents include water, saline, ethanol, ethylene glycol, and glycerol, for example. Suitable additives include certified dyes and antimicrobial preservatives, such as thimerosal (sodium ethylmercuithiosalicylate). Such solutions may be stabilized using standard methods, for example, by addition of partially hydrolyzed gelatin, sorbitol, or cell culture medium and may be buffered using standard methods, using, for example reagents such as sodium hydrogen phosphate, sodium dihydrogen, phosphate, potassium hydrogen phosphate and/or potassium dihydrogen phosphate or TRIS. Liquid formulations may also include suspensions and emulsions. The preparation of suspensions include, for example using a colloid mill, and emulsions include for example using a homogenizer.

In one embodiment, it is contemplated that the vaccine carrier is a polymeric delayed release system. Synthetic polymers are useful in the formulation of a vaccine to effect the controlled release of antigens using well-known techniques in the art.

Additional aspects and details of the invention will be apparent from the following examples, which are intended to be illustrative rather than limiting.

EXAMPLES

Example 1

Generation of Attenuated A/Vietnam/1203/04 Strain with Modified Cleavage Site by Reverse Genetics Virus strain A/Vietnam/1203/04 (H5N1) is a highly pathogenic strain that was isolated from fatal human influenza case. In order to attenuate this strain the polybasic stretch of amino acids (RRRK (SEQ ID NO: 15)) at the HA cleavage site was eliminated. Additional substitutions (R→T and K→T) were introduced to prevent reformation of the polybasic amino acids by polymerase stuttering as described by Horimoto et al., (Vaccine. 24:3669-76, 2006). This modification diminish the major pathogenicity factor of highly pathogenic avian influenza virus and convert it to the low pathogenic phenotype.

Vero cells were obtained from the European Collection of Cell Cultures (ECACC, Salisbury, Wiltshire SP4 0JG, UK) at passage 134. Vero cells were cultivated in OPTI-PRO® (Gibco, Carlsbad, Calif.) medium supplemented with 4 mM L-glutamine.

Virus was propagated in Vero cells in OPTI-PRO® medium containing 5 µg/ml of trypsin (Sigma, St. Louis, Mo.) at 37° C. and 5% $CO_2$. The infectious titer of virus was determined by Standard TCID50 analysis. Hemagglutination assay was performed with 0.5% suspension of chicken red blood cells. Virus growth with or without trypsin was determined by standard plaque assay test on Vero cells in OPTI-PRO® medium containing 4 mM L-glutamine; 5 µg/ml trypsin, 0.01% DEAE-dextran (Sigma), 0.6% agar (Sigma) and expressed in plaque forming units (pfu).

The virus A/Vietnam/1203/04 (H5N1) with a modified cleavage site in HA protein was constructed. cDNAs corresponding to A/Vietnam/1203/04 PB2, PB1, PA, HA, NA, NP, M and NS segments were synthesized at Geneart AG (Regensburg, Germany) according to the sequences published in GenBank (accession numbers: AY818135 for HA, AY818141 for NA, AY818144 for M, AY818138 for NP, AY818147 for NS, AY818132 for PA, AY818129 for PB1, and AY818126 for PB2).

Since viral non-coding regions (NCRs) for the A/Vietnam/1203/04 segments were only partially available, NCRs derived from the respective A/Hong Kong/213/03 segments were added to the Vietnam/1203/2004 coding sequences (accession numbers for A/Hong Kong/213/03 HA: AB212054; NA: AB212056; M: AB212057; NP: AB212055; NS: AB212058; PA: AB212053; PB1: AB212052; PB2: AB212050).

The HA polybasic cleavage site of highly pathogenic strain A/Vietnam/1203/04 (H5N1) was replaced by the trypsin-dependent sequence TETR/GLF found in low-pathogenic H5 strains (FIG. 1). Modification of the HA gene included removal of the stretch of basic amino acids at the HA cleavage site and substitution of neighboring basic amino acids arginine (R) and lysine (K) to threonine (T), NTPQRERRRKKRGLFGAI (SEQ ID NO: 16)→NT-PQTETRGLFGAI (SEQ ID NO: 17), in order to prevent possible reversion to the wild type phenotype.

FIG. 1 shows the modification of the HA cleavage site nucleotide sequences of the viral genes. NCRs derived from A/Hong Kong/213/03 are underlined in FIG. 1. cDNA copies of genomic fragments were obtained by PCR and the PCR products were used for transfection of Vero cells. Transfection was performed according to the method of Hoffmann e al. (Proc. Natl. Acad. Sci. (USA) 97:6108-113, 2000) using eight cDNAs containing the complete viral genome.

Transfected Vero cells were seeded in a 6-well plate in serum-containing transfection medium (DMEM/F12+2 mM L-glutamine+10% FCS). Cells were incubated at 37° C. Six hours post transfection medium was replaced by serum-free OPTI-PRO® medium supplemented with 4 mM L-glutamine and 1 µg/ml trypsin. After 24 hours additional serum-free medium containing 10 µg of trypsin was added to the supernatant. After 72 hours supernatant was harvested and used for one more additional passage on fresh Vero cell (blind passage). Incubation of this passage lasted until the development of 100% cytopathic effect (CPE) was observed and then supernatant was harvested. Resultant virus was named A/Vietnam/1203/04 (H5N1)-HAatt or attVN1203.

Two sequential virus passages of rescued virus were performed on Vero cells in limiting dilutions. For this purpose a 24-well plate of confluent Vero cells was infected with 10-fold dilutions of harvested virus made in 4 repeats. In 2 days two wells at dilution (−5) were harvested and used for the 2nd step. The second step was carried out in the same way. Virus, harvested after 2 days at dilution (−6), was used for the production of virus stock. T150 cm$^2$ Roux-flask with a confluent monolayer of Vero cells was infected with virus harvested in the last passage using a multiplicity of infection (moi) 0.0005. Following a 30 min incubation at room temperature inoculum was removed and 50 ml of serum-free medium supplemented with 5 µg/ml trypsin were added. In 48 hours, 100% CPE had developed and supernatant was harvested, clarified by centrifugation at 160 g for 10 minutes, aliquoted for 1 ml in Cryo tubes and frozen at −80° C.

The infectious titer of A/Vietnam/1203/04-HAatt virus stock produced on Vero cells was determined by titration using TCID50 assay on Vero cells. Two independent titrations were performed. The results are shown in Table 2. Compared to propagation in eggs, the virus titer from Vero cell production was approximately 10-fold higher.

TABLE 2

Infectious titer of A/Vietnam/1203/04 (H5N1)-HAatt virus stock

| Experiment | Infectious titer, log10TCID50/ml |
|---|---|
| 1 | 8.87 |
| 2 | 8.55 |

The sequence of the HA gene of A/Vietnam/1203/04 (H5N1)-HAatt (H5N1) virus was engineered in a way to eliminate the polybasic stretch of amino acids at the HA cleavage site. This modification converted it to the low pathogenic phenotype which does not present any threat for humans.

To confirm the low pathogenic phenotype of obtained A/Vietnam/1203/04 (H5N1)-HAatt strain, the ability to produce plaques without trypsin was determined. In a plaque assay on Vero cells in the presence of trypsin A/Vietnam/1203/04 (H5N1)-HAatt virus produced plaques (titer 2×10$^7$ PFU/ml). In contrast the virus did not form plaques in the absence of trypsin corroborating the apathogenic phenotype of virus A/Vietnam/1203/04 (H5N1)-HAatt. To confirm the identity of the rescued virus to the cloned sequences, the sequences of HA and NA genes were verified. No changes were found in any of the sequenced genes.

These results demonstrate that the reassortant virus comprising the internal genes (backbone) from the A/Vietnam/1203/2004 (H5N1) strain of influenza and an attenuated HA and wild type NA gene from the same virus is adapted to growth in cell culture, and exhibits a reduced antigenicity compared to the wild type virus.

Example 2

Generation of Attenuated A/Indonesia/5/05 Strain (A/Vietnam/1203/04 2:6 Transfectant) with Modified Cleavage Site by Reverse Genetics Virus strain A/Indonesia/5/05 (H5N1) is a highly pathogenic strain that was isolated from a fatal human influenza case. In order to attenuate this strain, the polybasic stretch of amino acids (RRKK [SEQ ID NO: 21]) at the HA cleavage site was eliminated. Additional substitutions (R→T and S→T) were introduced to prevent reformation of the polybasic amino acids (Horimoto et al., Vaccine. 24:3669-76, 2006). This modification should diminish the major pathogenicity factor of highly pathogenic avian influenza virus and convert it to the low pathogenic phenotype.

Cell culture and viral propagation was carried out as described above. Virus A/Indonesia/5/05 (H5N1)-like with modified cleavage site in the HA protein was constructed. cDNAs corresponding to A/Indonesia/5/05 HA and NA and A/Vietnam/1203/04 PB2, PB1, PA, NP, M and NS segments were synthesized at Geneart AG (Regensburg, Germany) according to the sequences published in GenBank (accession numbers: ISDN125873 for HA, ISDN125875 for NA, AY818144 for M, AY818138 for NP, AY818147 for NS, AY818132 for PAT AY818129 for PB1, and AY818126 for PB2).

Since viral non-coding regions (NCRs) for the A/Vietnam/1203/04 segments were only partially available, NCRs derived from the respective A/Hong Kong/213/03 segments were added to the A/Indonesia/5/05 and to the Vietnam/1203/2004 coding sequences (accession numbers for A/Hong Kong/213/03 HA: AB212054; NA: AB212056; M: AB212057; NP: AB212055; NS: AB212058; PA: AB212053; PB1: AB212052; PB2:AB212050). The HA polybasic cleavage site of highly pathogenic strain A/Indonesia/5/05 (H5N1) was replaced by the trypsin-dependent sequence TETR/GLF found in low-pathogenic H5 strains (FIG. 2). Modification of the HA gene included removal of the stretch of basic amino acids at the HA cleavage site and substitution of neighboring basic amino acid R and S to T in order to prevent possible reversion to the wild type phenotype, as follows: NTPQRERRRKKRGLFGAI (SEQ ID NO: 16)→NTPQTETRGLFGAI (SEQ ID NO: 17). FIG. 2 shows the modification of the A/Indonesia/5/05 HA cleavage site and nucleotide sequences of the viral genes. NCRs derived from A/Hong Kong/213/03 are underlined.

cDNA copies of genomic fragments were obtained by PCR and the PCR products were used for transfection of Vero cells. Transfected Vero cells were seeded in a 6-well plate in serum-containing transfection medium (DMEM/F12+2 mM L-glutamine+10% FCS). Cells were incubated at 37° C. Six hours post transfection medium was replaced by serum-free OPTIPRO® medium supplemented with 4 mM L-glutamine and 1 µg/ml trypsin. After 24 hours, additional serum-free medium containing 10 µg of trypsin was added to the supernatant. After 72 hours, supernatant was harvested and used for one more additional passage on fresh Vero cell (blind passage). Incubation of this passage was maintained until the development of 100% cytopathic effect (CPE) and then supernatant was harvested. The resultant virus was named A/Indonesia/5/05 (H5N1)-HAatt or RG-attVN1203/ IN5/05.

Two sequential virus passages of rescued virus were performed on Vero cells in limiting dilutions. For this purpose, a 24-well plate of confluent Vero cells was infected with 10-fold dilutions of harvested virus made in 4 repeats. After two days two wells at dilution (−6) were harvested and used for the second step, which was carried out in the same manner. Virus harvested after 2 days at dilution (−6) was used for the production of virus stock. T150 cm² Roux-flask with a confluent monolayer of Vero cells was infected with virus harvested in the last passage using moi 0.0005. Following a 30 minute incubation at room temperature inoculum was removed and 50 ml of serum-free medium supplemented with 5 µg/ml trypsin were added. After 48 hours, 100% CPE developed and supernatant was harvested, clarified by centrifugation at 160 g for 10 minutes, aliquoted for 1 ml in Cryotubes and frozen at −80° C.

The infectious titer of A/Indonesia/5/05 (H5N1)-HAatt virus stock produced on Vero cells was estimated by titration using TCID50 assay on Vero cells. Two independent titrations were performed. The results are shown in Table 3.

TABLE 3

Infectious titer of A/Indonesia/5/05 (H5N1)-HAatt virus stock

| Experiment | Infectious titer, log10TCID50/ml |
|---|---|
| 1 | 9.04 |
| 2 | 8.72 |

The sequence of HA gene of A/Indonesia/5/05 (H5N1)-HAatt virus was engineered in a way to eliminate the polybasic stretch of amino acids at the HA cleavage site. This modification converted it to the low pathogenic phenotype which does not present any threat for humans. To confirm the low pathogenic phenotype of obtained A/Indonesia/5/05 (H5N1)-HAatt strain the ability to produce plaques without trypsin was determined. In a plaque assay on Vero cells in the presence of trypsin A/Indonesia/5/05 (H5N1)-HAatt virus produced plaques (titer 3×10⁷ PFU/ml). In contrast the virus did not form plaques in the absence of trypsin corroborating the apathogenic phenotype of virus A/Indonesia/5/05 (H5N1)-HAatt.

To confirm the identity of the rescued virus to the cloned sequences, the sequences of HA and NA genes were verified. No changes were found in any of the sequenced genes.

These results demonstrate that a reassortant virus comprising the internal genes (backbone) from the A/Vietnam/1203/2004 (H5N1) strain of influenza and an attenuated HA and wild type NA gene from a different influenza H5N1 strain (A/Indonesia/5/05) is adapted to growth in cell culture, and exhibits a reduced antigenicity compared to the wild type virus.

The growth of the attenuated virus in Vero cell culture was then compared to growth of an egg-adapted reverse genetics virus in Vero cells.

The influenza strain CDC RG Indo/05/2005 is a 6:2 reverse genetics strain with PR8 backbone (six internal genes derived from PR8) and the HA and NA genes derived from the A/Indonesia/05/2005 strain. This strain is egg-adapted and is the basis for conventional (egg-derived) inactivated H5N1 vaccines. The CDC RG Indo strain was passaged three times in Vero cells at two different temperatures, 32° C. and 37° C. at multiplicities of infection (MOI) of 0.01 to 0.0001. The titers are shown in Table 4. The initial log titers were in the range of 6.4-6.7 (32° C.) and 5.8-6.8 (37° C.). After three passages, titers were somewhat higher, 7.1-7.2 at 32° C. and 6.5-7.4 at 37° C. Thus, initial titers were low and passaging improved titers only slightly.

TABLE 4

TCID50 titers obtained with the egg-adapted CDC RG Indo/05/2005 strain.

| Vero | MOI[a] | P[b] 1 | P2 | p3 |
|---|---|---|---|---|
| 32° C. | 0.01 | 6.7[c] | 6.8 | 7.1 |
| | 0.001 | 6.6 | 6.7 | 7.2 |
| | 0.0001 | 6.4 | 6.8 | 7.2 |
| 37° C. | 0.01 | 6.8 | 7.1 | 7.0 |
| | 0.001 | 6.7 | 7.2 | 7.4 |
| | 0.0001 | 5.8 | 6.9 | 6.5 |

[a]Passage; MOI, multiplicity of infection;
[c]titer in TCID50/ml

The new influenza viruses Vietnam/1203/04 (H5N1)-HAatt virus grew to an average titer of 8.71 log 10 TCID50/ml. The titer of the A/Indonesia/5/05 (H5N1)-HAatt virus was 8.88 TCID50/ml (Examples 1 and 2). Compared to the matching egg-adapted strain CDC RG Indo/05/2005, the new strain grew at least two log steps higher than the egg-adapted virus.

Example 3

Safety and Efficacy of Reassortant Viruses

In order to determine the safety and efficacy of the reassortant virus, studies were carried out in vivo in mice and chickens. 10-12 week old Balb/c mice (Charles River, Sulzfeld, Germany) were challenged intranasally with increasing doses of the viruses as indicated in Table 4A and 4B (clinical symptoms: r, ruffled fur; h, hunched; m, matte (dull); d, dead; AST=average time to death).

In the first mouse experiment (Table 5A), mice were clinically monitored over a two week period. No major clinical symptoms were observed after challenge with the viruses RG-attVN1203 or the 6:2 Indonesia reassortant. The majority of mice showed no clinical symptoms at all; some mice had a ruffled fur within the first week and fully recovered in the second week.

In the second mouse experiment (Table 5B), doses were increased up to 1×10⁶ TCID50 per animal, given intranasally. This time, weight loss (WL), a reliable indicator of sickness, was monitored. No WL was observed with the H5N1 based RG viruses, all mice survived, indicating no virulence. The wild-type challenge control, the VN1203 and IN5/05H5N1 wild-type strains, killed the mice within 6 to 8 days.

To examine the safety of the reassortant virus in chickens, seven day old chickens (Spafas, Hungary) were challenged with increasing doses of the viruses as indicated in Table 5C and 5D. The animals were clinically monitored over a two week period.

As shown in Table 5C, in all chickens challenged intranasally with doses of 1×10⁵ and 1×10⁶ TCID50 per animal, no major clinical symptoms could be observed with the H5N1 based RG viruses. As expected, a BSL-2 control virus obtained from CDC (CDC RG Indo/05/2005, a pre-pandemic seed virus strain based on PR8) was also avirulent and non-pathogenic to chickens.

In order to confirm this result using a second route of application, chickens were challenged by intramuscular injection (Table 5D) at a dose of 1×10⁶ TCID50 per animal. Two control viruses, known to be avirulent for chickens, CDC RG Indo/05/2005 and NIBRG-14 (PR8-based reassortants with the and IN5/05 and VN1194 HA and NA genes, respectively) were included. No weight loss could be observed after challenge. All animals gained weight comparable to the control animals, chickens challenged with phosphate buffered saline (PBS). In the same experiment, chickens were challenged intranasally with the highly pathogenic H5N1 wild-type virus IN5/05. All chickens died peracutely after challenge within two days after challenge (Table 5D).

These in vivo experiments confirm that the modification of the polybasic cleavage site in the HA gene strongly attenuates the H5N1 virus.

HA and NA and A/Vietnam/1203/04 PB2, PB1, PA, NP, M and NS segments were synthesized at Geneart AG (Regensburg, Germany) according to the sequences published in GenBank (accession numbers: DQ407519 for HA, EF619973 for NA, EF541453 for M, AY818138 for NP, EF541456 for NS, AY818132 for PA, AY818129 for PB1, and AY818126 for PB2).

Since viral non-coding regions (NCRs) for the A/Vietnam/1203/04 segments were only partially available, NCRs derived from the respective A/Hong Kong/213/03 segments were added to the A/Indonesia/5/05 and to the Vietnam/1203/2004 coding sequences (accession numbers for A/Hong Kong/213/03 HA: AB212054; NA: AB212056; M: AB212057; NP: AB212055; NS: AB212058; PA: AB212053; PB1: AB212052; PB2:AB212050). The HA polybasic cleavage site of highly pathogenic strain A/Turkey/Turkey/1/05 was replaced by the trypsin-dependent

TABLE 5

| Expt | | animals number | chall/route | virus TCID50 | clinical monitoring symptoms | weight | survived/total | AST (days) | seroconversion HI and NT tests |
|---|---|---|---|---|---|---|---|---|---|
| A | H5N1-131/RG 08-01 mice | 6 | 1 × 10E3 in | RG-attVN1203 | — | n.d | 6/6. | n.a | n.d |
| | | 6 | 1 × 10E4 in | RG-attVN1203 | — | n.d | 6/6. | n.a | n.d |
| | | 6 | 1 × 10E5 in | RG-attVN1203 | — | n.d | 6/6. | n.a | n.d |
| | | 6 | 1 × 10E3 in | RG-attVN1203/IN5/05 | — | n.d | 6/6. | n.a | n.d |
| | | 6 | 1 × 10E4 in | RG-attVN1203/IN5/05 | — | n.d | 6/6. | n.a | n.d |
| | | 6 | 1 × 10E5 in | RG-attVN1203/IN5/05 | — | n.d | 6/6. | n.a | n.d |
| B | H5N1-RG 08-02 mice | 6 | 1 × 10E4 in | RG-attVN1203 | — | no weight loss | 6/6. | n.a | 6/6. |
| | | 6 | 1 × 10E5 in | RG-attVN1203 | — | no weight loss | 6/6. | n.a | 6/6. |
| | | 6 | 1 × 10E6 in | RG-attVN1203 | — | no weight loss | 6/6. | n.a | 6/6. |
| | | 6 | 1 × 10E4 in | RG-attVN1203/IN5/05 | — | no weight loss | 6/6. | n.a | 6/6. |
| | | 6 | 1 × 10E5 in | RG-attVN1203/IN5/05 | — | no weight loss | 6/6. | n.a | 6/6. |
| | | 6 | 1 × 10E6 in | RG-attVN1203/IN5/05 | — | no weight loss | 6/6. | n.a | 6/6. |
| | | 6 | 1 × 10E5 in | VN1203 wt | r, h, m, d | n.d | 0/6. | 6 | n.d |
| | | 6 | 1 × 10E5 in | IN5/05 wt | r, h, m, d | n.d | 0/6. | 6-8. | n.d |
| C | H5N1-RG 08-03 chickens (7 days) | 5 | 1 × 10E5 in | RG-attVN1203 | — | no weight loss | 5/5. | n.a | 0/5. |
| | | 5 | 1 × 10E6 in | RG-attVN1203 | — | no weight loss | 5/5. | n.a | 0/5. |
| | | 5 | 1 × 10E5 in | RG-attVN1203/IN5/05 | — | no weight loss | 5/5. | n.a | 0/5. |
| | | 5 | 1 × 10E6 in | RG-attVN1203/IN5/05 | — | no weight loss | 5/5. | n.a | 0/5. |
| | | 5 | 1 × 10E5 in | RG-CDC-IN5/05 | — | no weight loss | 5/5. | n.a | 0/5. |
| | | 5 | n.a | PBS | — | no weight loss | 5/5. | n.a | 0/5. |
| D | H5N1-RG 08-04 chickens (7 days) | 6 | 1 × 10E6 im | RG-attVN1203 | — | no weight loss | 6/6. | n.a | 6/6. |
| | | 6 | 1 × 10E6 im | RG-attVN1203/IN5/05 | — | no weight loss | 6/6. | n.a | 6/6. |
| | | 6 | 1 × 10E6 im | RG-CDC-IN5/05 | — | no weight loss | 6/6. | n.a | 6/6. |
| | | 6 | 1 × 10E6 im | NIBRG-14 | — | no weight loss | 6/6. | n.a | 6/6. |
| | | 4 | n.a | PBS | — | no weight loss | 6/6. | n.a | |
| | | 6 | 1 × 10E5 in | IN5/05 wt | death (peracute) | n.d | 0/6. | 2 | n.d |

Example 4

Generation of Attenuated A/Turkey/Turkey/1/05 Strain with Modified Cleavage Site by Reverse Genetics Virus strain A/turkey/Turkey/1/05 (H5N1) is a highly pathogenic strain that was isolated from a fatal avian influenza case. In order to attenuate this strain, the polybasic stretch of amino acids (RRRK (SEQ ID NO: 15)) at the HA cleavage site was eliminated. Additional substitutions (R→T and K→T) were introduced to prevent reformation of the polybasic amino acids (Horimoto et al., Vaccine. 24:3669-76, 2006). This modification should diminish the major pathogenicity factor of highly pathogenic avian influenza virus and convert it to the low pathogenic phenotype.

Cell culture and viral propagation was carried out as described above. Virus A/Turkey/Turkey/1/05 (H5N1)-like with modified cleavage site in the HA protein was constructed. cDNAs corresponding to A/turkey/Turkey/1/05 sequence TETR/GLF (See SEQ ID NO: 19) found in low-pathogenic H5 strains (FIG. 3). Modification of the HA gene included removal of the stretch of basic amino acids at the HA cleavage site and substitution of neighboring basic amino acid R and K to T in order to prevent possible reversion to the wild type phenotype, as follows: NSPQR-ERRRKKRGLFGAI (SEQ ID NO: 18)→NSPQTETRGLF-GAI (SEQ ID NO: 19). FIG. 3 shows the modification of the A/Turkey/Turkey/1/05 HA cleavage site and nucleotide sequences of the viral genes. NCRs derived from A/Hong Kong/213/03 are underlined.

cDNA copies of genomic fragments were obtained by PCR and the PCR products were used for transfection of Vero cells. Transfected Vero cells were seeded in a 6-well plate in serum-containing transfection medium (DMEM/F12+2 mM L-glutamine+10% FCS). Cells were incubated at 37° C. Six hours post transfection medium was replaced by serum-free OPTIPRO® medium supplemented with 4 mM L-glutamine, 1 µg/ml trypsin AND 0.25 µg/ml amphotericin B. After 24 hours, additional serum-free medium containing 10 μg of trypsin was added to the supernatant. After 72 hours, supernatant was harvested and used for two additional passages on fresh Vero cell (blind passage). Incubation of this passage was maintained until the development of 100% cytopathic effect (CPE) and then supernatant was harvested. The resultant virus was named A/turkey/Turkey/1/05 (H5N1)-HAatt or RG-attVN1203/TT/1/05.

An A/turkey/Turkey/1/05 viral stock was produced as described above. The infectious titer of A/turkey/Turkey/1/05 (H5N1)-HAatt virus stock produced on Vero cells was estimated by titration using TCID50 assay on Vero cells. Two independent titrations were performed. The results are shown in Table 6.

TABLE 6

Infectious titer of RG-attVN1203/TT/1/05 virus stock

| Experiment | Infectious titer, log10TCID50/ml |
|---|---|
| 1 | 8.83 |
| 2 | 8.85 |

To confirm the identity of the rescued virus to the cloned sequences, the sequences of HA and NA genes were verified. No changes were found in any of the sequenced genes.

These results demonstrate that a reassortant virus comprising the internal genes (backbone) from the A/Vietnam/1203/2004 (H5N1) strain of influenza and an attenuated HA and wild type NA gene from a different influenza H5N1 strain (A/turkey/Turkey/1/05) is adapted to growth in cell culture.

Example 5

Generation of Attenuated A/Anhui/01/05 Strain with Modified Cleavage Site by Reverse Genetics Virus strain A/Anhui/01/05 (H5N1) is a highly pathogenic strain that was isolated from a fatal human influenza case in China. In order to attenuate this strain, the polybasic stretch of amino acids (RRRK (SEQ ID NO: 15)) at the HA cleavage site was eliminated. Additional substitutions (L→Q, R→T and K→T) were introduced to prevent reformation of the polybasic amino acids (Horimoto et al., Vaccine. 24:3669-76, 2006). This modification should diminish the major pathogenicity factor of highly pathogenic avian influenza virus and convert it to the low pathogenic phenotype.

Cell culture and viral propagation was carried out as described above. Virus A/Anhui/01/05 (H5N1)-like with modified cleavage site in the HA protein was constructed. cDNAs corresponding to A/Anhui/01/05 HA and NA and A/Vietnam/1203/04 PB2, PB1, PA, NP, M and NS segments were synthesized at Geneart AG (Regensburg, Germany) according to the sequences published in GenBank (accession numbers: DQ371928 for HA, EU128239 for NA, EF541453 for M, AY818138 for NP, EF541456 for NS, AY818132 for PA, AY818129 for PB1, and AY818126 for PB2).

Since viral non-coding regions (NCRs) for the A/Vietnam/1203/04 segments were only partially available, NCRs derived from the respective A/Hong Kong/213/03 segments were added to the A/Indonesia/5/05 and to the Vietnam/1203/2004 coding sequences (accession numbers for A/Hong Kong/213/03 HA: AB212054; NA: AB212056; M: AB212057; NP: AB212055; NS: AB212058; PA: AB212053; PB1: AB212052; PB2:AB212050). The HA polybasic cleavage site of highly pathogenic strain A/Anhui/01/05 was replaced by the trypsin-dependent sequence TETR/GLF found in low-pathogenic H5 strains (FIG. 4). Modification of the HA gene included removal of the stretch of basic amino acids at the HA cleavage site and substitution of neighboring basic amino acids L to Q, and R and K to T in order to prevent possible reversion to the wild type phenotype, as follows: NSPLRERRRKKRGLFGAI (SEQ ID NO: 20)→NSPQTETRGLFGAI (SEQ ID NO: 19). FIG. 4 shows the modification of the A/Anhui/1/05 HA cleavage site and nucleotide sequences of the viral genes. NCRs derived from A/Hong Kong/213/03 are underlined.

cDNA copies of genomic fragments were obtained by PCR and the PCR products were used for transfection of Vero cells. Transfected Vero cells were seeded in a 6-well plate in serum-containing transfection medium (DMEM/F12+2 mM L-glutamine+10% FCS). Cells were incubated at 37° C. Six hours post transfection medium was replaced by serum-free OPTIPRO® medium supplemented with 4 mM L-glutamine, 1 μg/ml trypsin AND 0.25 μg/ml amphotericin. After 24 hours, additional serum-free medium containing 10 μg of trypsin was added to the supernatant. After 72 hours, supernatant was harvested and used for two additional passages on fresh Vero cells. Incubation of this passage was maintained until the development of 100% cytopathic effect (CPE) and then supernatant was harvested. The resultant virus was named A/Anhui/01/05 (H5N1)-HAatt or RG-attVN1203/AH/1/05.

An A/Anhui/01/05 viral stock was produced as described above. The infectious titer of RG-attVN1203/AH/1/05 virus stock produced on Vero cells was estimated by titration using TCID50 assay on Vero cells. Two independent titrations were performed. The results are shown in Table 7.

TABLE 7

Infectious titer of RG-attVN1203/AH/1/05 virus stock

| Experiment | Infectious titer, log10TCID50/ml |
|---|---|
| 1 | 8.75 |
| 2 | 8.50 |

To confirm the identity of the rescued virus to the cloned sequences, the sequences of HA and NA genes were verified. No changes were found in any of the sequenced genes.

These results demonstrate that a reassortant virus comprising the internal genes (backbone) from the A/Vietnam/1203/2004 (H5N1) strain of influenza and an attenuated HA and wild type NA gene from a different influenza H5N1 strain (A/Anhui/1/05) is adapted to growth in cell culture.

Example 6

Administration of Reassortant Virus Vaccine In Vivo

In order to determine the in vivo efficacy of the recombinant reassortant virus (whole virus) expressing H5N1 internal and HA and NA genes, the virus is administered to subject animals using techniques well-known in the art. For example, Kistner et al., (Vaccine. 25:6028-36, 2007) describes administration of viral vaccine comprising whole, inactivated H5N1 viral strain A/Vietnam/1203/2004 to subject mice and assessing the ability of the vaccine to protect against infection of the mice upon rechallenge with live virus.

Additionally, Ehrlich et al., (N Engl J Med. 358:2573-84, 2008) describes a clinical trial in human patients comprising administering a vaccine to an H5N1 pandemic influenza strain. Two doses of vaccine (21 days apart) comprising inactivated whole A/Vietnam/1203/2004 were administered to subjects, each dose containing 3.75 µg, 7.5 µg, 15 µg, or 30 µg of hemagglutinin antigen with alum adjuvant or 7.5 µg or 15 µg of HA antigen without adjuvant. Serologic analysis was performed at baseline and on days 21 and 42. Ehrlich demonstrated that the vaccine elicits an immune response in host subjects, and the host is protected against infection with several different virus strains.

Reassortant viruses, antigenic compositions or vaccines of the present invention are administered using the techniques described above or using other techniques known in the art.

Numerous modifications and variations in the invention as set forth in the above illustrative examples are expected to occur to those skilled in the art. Consequently only such limitations as appear in the appended claims should be placed on the invention.

What is claimed:

1. A purified recombinant reassortant influenza virus comprising:
   (i) internal gene segments PB1, PB2, PA, M, NP, and NS from a first H5N1 influenza virus A strain; and
   (ii) hemagglutinin (HA) and neuraminidase (NA) gene segments from a second H5N1 influenza virus A strain, wherein the HA and NA gene segments are from the same viral strain,
   wherein the first and second influenza A strains are different strains of influenza virus, wherein both the first strain and the second strain are of H5N1 subtype, and
   wherein the recombinant reassortant influenza virus is attenuated by modification at a polybasic cleavage site on its HA gene segment, the site having an amino acid sequence selected from the group consisting of RRRK (SEQ ID NO: 15) and RRKK (SEQ ID NO: 21), the modification being mutation RERRRKKR (SEQ ID NO: 13)→TETR (SEQ ID NO: 14).

2. The reassortant virus of claim 1, wherein the internal gene segments are from a first H5N1 clade, and the HA and NA gene segments are from a second H5N1 clade.

3. The reassortant virus of claim 1, wherein the HA and NA gene segments and the internal gene segments are from the same H5N1 clade.

4. The reassortant virus of claim 1 characterized by an ability to propagate in mammalian cell culture.

5. The reassortant virus of claim 4, wherein the mammalian cells are selected from the group consisting of MRC-5, MRC-9, Lederle 130, Chang liver, WI-38, U937, Vero, CV-1, IMR-90, IMR-91, MDCK, MDBK, HEK, H9, CEM, CD4-expressing HUT78, PerC6, BHK-21, BSC, and LLC-MK2.

6. The reassortant virus of claim 4, wherein the mammalian cell culture is a Vero cell culture.

7. The reassortant virus of claim 1, said HA and NA gene segments from an H5N1 strain being selected from the group consisting of A/Vietnam/1203/2004, A/Hong Kong/213/03, A/Indonesia/5/05 (H5N1), A/turkey/Turkey/01/2005 (H5N1), A/Anhui/1/05 (H5N1), A/Cambodia/R0405050/2007 (H5N1), A/chicken/Nakorn-Patom/Thailand/CU-K2/04, A/chicken/Vietnam/C58/04, A/quail/Vietnam/36/04, and A/HK/156/97.

8. The reassortant virus of claim 1, wherein said internal gene segments are from the H5N1 strain A/Vietnam/1203/2004.

9. The reassortant virus of claim 1, wherein the HA and NA gene segments are from the H5N1 strain A/Vietnam/1203/2004.

10. The reassortant virus of claim 1, wherein the HA and NA gene segments are from the H5N1 strain A/Indonesia/5/05.

11. A recombinant antigenic reassortant influenza virus composition comprising,
    (i) internal gene segments PB1, PB2, PA, M, NP, and NS from a first H5N1 influenza virus A strain; and
    (ii) hemagglutinin (HA) and neuraminidase (NA) gene segments from a second H5N1 influenza virus A strain, the HA and NA gene segments being from the same viral strain,
    wherein the first and second influenza A strains are different strains of influenza virus, wherein both the first strain and the second strain are of H5N1 subtype, and
    wherein the recombinant antigenic reassortant influenza virus is attenuated by modification at a polybasic cleavage site on its HA gene segment, the site having an amino acid sequence selected from the group consisting of RRRK (SEQ ID NO: 15) and RRKK (SEQ ID NO: 21), the modification being mutation RERRRKKR (SEQ ID NO: 13)→TETR (SEQ ID NO: 14).

12. The antigenic composition of claim 11 further comprising a pharmaceutically acceptable carrier.

13. A vaccine comprising a recombinant reassortant influenza virus, the virus comprising:
    (i) a polynucleotide encoding for PB1, a polynucleotide encoding for PA, a polynucleotide encoding for PB2, a polynucleotide encoding for M, a polynucleotide encoding for NP, and a polynucleotide encoding for NS, the PB1, PA, PB2, M, NP, and NS being from a first strain of an influenza A virus subtype H5N1; and
    (ii) a polynucleotide encoding for surface protein HA and a polynucleotide encoding for surface protein NA, the HA and NA being from a second strain of an influenza virus A subtype H5N1;
    wherein the first and second influenza A strains are different strains of influenza virus, wherein both the first strain and the second strain are of H5N1 subtype,
    wherein the polynucleotides are operatively linked to allow packaging of the reassorted polynucleotides into a virion, and
    wherein the recombinant reassortant influenza virus is attenuated by modification at a polybasic cleavage site on its HA gene segment, the site having an amino acid sequence selected from the group consisting of RRRK (SEQ ID NO: 15) and RRKK (SEQ ID NO: 21), the modification being mutation RERRRKKR (SEQ ID NO: 13)→TETR (SEQ ID NO: 14).

14. The vaccine of claim 13 further comprising an adjuvant.

15. The vaccine of claim 13, wherein the vaccine is an inactivated vaccine.

16. The vaccine of claim 13 comprising an HA content of from 1 μg to 100 μg HA.

17. A method for eliciting an immune response to at least one pandemic influenza virus strain in a subject, comprising administering an antigenic composition of claim 11 or a vaccine of claim 13 in an amount effective to attenuate an infection of at least one H5N1 influenza virus strain.

18. A method for attenuating an infection of a subject by an H5N1 influenza virus comprising, administering to the subject an effective amount of a virus of a claim 1, an antigenic composition of claim 11 or a vaccine of claim 13.

19. The method of claim 18, wherein the vaccine comprises an HA content of from 1 μg to 100 μg HA.

20. A method of making a vaccine comprising a reassortant influenza virus comprising internal gene segments PB1, PB2, PA, M, NP, and NS a first H5N1 strain of influenza A virus, and hemagglutinin (HA) and neuraminidase (NA) gene segments from a second H5N1 strain of influenza A virus, the HA and NA gene segments being from the same viral strain and the HA gene being modified at a polybasic cleavage site set out in SEQ ID NO: 15 to produce an attenuated HA gene, the method comprising transfecting the reassortant influenza virus in mammalian cells under conditions suitable for growth of the reassortant influenza virus, wherein the modification at the polybasic cleavage site is mutation RERRRKKR (SEQ ID NO: 13)→TETR (SEQ ID NO: 14).

21. The reassortant virus of claim 1, wherein the gene segments comprise viral non-coding regions used in recombinant production of the virus.

22. The antigenic composition of claim 11, wherein the gene segments comprise viral non-coding regions used in recombinant production of the virus.

23. The vaccine of claim 13, wherein the gene segments comprise viral non-coding regions used in recombinant production of the virus.

\* \* \* \* \*

SEQUENCE LISTING

<160> NUMBER OF SEQ ID NOS: 21

<210> SEQ ID NO 1
<211> LENGTH: 1767
<212> TYPE: DNA
<213> ORGANISM: Artificial Sequence
<220> FEATURE:
<223> OTHER INFORMATION: Synthetic nucleotide

<400> SEQUENCE: 1

```
agcaaaagca ggggttcaat ctgtcaaaat ggagaaaata gtgcttcttt ttgcaatagt      60
cagtcttgtt aaaagtgatc agatttgcat tggttaccat gcaaacaact cgacagagca     120
ggttgacaca ataatggaaa agaacgttac tgttacacat gcccaagaca tactggaaaa     180
gaaacacaac gggaagctct gcgatctaga tggagtgaag cctctaattt tgagagattg     240
tagcgtagct ggatggctcc tcggaaaccc aatgtgtgac gaattcatca atgtgccgga     300
atggtcttac atagtggaga aggccaatcc agtcaatgac ctctgttacc caggggattt     360
caatgactat gaagaattga acacctatt gagcagaata aaccattttg agaaaattca     420
gatcatcccc aaaagttctt ggtccagtca tgaagcctca ttagggtga gctcagcatg     480 tccataccag ggaaagtcct ccttttcag aaatgtggta tggcttatca aaaagaacag     540
tacataccca acaataaaga ggagctacaa taataccaac caagaagatc ttttggtact     600 gtggggatt caccatccta atgatgcggc agagcagaca aagctctatc aaaacccaac     660
cacctatatt tccgttggga catcaacact aaaccagaga ttggtaccaa gaatagctac     720
tagatccaaa gtaaacgggc aaaatggaag gatggagttc ttctggacaa tttaaagcc     780 gaatgatgca atcaacttcg agagtaatgg aaatttcatt gctccagaat atgcatacaa     840
aattgtcaag aaagggggact caacaattat gaaaagtgaa ttggaatatg gtaactgcaa     900
caccaagtgt caaactccaa tgggggcgat aaactctagc atgccattcc acaatataca     960
ccctctcacc attggggaat gccccaaata tgtgaaatca aacagattag tccttgcgac    1020
tgggctcaga aatagccctc aaaccgagac ccgaggatta tttggagcta tagcaggttt    1080
tatagaggga ggatggcagg gaatggtaga tggttggtat gggtaccacc atagcaatga    1140 gcagggggagt gggtacgctg cagacaaaga atccactcaa aaggcaatag atggagtcac    1200
caataaggtc aactcgatca ttgacaaaat gaacactcag tttgaggccg ttggaaggga    1260
atttaacaac ttagaaagga atagagaa ttaacaag aagatggaag acgggttcct    1320
agatgtctgg acttataatg ctgaacttct ggttctcatg gaaaatgaga gaactctaga    1380
ctttcatgac tcaaatgtca agaacctta cgacaaggtc cgactacagc ttagggataa    1440
tgcaaaggag ctgggtaacg gttgtttcga gttctatcat aaatgtgata atgaatgtat    1500
ggaaagtgta agaaatggaa cgtatgacta cccgcagtat tcagaagaag cgagactaaa    1560
aagagaggaa ataagtggag taaaattgga atcaatagga atttaccaaa tactgtcaat    1620
```

| | |
|---|---:|
| ttattctaca gtggcgagtt ccctagcact ggcaatcatg gtagctggtc tatccttatg | 1680 |
| gatgtgctcc aatggatcgt tacaatgcag aatttgcatt taaatttgtg agttcagatt | 1740 |
| gtagttaaaa acacccttgt ttctact | 1767 |

<210> SEQ ID NO 2
<211> LENGTH: 1398
<212> TYPE: DNA
<213> ORGANISM: Artificial Sequence
<220> FEATURE:
<223> OTHER INFORMATION: Synthetic nucleotide

<400> SEQUENCE: 2

| | |
|---|---:|
| agcaaaagca ggagttcaaa atgaatccaa atcagaagat aataaccatc ggatcaatct | 60 |
| gtatggtaac tggaatagtt agcttaatgt tacaaattgg aacatgatc tcaatatggg | 120 |
| tcagtcattc aattcacaca gggaatcaac accaatctga accaatcagc aatactaatt | 180 |
| ttcttactga gaaagctgtg gcttcagtaa aattagcggg caattcatct ctttgcccca | 240 |
| ttaacggatg ggctgtatac agtaaggaca acagtataag gatcggttcc aaggggatg | 300 |
| tgtttgttat aagagagccg ttcatctcat gctcccactt ggaatgcaga actttctttt | 360 |
| tgactcaggg agccttgctg aatgacaagc actccaatgg actgtcaaa acagaagcc | 420 |
| ctcacagaac attaatgagt tgtcctgtgg gtgaggctcc ctccccatat aactcaaggt | 480 |
| ttgagtctgt tgcttggtca gcaagtgctt gccatgatgg caccagttgg ttgacgattg | 540 |
| gaatttctgg cccagacaat ggggctgtgg ctgtattgaa atacaatggc ataataacag | 600 |
| acactatcaa gagttggagg aacaacatac tgagaactca agagtctgaa tgtgcatgtg | 660 |
| taaatggctc ttgctttact gtaatgactg acggaccaag taatggtcag gcatcacata | 720 |
| agatcttcaa aatggaaaaa gggaaagtgg ttaaatcagt cgaattggat gctcctaatt | 780 |
| atcactatga ggaatgctcc tgttatccta atgccggaga aatcacatgt gtgtgcaggg | 840 |
| ataattggca tggctcaaat cggccatggg tatctttcaa tcaaaatttg gagtatcaaa | 900 |
| taggatatat atgcagtgga gttttcggag acaatccacg ccccaatgat ggaacaggta | 960 |
| gttgtggtcc ggtgtcctct aacggggcat atggggtaaa agggttttca tttaaatacg | 1020 |
| gcaatggtgt ctggatcggg agaaccaaaa gcactaattc caggagcggc tttgaaatga | 1080 |
| tttgggatcc aaatgggtgg actgaaacgg acagtagctt ttcagtgaaa caagatatcg | 1140 |
| tagcaataac tgattggtca ggatatagcg ggagttttgt ccagcatcca gaactgacag | 1200 |
| gactagattg cataagacct tgtttctggg ttgagttgat cagagggcgg cccaaagaga | 1260 |
| gcacaatttg gactagtggg agcagcatat cttttttgtgg tgtaaatagt gacactgtgg | 1320 |
| gttggtcttg gccagacggt gccgagttgc cattccacat tgacaagtag tttgttcaaa | 1380 |
| aaactccttg tttctact | 1398 |

<210> SEQ ID NO 3
<211> LENGTH: 1027
<212> TYPE: DNA
<213> ORGANISM: Artificial Sequence
<220> FEATURE:
<223> OTHER INFORMATION: Synthetic nucleotide

<400> SEQUENCE: 3

| | |
|---|---:|
| agcaaaagca ggtagatgtt gaaagatgag tcttctaacc gaggtcgaaa cgtacgttct | 60 |
| ctctatcatc ccgtcaggcc ccctcaaagc cgagatcgca cagaaacttg aagatgtctt | 120 |
| tgcaggaaag aacaccgatc tcgaggctct catggagtgg ctaaagacaa gaccaatcct | 180 |

```
gtcacctctg actaaaggga ttttgggatt tgtattcacg ctcaccgtgc ccagtgagcg    240
aggactgcag cgtagacgct ttgtccagaa tgccctaaat ggaaatggag atccaaataa    300
tatggatagg gcagttaagc tatataagaa gctgaaaaga gaaataacat tccatggggc    360
taaggaggtc gcactcagct actcaaccgg tgcacttgcc agttgcatgg gtctcatata    420
caacaggatg ggaacggtga ctacggaagt ggcttttggc ctagtgtgtg ccacttgtga    480
gcagattgca gattcacagc atcggtctca cagacagatg gcaactatca ccaacccact    540
aatcagacat gagaacagaa tggtgctggc cagcactaca gctaaggcta tggagcagat    600
ggcgggatca agtgagcagg cagcggaagc catggagatc gctaatcagg ctaggcagat    660
ggtgcaggca atgaggacaa ttgggactca tcctaactct agtgctggtc tgagagataa    720
tcttcttgaa aatttgcagg cctaccagaa acgaatggga gtgcagatgc agcgattcaa    780
gtgatcctat tgttgttgcc gcaaatatca ttgggatctt gcacttgata ttgtggattc    840
ttgatcgtct tttcttcaaa tgcatttatc gtcgccttaa atacggtttg aaaagagggc    900
ctgctacggc aggggtacct gagtctatga gggaagagta ccggcaggaa cagcagagtg    960
ctgtggatgt tgacgatggt cattttgtca acatagaatt ggagtaaaaa actaccttgt   1020
ttctact                                                              1027

<210> SEQ ID NO 4
<211> LENGTH: 875
<212> TYPE: DNA
<213> ORGANISM: Artificial Sequence
<220> FEATURE:
<223> OTHER INFORMATION: Synthetic nucleotide

<400> SEQUENCE: 4
agcaaaagca gggtgacaaa aacataatgg attccaacac tgtgtcaagc tttcaggtag     60
actgctttct ttggcatgtc cgcaaacgat ttgcagacca agaactgggt gatgccccat    120
tccttgaccg gcttcgccga gatcagaagt ccctaagagg aagaggcaac actcttggtc    180
tggacatcga aacagctact cgcgcaggaa agcagatagt ggagcggatt ctggaggggg    240
agtctgataa ggcacttaaa atgccggctt cacgctacct aactgacatg actctcgaag    300
aaatgtcaag ggactggttc atgctcatgc ccaagcagaa agtggcaggt tccctttgca    360
tcaaaatgga ccaggcaata atggataaaa ccatcatatt gaaagcaaac ttcagtgtga    420
tttttgaccg gttggaaacc ctaatactac ttagagcttt cacagaagaa ggagcaatcg    480
tgggagaaat ctcaccatta ccttctcttc aggacatac tggtgaggat gtcaaaaatg    540
caattggcgt cctcatcgga ggacttgaat ggaatgataa cacagttcga gtcactgaaa    600
ctatacagag attcgcttgg agaaacagtg atgaggatgg agactttca ctcccctccaa    660 atcagaaacg gtaaatggcg agaacaattg agtcagaagt ttgaagaaat aaggtggctg    720
attgaagaag taagacatag attgaaaatt acagaaaaca gcttcgaaca gataacgttt    780
atgcaagcct tacaactact gcttgaagtg gagcaagaga taagagcctt ctcgtttcag    840
cttatttaat gataaaaaac acccttgttt ctact                                875

<210> SEQ ID NO 5
<211> LENGTH: 1565
<212> TYPE: DNA
<213> ORGANISM: Artificial Sequence
<220> FEATURE:
<223> OTHER INFORMATION: Synthetic nucleotide
```

<400> SEQUENCE: 5

```
agcaaaagca gggtagataa tcactcaccg agtgacatca gcatcatggc gtctcaaggc    60
accaaacgat cttatgaaca gatggaaact ggtggggaac gccagaatgc tactgagatc   120
agggcatctg ttggaagaat ggttagtggc attgggaggt tctacataca gatgtgcaca   180
gaactcaaac tcagtgacta tgaagggagg ctgatccaga acagcataac aatagagaga   240
atggtactct ctgcatttga tgaaagaagg aacagatacc tggaagaaca ccccagtgcg   300
ggaaaggacc cgaagaagac tggaggtcca atttatcgga ggagagacgg gaaatgggtg   360
agagagctaa ttctgtacga caaagaggag atcaggagga tttggcgtca agcgaacaat   420
ggagaggacg caactgctgg tcttacccac ctgatgatat ggcattccaa tctaaatgat   480
gccacatatc agagaacgag agctctcgtg cgtactggaa tggacccaag gatgtgctct   540
ctgatgcaag ggtcaactct cccgaggaga tctggagctg ccggtgcagc agtaaagggg   600
gtagggacaa tggtgatgga gctgattcgg atgataaaac gagggatcaa cgaccggaat   660
ttctggagag gcgaaaatgg aagaagaaca aggattgcat atgagagaat gtgcaacatc   720
ctcaaaggga aattccaaac agcagcacaa agagcaatga tggatcaagt gcgagagagc   780
agaaatcctg gaatgctga aattgaagat ctcattttc tggcacggtc tgcactcatc   840
ctgagaggat cagtggccca taagtcctgc ttgcctgctt gtgtgtacgg acttgcagtg   900
gccagtggat atgactttga gagagaaggg tactctctgg ttggaataga tccttccgc   960
ctgcttcaaa acagccaggt ctttagtctc attagaccaa atgagaatcc agcacataag  1020
agtcaattag tgtggatggc atgccactct gcagcatttg aggaccttag agtctcaagt  1080
ttcatcagag ggacaagagt ggtcccaaga ggacagctat ccaccagagg ggttcaaatt  1140
gcttcaaatg agaacatgga ggcaatggac tccaacactc ttgaactgag aagcagatat  1200
tgggctataa gaaccagaag cggaggaaac accaaccagc agaggcatc tgcaggacag  1260
atcagcgttc agcccacttt ctcggtccag agaaaccttc ccttcgaaag agcgaccatt  1320
atggcagcat ttacaggaaa tactgagggc agaacgtctg acatgaggac tgaaatcata  1380
agaatgatgg aaagtgccag accagaagat gtgtcattcc aggggcgggg agtcttcgag  1440
ctctcggacg aaaaggcaac gaacccgatc gtgccttcct ttgacatgaa taatgaagga  1500
tcttatttct tcggagacaa tgcagaggag tatgacaatt aaagaaaaat acccttgttt  1560
ctact                                                              1565
```

<210> SEQ ID NO 6
<211> LENGTH: 2233
<212> TYPE: DNA
<213> ORGANISM: Artificial Sequence
<220> FEATURE:
<223> OTHER INFORMATION: Synthetic nucleotide

<400> SEQUENCE: 6

```
agcgaaagca ggtactgatc caaaatggaa gactttgtgc gacaatgctt caatccaatg   60
attgtcgagc ttgcggaaaa ggcaatgaaa gaatatgggg aagatccgaa atcgaaacg   120
aacaagtttg ctgcaatatg cacacacttg gaggtctgtt tcatgtattc ggattttcac  180
tttattgatg aacggagtga atcaataatt gtagaatctg gagatccgaa tgcattattg  240
aaacaccgat ttgaaataat tgaaggaaga gaccgaacga tggcctggac tgtggtgaat  300
agtatctgca acaccacagg agttgagaaa cctaaatttc tcccagattt gtatgactac  360
aaagagaacc gattcatcga aattggagtg acacggaggg aagttcatac atactatctg  420
```

```
gagaaagcca acaagataaa atccgaggag acacatattc acatattctc attcacaggg      480
gaggaaatgg ccaccaaagc ggactacacc cttgatgaag agagcagggc aagaattaaa      540
accaggctgt tcaccataag gcaggaaatg gccagtaggg gtctatggga ttcctttcgt      600
caatccgaga gaggcgaaga gacaattgaa gaaaaatttg aaatcactgg aaccatgcgc      660
agacttgcag accaaagtct cccaccgaac ttctccagcc ttgaaaactt tagagcctat      720
gtggatggat tcgaaccgaa cggctgcatt gagggcaagc tttctcaaat gtcaaaagaa      780
gtgaatgcta gaattgagcc attttttgaag acaacgccac gccctctcag actacctgat      840
gggcctcctt gctctcagcg gtcgaagttc ttgctgatgg atgcccttaa attaagcatc      900
gaagacccga gtcatgaggg ggaggggata ccactatacg atgcaatcaa atgcatgaag      960
acatttttcg gctggaaaga gcccaacatc gtgaaaccac atgaaaaagg tataaacccc     1020
aattacctcc tggcttggaa gcaagtgctg gcagaactcc aagatattga aaatgaggag     1080
aaaatcccaa aaacaaagaa catgaaaaaa acaagccagt tgaagtgggc actcggtgag     1140
aacatggcac cagagaaagt agactttgag gactgcaaag atgttagcga tctaagacag     1200
tatgacagtg atgaaccaga gtctagatca ctagcaagct ggattcagag tgaattcaac     1260
aaggcatgtg aattgacaga ttcgatttgg attgaactcg atgaaatagg agaagacgta     1320
gctccaattg agcacattgc aagtatgaga aggaactatt ttacagcgga agtatcccat     1380
tgcagggcca ctgaatacat aatgaaggga gtgtacataa acacagccct gttgaatgca     1440
tcctgtgcag ccatggatga ctttcaactg attccaatga taagcaaatg cagaaccaaa     1500
gaaggaagac ggaaaactaa tctgtatgga ttcattataa aagggagatc ccacttgagg     1560
aatgataccg atgtggtaaa ttttgtgagt atggaattct ctcttactga tccgaggctg     1620
gagccacaca agtgggaaaa gtactgtgtc ctcgagatag agacatgct cctccggact      1680 gcagtaggcc aagtttcgag gcccatgttc ctgtatgtaa gaaccaatgg aacctccaag     1740
atcaaaatga aatgggcat ggaaatgagg cgatgccttc ttcaatccct tcaacaaatt     1800
gaaagcatga ttgaagccga gtcttctgtc aaagagaagg acatgaccaa agaattcttt     1860
gaaaacaaat cagaaacatg gccgattgga gagtccccca agggagtgga ggaaggctcc     1920
atcggaaagg tgtgcagaac cttgctggcg aagtctgtgt tcaacagttt atatgcatct     1980
ccacaactcg agggttttc agctgaatca agaaaattgc ttctcattgc tcaggcactt     2040
agggacaacc tggaacctgg gaccttcgat cttggagggc tatatgaagc aattgaggag     2100
tgcctgatta cgatccctg ggttttgctt aatgcgtctt ggttcaactc cttcctcgca     2160
catgcactga aatagttgtg gcaatgctac tatttgctat ccatactgtc caaaaagta     2220 ccttgtttct act                                                        2233
```

<210> SEQ ID NO 7
<211> LENGTH: 2341
<212> TYPE: DNA
<213> ORGANISM: Artificial Sequence
<220> FEATURE:
<223> OTHER INFORMATION: Synthetic nucleotide

<400> SEQUENCE: 7

```
agcgaaagca ggcaaaccat ttgaatggat gtcaatccga ctttactttt cttgaaagta       60
ccagtgcaaa atgctataag taccaccttc ccttatactg gagaccctcc atacagccat      120
ggaacaggga caggatacac catggacaca gtcaacagaa cacaccaata ttcagaaaag      180
```

```
gggaagtgga caacaaacac agagactgga gcaccccaac tcaacccgat tgatggacca    240
ctacctgagg ataatgagcc cagtgggtac gcacaaacag attgtgtatt ggaagcaatg    300
gctttccttg aagaatccca cccagggatc tttgaaaact cgtgtcttga acgatggaa     360 attgttcaac aaacaagagt ggataaactg acccaaggtc gccagaccta tgactggaca    420
ttgaatagaa ccaaccggc tgcaactgct ttggccaaca ctatagaaat cttcagatcg     480
aacggtctaa cagccaatga atcgggacgg ctaatagatt tcctcaagga tgtgatggag    540
tcaatggata aggaagaaat ggagataaca acacatttcc agagaaagag aagggtgagg    600
gacaacatga ccaagaaaat ggtcacacaa agaacaatag gaagaaaaa caaaggctg      660 aacaaaaaga gctacctgat aagagcactg acactgaaca caatgacaaa agatgcagaa    720
agaggcaaat tgaagaggcg agcgattgca cacccggaa tgcaaatcag aggattcgtg     780
tactttgttg aaacactagc gaggagtatc tgtgagaaac ttgagcaatc tggactccca    840
gtcggaggga tgagaagaa ggctaaattg gcaaacgtcg tgaggaagat gatgactaac     900
tcacaagata ctgaactctc ctttacaatt actggagaca taccaaatg gaatgagaat     960 cagaatccta ggatgtttct ggcaatgata acgtacatca aaggaaccca gccagaatgg   1020
tttcggaatg tcttaagcat agctcctata atgttctcaa acaaaatggc gagactagga   1080 aaggataca tgttcgaaag taagagcatg aagttacgaa cacaaatacc agcagaaatg    1140
cttgcaaaca ttgatcttaa atacttcaat gaattaacga aaaagaaaat tgagaaaata   1200
aggcctctat aatagatgg tacagcctca ttgagccctg aatgatgat gggcatgttc     1260 aacatgctga gtacagtcct aggagtttca atcctgaatc ttggacagaa aaggtacacc   1320
aaaaccacat attggtggga cggactccaa tcctctgatg atttcgctct catcgtaaat   1380
gcaccgaatc atgagggaat acaagcagga gtggataggt tttataggac ttgtaaacta   1440
gttggaatca atatgagcaa gaagaagtct tacataaatc ggacagggac atttgaattc   1500
acgagctttt tctaccgcta tggatttgta gccaatttca gtatggagct gcccagtttt   1560
ggagtgtctg gaattaatga atcggccgac atgagcattg tgttacagt gataaaaac    1620 aatatgataa caacgacct tgggccagca acagctcaga tggctcttca gttattcatc    1680
aaggactaca gatacacata ccgatgccac agaggggata cgcaaatcca aacaaggaga   1740
tcattcgagc tgaagaagct gtgggagcaa acccgttcaa aggcaggact gttggtttca   1800
gatggaggac caaatctata caatatccga aacctccata ttcctgaagt ctgcttaaaa   1860
tgggaattga tggatgaaga ttaccagggc agactgtgta atcctctgaa tccattcgtc   1920
agccataagg aaattgaatc tgtcaacaat gctgtagtaa tgccagctca tggcccggcc   1980
aagagtatgg aatatgatgc cgttgcaact cacacattcat ggattcctaa aggaaccgt    2040 tccattctca atacgagtca aggggaatt cttgaggatg aacagatgta ccagaagtgc    2100
tgcaatctat tcgagaaatt cttccccagc agttcatatc ggaggccagt ggaatttcc    2160 agcatggtgg aggccatggt gtctagggcc cgaattgacg cacgaatcga tttcgagtct   2220
ggaaggatta agaagaaga gtttgccgag atcatgaaga tctgttccac cattgaagaa    2280
ctcagacggc aaaaatagtg aatttagctt gtccttcgtg aaaaaatgcc ttgtttctac   2340
t                                                                  2341

<210> SEQ ID NO 8
<211> LENGTH: 2341
<212> TYPE: DNA
<213> ORGANISM: Artificial Sequence
```

```
<220> FEATURE:
<223> OTHER INFORMATION: Synthetic nucleotide

<400> SEQUENCE: 8
agcgaaagca ggtcaaatat attcaatatg gagaggataa aagaattacg agatctaatg      60
tcacagtccc gcactcgcga gatactaaca aaaaccactg tggaccatat ggccataatc     120
aagaaataca catcaggaag acaagagaag aaccctgctc tcagaatgaa atggatgatg     180
gcaatgaaat atccaatcac agcggacaag agaataatag agatgattcc tgaaaggaat     240
gaacaagggc agacgctctg gagcaagaca atgatgctg atcggacag ggtgatggtg       300
tctcccctag ctgtaacttg gtggaatagg aatgggccgg cgacaagtgc agttcattat     360
ccaaaggttt acaaaacata ctttgagaag gttgaaagat taaaacatgg aaccttcggt     420
cccgttcatt tccgaaacca ggttaaaata cgccgccgag ttgatataaa tcctggccat     480
gcagatctca gtgctaaaga agcacaagat gtcatcatgg aggtcgtttt cccaaatgaa     540
gtgggagcta gaatattgac atcagagtcg caattgacaa taacgaaaga gaagaaagaa     600
gagctccaag attgtaagat tgctccctta atggttgcat acatgttgga aagggaactg     660
gtccgcaaga ccagattcct accggtagca ggcggaacaa gtagtgtgta cattgaggta     720
ttgcatttga ctcaagggac ctgctgggaa cagatgtaca ctccaggcgg agaagtgaga     780
aatgacgatg ttgaccagag tttgatcatt gctgccagaa acattgttag agagcaaca    840
gtatcagcgg atccactggc atcactgctg gagatgtgtc acagcacaca aattggtggg    900
ataaggatgg tggacatcct taggcaaaat ccaactgagg aacaagctgt ggatatatgc    960
aaagcagcaa tgggtcttag gatcagttct tcctttagct ttggaggctt cactttcaaa   1020
agaacaagtg gatcatccgt caagaaggaa gaggaagtgc ttacaggcaa cctccaaaca   1080
ttgaaaataa gagtacatga ggggtatgag gaattcacaa tggttgggcg gagggcaaca   1140
gctatcctga ggaaagcaac tagaaggctg attcagttga tagtaagtgg aagagaccaa   1200
caatcaatcg ctgaggcaat cattgtagca atggtgttct cacaggagga ttgcatgata   1260
aaggcagtcc gaggcgatct gaatttcgta aacagagcaa accaaagatt aaaccccatg   1320
catcaactcc tgagacattt tcaaaaggac gcaaagtgc tatttcagaa ttggggaatt   1380
gaacccattg ataatgtcat ggggatgatc ggaatattac ctgacatgac tccagcaca    1440
gaaatgtcac tgagaggagt aagagttagt aaaatgggag tggatgaata ttccagcact   1500
gagagagtag ttgtaagtat tgaccgtttc ttaagggttc gagatcagcg ggggaacgta   1560
ctcttatctc ccgaagaggt cagcgaaacc caggggaacag agaaattgac aataacatat   1620
tcatcatcaa tgatgtggga atcaacggt cctgagtcag tgcttgttaa cacctatcag   1680
tggatcatca gaaactggga gactgtgaag attcaatggt ctcaagaccc cacgatgctg   1740
tacaataaga tggagtttga accgttccaa tccttggtac ccaaagctgc cagaggtcaa   1800
tacagtggat ttgtgagaac attattccag caaatgcgtg acgtactggg gacatttgat   1860
actgtccaga taataaagct gctaccattt gcagcagccc caccgaagca gagcagaatg   1920
cagttttctt ctctaactgt gaatgtgaga ggctcaggaa tgagaatact cgtaaggggc   1980
aattcccctg tgttcaacta caataaggca accaaaaggc ttaccgtcct tggaaaggac   2040
gcaggtgcat taacagagga tccggatgaa gggacagccg agtggagtc tgcagtactg   2100
agggattct aatttttagg caaggaggac aaaaggtatg gaccagcatt gagcatcaat   2160
gaactgagca atcttgcgaa ggggagaaa gctaatgtgt gataggca aggtgacgtg    2220
```

-continued

```
gtgttggtaa tgaaacgaaa acgggactct agcatactta ctgacagcca gacagcgacc    2280
aaaagaattc ggatggccat caattagtgt cgaattgttt aaaaacgacc ttgtttctac    2340
t                                                                   2341
```

<210> SEQ ID NO 9
<211> LENGTH: 1767
<212> TYPE: DNA
<213> ORGANISM: Artificial Sequence
<220> FEATURE:
<223> OTHER INFORMATION: Synthetic nucleotide

<400> SEQUENCE: 9

```
agcaaaagca ggggttcaat ctgtcaaaat ggagaaaata gtgcttcttc ttgcaatagt      60
cagccttgtt aaaagtgatc agatttgcat tggttaccat gcaaacaact cgacagagca     120
ggttgacaca ataatggaaa gaacgtcac tgttacacat gcccaagaca tactggaaaa     180
gacacacaac gggaaactct gcgatctaga tggagtgaag cctctaattt tagagagatt    240
gtagtgtagc tggatggctc ctcgggaacc caatgtgtga cgaattcctc aatgtgccgg     300
aatggtctta catagtggag aagatcaatc cagccaatga cctctgttac ccagggtatt    360
tcaacgacta tgaagaactg aaacacctat tgagcagaat aaaccatttt gagaaaattc    420
agatcatccc caaagttct tggtcagaca tgaagcctca gcagggtga gctcagcatg    480 tccataccag ggaaggtcct ccttttttag aaatgtggta tggcttatca aaaggacaa     540 tgcatacca acaataaaga gaagttacaa taataccaac caagaagatc ttttggtatt    600
gtgggggatt caccatccaa atgatgcggc agagcagaca aggctctatc aaacccaac     660 tacctatatt tccgttggga catcaacact aaaccagaga ttggtaccaa aaatagccac    720
tagatctaag gtaaacgggc aaagtggaag gatggagttc ttttggacaa ttttaaaacc    780
gaatgatgca ataaactttg agagtaatgg aaatttcatt gctccagaaa atgcatacaa    840
aattgtcaag aaaggggact caacaattat gaaaagtgag ttggaatatg gtaactgcaa    900
caccaagtgt caaactccaa tagggcgat aaactctagt atgccattcc acaacatcca    960
ccctctcacc atcggggaat gccccaaata tgtgaaatca agcagattag tccttgctac   1020
tgggctcaga atagccctc aaaccgagac ccgaggacta tttggagcta tagcaggttt    1080
tatagaggga ggatggcagg gaatggtaga tggttggtat gggtaccacc atagcaacga    1140
gcaggggagt gggtacgctg cagacaaaga atccactcaa aaggcaatag atggagtcac    1200
caataaggtc aactcgatca ttgacaaaat gaacactcag tttgaggctg ttggaaggga    1260
atttaataac ttagaaagga gaatagaaaa tttaaacaag aagatggaag acggattcct    1320
agatgtctgg acttataatg ctgaacttct ggttctcatg gaaaatgaga gaactctaga    1380
ctttcatgac tcaaatgtca agaaccttta cgacaaggtc cgactacagc ttagggataa    1440
tgcaaaggag cttggtaacg gttgtttcga gttctatcac agatgtgata atgaatgtat    1500
ggaaagtgta agaaacggaa cgtatgacta cccgcagtat tcagaagaag caagattaaa    1560
aagagaggaa ataagtggag taaaattgga atcaatagga acttaccaaa tactgtcaat    1620
ttattcaaca gtggcgagct ccctagcact ggcaatcatg gtggctggtc tatctttatg    1680
gatgtgctcc aatggatcgt tacaatgcag aatttgcatt taaatttgtg agttcagatt    1740
gtagttaaaa acacccttgt ttctact                                        1767
```

<210> SEQ ID NO 10
<211> LENGTH: 1398

<212> TYPE: DNA
<213> ORGANISM: Artificial Sequence
<220> FEATURE:
<223> OTHER INFORMATION: Synthetic nucleotide

<400> SEQUENCE: 10

```
agcaaaagca ggagttcaaa atgaatccaa atcagaagat aataaccatc ggatcaatct      60
gtatggtaat tggaatagtt agcttaatgt tacaaattgg gaacatgatc tcaatatggg     120
tcagtcattc aattcagaca gggaatcaat gccaagctga accaatcagc aatactaaat     180
ttcttactga gaaagctgtg gcttcagtaa cattagcggg caattcatct ctttgcccca     240
ttagcggatg ggctgtatac agtaaggaca acagtataag gatcggttcc agggggatg      300
tgtttgttat aagagagccg ttcatctcat gctcccactt ggaatgcaga actttctttt     360
tgactcaggg agccttgctg aatgacaagc actccaatgg gactgtcaaa gacagaagcc     420
ctcacagaac attaatgagt tgtcctgtgg gtgaggctcc ctccccatat aactcaaggt     480
ttgagtctgt tgcttggtca gcaagtgctt gccatgatgg caccagttgg ttgacaattg     540
gaatttctgg tccagacaat ggggctgtgg ctgtattgaa atacaatggc ataataacag     600
acaccatcaa gagttggagg aacaacatac tgagaactca agtctgaa tgtgcatgtg       660
taaatggctc ttgctttact gtaatgactg atggaccaag tagtgggcag gcatcatata     720
agatcttcaa aatggaaaaa gggaaagtgg ttaaatcagt cgaattggat gctcctaatt     780
atcactatga ggagtgctcc tgttatcctg atgccggcga aatcacatgt gtgtgcaggg     840
ataattggca tggctcaaat aggccatggg tatcttcaa tcaaaatttg gagtatcaaa      900
taggatatat atgcagtgga gttttcggag acaatccacg ccccaatgat ggaacaggta     960
gttgtggtcc ggtgttctct aacggggcat atggggtaaa agggttttca ttcaaatacg    1020
gcaatggtgt ttggatcggg agaaccaaaa gcactaattc caggagcggc tttgaaatga    1080
tttgggaccc aaatgggtgg actgaacgg acagtagctt tcggtgaag caagatatcg      1140
tagcaataac tgattggtca ggatatagcg ggagttttgt ccagcatcca gaactgacag    1200
gattagattg cataagacct tgtttctggg ttgagttaat cagagggcgg cctaaagaga    1260
gcacaatttg gaccagtggg agcagcatat ctttttgtgg tgtaaatagt gacactgtta    1320
gttggtcttg gccagacggt gctgagttgc cattcaccat tgacaagtag tttgttcaaa    1380
aaactccttg tttctact                                                  1398
```

<210> SEQ ID NO 11
<211> LENGTH: 1767
<212> TYPE: DNA
<213> ORGANISM: Artificial Sequence
<220> FEATURE:
<223> OTHER INFORMATION: Synthetic nucleotide

<400> SEQUENCE: 11

```
agcaaaagca ggggttcaat ctgtcaaaat ggagaaaata gtgcttcttc ttgcaatagt      60
cagccttgtt aaaagtgatc agatttgcat tggttaccat gcaaacaact cgacagagca    120
ggttgacaca ataatggaaa agaacgttac tgttacacat gcccaagaca tactggaaaa    180
gacacacaac gggaagctct gcgatctaga tggagtgaag cctctgattt taagagattg    240
tagtgtagct ggatggctcc tcggaaaccc aatgtgtgac gaattcatca atgtgccgga    300
atggtcttac atagtggaga aggccaaccc agccaatgac ctctgttacc cagggaattt    360
caacgactat gaagaactga aacacctatt gagcagaata aaccattttg agaaaattca    420
```

```
gatcatcccc aaaagttctt ggtccgatca tgaagcctca tcagggtga gctcagcatg    480 tccataccag ggaacgccct ccttttcag aaatgtggta tggcttatca aaagaacaa     540 tacataccca acaataaaga gaagctacaa taataccaac caggaagatc ttttgatact   600 gtggggatt catcattcta atgatgcggc agagcagaca aagctctatc aaacccaac     660 cacctatatt tccgttggga catcaacact aaaccagaga ttggtaccaa aaatagctac   720
tagatccaaa gtaaacgggc aaagtggaag gatggatttc ttctggacaa ttttaaaacc   780
gaatgatgca atcaacttcg agagtaatgg aaatttcatt gctccagaat atgcatacaa   840
aattgtcaag aaaggggact cagcaattgt taaaagtgaa gtggaatatg gtaactgcaa   900
cacaaagtgt caaactccaa taggggcgat aaactctagt atgccattcc acaacataca   960
ccctctcacc atcggggaat gccccaaata tgtgaaatca acaaattag tccttgcgac    1020 tgggctcaga aatagtcctc aaaccgagac ccgaggacta tttggagcta tagcagggtt   1080
tatagaggga ggatggcagg gaatggtaga tggttggtat gggtaccacc atagcaatga   1140 gcagggagt gggtacgctg cagacaaaga atccactcaa aaggcaatag atggagtcac    1200
caataaggtc aactcgatca ttgacaaaat gaacactcag tttgaggccg ttggaaggga   1260
atttaataac ttagaaagga aatagagaa tttaaacaag aaaatggaag acggattcct    1320
agatgtctgg acttataatg ctgaacttct ggttctcatg gaaaatgaga gaactctaga   1380
cttccatgat tcaaatgtca agaacctta cgacaaggtc cgactacagc ttagggataa    1440
tgcaaaggag ctgggtaacg gttgtttcga gttctatcac aaatgtgata atgaatgtat   1500
ggaaagtgta agaaacggaa cgtatgacta cccgcagtat tcagaagaag caagattaaa   1560
aagagaggaa ataagtggag taaaattgga atcaatagga acttaccaaa tactgtcaat   1620
ttattcaaca gttgcgagtt ctctagcact ggcaatcatg gtggctggtc tatctttgtg   1680
gatgtgctcc aatgggtcgt tacaatgcag aatttgcatt taaatttgtg agttcagatt   1740
gtagttaaaa acacccttgt ttctact                                       1767

<210> SEQ ID NO 12
<211> LENGTH: 1397
<212> TYPE: DNA
<213> ORGANISM: Artificial Sequence
<220> FEATURE:
<223> OTHER INFORMATION: Synthetic nucleotide

<400> SEQUENCE: 12
agcaaaagca ggagttcaaa atgaatccaa atcagaagat aataaccatt gggtcaatct     60
gtatggtaat tggaatagtt agcttaatgt tacaaattgg gaacatgatc tcaatatggg   120
tcagtcattc aattcaaaca gggaatcaac accaagctga accaatcaga atgctaattt   180
ttcttactga gaacgctgtg gcttcagtaa cattagcggg caattcatct ctttgccccg    240
ttagaggatg gctgtacac agtaaagaca acagtataag gattggttcc aaggggatg     300 ttttgttatt agagagccgt tcatctcatg ctcccacttg aatgcagaa ctttcttttt    360 gactcaggga gccttactga atgacaagca ctccaatggg actgtcaaag acagaagccc   420
tcacagaaca ttaatgagtt gtcctgtggg tgaggctccc tccccatata actcaaggtt   480
tgagtctgtt gcttggtcag caagtgcttg ccatgatggc accagttggt tgacaattgg   540
aatttctggc ccagacaatg gggctgtggc tgtattgaaa tacaatggca taataacaga   600
cactatcaag agttggagga acaacatact gagaactcaa gagtctgaat gtgcatgtgt   660
aaatggctct tgctttactg taatgactga tggaccaagt aatgggcagg catcatataa   720
```

```
gatcttcaaa atggaaaaag ggaaagtggt taaatcagtc gaattgaatg ctcctaatta      780
tcactatgag gaatgctcct gttatcctga tgctggcgaa atcacatgtg tgtgcaggga      840
taattggcat ggctcgaata ggccatgggt atctttcaat cagaatttgg agtatcaaat      900
aggatatata tgcagtggag ttttcggaga caatccacgc cccaatgatg gaacaggtag      960
ttgtggtcca gtgtccccta acggggcata tgggataaaa gggttttcat ttaaatacgg     1020
caatggtgtt tggatcggaa gaaccaaaag cactaattcc aggagcggct ttgaaatgat     1080
ttgggatcca aatgggtgga ctgaaacgga cagtaacttt tcggtgaaac aagatatagt     1140
agcaataact gattggtcag gatatagcgg gagttttgtc cagcatccag aactgacagg     1200
attagattgc ataagacctt gcttctgggt tgagttaatc agagggcggc ccaaagagag     1260
cacaatttgg actagtggga gcagcatatc tttttgtggt gtaaatagtg acactgtgag     1320
ttggtcttgg ccagacggtg ctgagttgcc attcaccatt gacaagtagt ttgttcaaaa     1380
aactccttgt ttctact                                                    1397
```

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Glu Arg Arg Arg Lys Lys Arg
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

Thr Glu Thr Arg
1

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Arg Arg Arg Lys
1

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Asn Thr Pro Gln Arg Glu Arg Arg Arg Lys Lys Arg Gly Leu Phe Gly
1               5                   10                  15

Ala Ile

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide

<400> SEQUENCE: 17

Asn Thr Pro Gln Thr Glu Thr Arg Gly Leu Phe Gly Ala Ile
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18

Asn Ser Pro Gln Arg Glu Arg Arg Lys Lys Arg Gly Leu Phe Gly
1               5                   10                  15

Ala Ile

<210> SEQ ID NO 19
<211> LENGTH: 14
<212> TYPE: PRT
<213> ORGANISM: Artificial Sequence
<220> FEATURE:
<223> OTHER INFORMATION: Synthetic peptide

<400> SEQUENCE: 19

Asn Ser Pro Gln Thr Glu Thr Arg Gly Leu Phe Gly Ala Ile
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide

<400> SEQUENCE: 20

Asn Ser Pro Leu Arg Glu Arg Arg Lys Lys Arg Gly Leu Phe Gly
1               5                   10                  15

Ala Ile

<210> SEQ ID NO 21
<211> LENGTH: 4
<212> TYPE: PRT
<213> ORGANISM: Artificial Sequence
<220> FEATURE:
<223> OTHER INFORMATION: Synthetic peptide

<400> SEQUENCE: 21

Arg Arg Lys Lys
1